(12) United States Patent
Xu et al.

(10) Patent No.: US 9,902,736 B2
(45) Date of Patent: Feb. 27, 2018

(54) 1-OXO/ACYLATION-14-ACYLATED ORIDONIN DERIVATIVE, PREPARATION METHOD THEREFOR AND APPLICATION THEREOF

(71) Applicant: HANGZHOU BENSHENG PHARMACEUTICAL CO., LTD., Zhejiang (CN)

(72) Inventors: Rongzhen Xu, Zhejiang (CN); Frank Rong, Zhejiang (CN); Fuwen Xie, Fujian (CN); Hongxi Lai, Fujian (CN)

(73) Assignee: HANGZHOU BENSHENG PHARMACEUTICAL CO., LTD., Hangzhou, Zhejiang (CN)

(*) Notice: Subject to any disclaimer, the term of this patent is extended or adjusted under 35 U.S.C. 154(b) by 0 days.

(21) Appl. No.: 14/373,556

(22) PCT Filed: Jan. 21, 2013

(86) PCT No.: PCT/CN2013/070803
§ 371 (c)(1),
(2) Date: Jul. 21, 2014

(87) PCT Pub. No.: WO2013/107429
PCT Pub. Date: Jul. 25, 2013

(65) Prior Publication Data
US 2014/0364490 A1   Dec. 11, 2014

Related U.S. Application Data

(63) Continuation of application No. PCT/CN2012/000124, filed on Jan. 21, 2012.

(51) Int. Cl.
   *C07D 493/08* (2006.01)
(52) U.S. Cl.
   CPC .................. *C07D 493/08* (2013.01)
(58) Field of Classification Search
   CPC .................................................. C07D 493/08
   See application file for complete search history.

(56) References Cited

FOREIGN PATENT DOCUMENTS

| CN | 101139350 A | 3/2008 |
| CN | 102295649 A | 12/2011 |
| WO | 2010/119423 A2 | 10/2010 |

OTHER PUBLICATIONS

Fujita et al., caplus an 1967:473701.*
Xu et al., caplus an 2012:2409.*
Xu et al., 2012, caplus an 2012:2409.*
Patani et al., Chem. REv., 1996, 96, 3147-3176.*
LungCancerPrevention, 2017,https://www.cancer.org/cancer/non-small-cell-lung-cancer/causes-risks-prevention/prevention.html.*
CancerPrevention, 2017,http://www.cancerresearchuk.org/about-cancer/causes-of-cancer/can-cancer-be-prevented.*
Cancer-Cure, 2017,http://www.cancerresearchuk.org/about-cancer/what-is-cancer/why-some-cancers-come-back.*
LungCancer, 2017, http://www.cancerresearchuk.org/about-cancer/what-is-cancer/why-some-cancers-come-back.*
Wu et al. "Preparation and Evaluation of Oridonin Derivatives". Chinese Herbal Medicines. 2009, vol. 40, No. 3, pp. 348-352.
International Search Report for International Application No. PCT/CN2013/070803, dated Apr. 25, 2013 (4 pages).
International Preliminary Report on Patentability for International Application No. PCT/CN2013/070803, dated Jul. 22, 2014 (8 pages).
Xu et al. (2008) "Synthesis and biological evaluation of novel 1-O- and 14-O-derivatives of oridonin as potential anticancer drug candidates," Bioorganic and Medicinal Chemistry Letters. 18:4741-4744.
Xu et al. (Feb. 2011) "Synthesis of oridonin derivatives and their inhibition on t(8;21) leukemia," Chinese Journal of Medicinal Chemistry. 21(1):1-2.—English Abstract and Drawings Only.
Fujita et al. (1981) "Antitumor Activity of Acylated Oridonin," Chem. Pharm. Bull. 29(11):3208-3213.

* cited by examiner

*Primary Examiner* — Sun Jae Yoo
(74) *Attorney, Agent, or Firm* — Brian C. Trinque; Lathrop Gage LLP

(57) ABSTRACT

The present invention relates to the fields of natural medicine and medicinal chemistry, and more particularly to a 1-oxo/acylated-14-acylated oridonin derivative of a general formula (I) or a pharmaceutically acceptable salt thereof, a method for preparing the compounds, a pharmaceutical composition comprising the compounds, and application thereof in preparation of antitumor drugs.

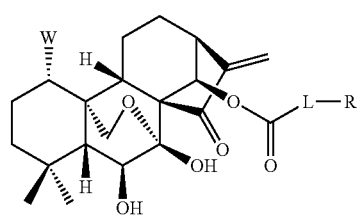

I

17 Claims, No Drawings

1-OXO/ACYLATION-14-ACYLATED ORIDONIN DERIVATIVE, PREPARATION METHOD THEREFOR AND APPLICATION THEREOF

RELATED APPLICATIONS

This application is a 35 U.S.C. § 371 filing of International Application No. PCT/CN2013/070803, filed Jan. 21, 2013, which claims priority to International Application No. PCT/CN2012/000124, filed Jan. 21, 2012, each of which is incorporated herein by reference in its entirety.

TECHNICAL FIELD

The present invention belongs to the field of natural medicine and pharmaceutical chemistry and relates to novel oridonin derivatives, in particular 1-oxo/acylated-14-acylated oridonin derivative, to a method for the preparation of these compounds, compositions containing such compounds and their applications in preparing antineoplastic medicaments.

BACKGROUND OF THE INVENTION

Oridonin is a shellene diterpenoid type of natural organic compound, which is separated from the plant Rabdosia rubescens (Labtea, Rabdosia) and is a main component of Herba Rabdosiae.

It has heat-cleaning and detoxicating effects, effects of promoting blood circulation and removing blood stasis, and anti-bacterial, anti-inflammatory and anti-tumor effects (ZHAO Yongxing et al. Preparation and in vitro anticancer effect of oridonin nanoparticles [J]. China Journal of Hospital Pharmacy, 2008, 28 (11): 864-867; L I U Chenjiang et al., Antitumor effect of oridonin [J]. China Pharmaceutical Journal, 1998, 33:577).

Scientists have conducted extensive research on oridonin and analogues thereof, including separation, purification, structural identification and modification, studies of biological activity in vivo and in vitro, in the hope of discovering novel medications with clinical applications (L I U Ke et al., Oridonin derivative and preparation thereof [P]. CN 101723951, 2010; L U Jinjian et al., Natural anticancer products separated from Chinese herbal medicine [J]. China Journal of Chinese Materia Medica, 2011, 6:27-27; ZHAO Ming et al. One single HPLC-PDA/(−)ESI-MS analysis to simultaneously determine 30 components of the aqueous extract of Rabdosia rubescens [J]. Journal of Chromatography B: Analytical Technologies in the Biomedical and Life Sciences, 2011, 879 (26): 2783-2793; ZHAO Peng et al. UPLC method for determination of oridonin content in Rabdosia plant [J]. Chinese Traditional Patent Medicine, 2011, 3 (3): 540-542; S U N Handong et al., Rabdosia plant diterpenoid compounds, Science Press, 2001; X U Jinyi et al., Oridonin derivative and preparation method thereof [P]. CN 101139350, 2008; X U Jinyi et al., Ent-6,7-open-cycle kaurene type rubescenesine A derivative with anti-tumor activity and preparation method and use thereof [P]. CN 102002051, 2011; X U Jinyi et al., Oridonin with antitumor resistance activity, fluorine-containing derivative of 6,7-open ring oridonin, preparation method and application thereof [P]. CN102295649, 2011).

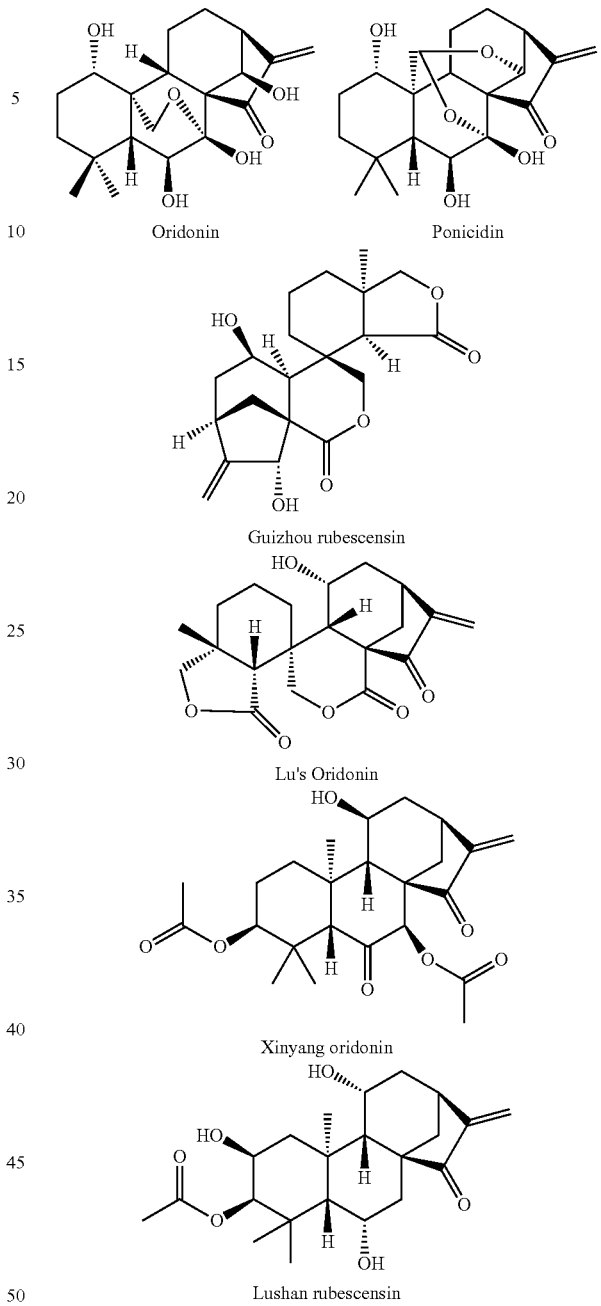

Oridonin

Ponicidin

Guizhou rubescensin

Lu's Oridonin

Xinyang oridonin

Lushan rubescensin

Studies have found that oridonin has cytotoxic effect with a broad anti-tumor spectrum, including acute myeloid leukemia, chronic myelogenous leukemia, uterine cancer, breast cancer, lymphoma, osteosarcoma, gastric cancer, esophageal cancer, liver cancer, gallbladder cancer, nasopharyngeal carcinoma, lung cancer, melanoma, skin cancer etc. (L I U Jiayin et al., Progress in research of oridonin and antitumor activity [J]. China Journal of New Drugs and Clinical Remedies, 2010, 29 (2): 81-84).

Oridonin induces apoptosis of tumor cells through the control of mitochondrial apoptotic pathway and achieves the effect of blocking cell cycle and malignant growth mainly by controlling the following conversion pathways: p53, Ras/Raf/ERK, PI3K/Akt and NF-k13 (L I Chunyang et al., Oridonin: a diterpene having cancer treatment activity in blocking cell cycle, inducing cell apoptosis and autophagy [J]. International Journal of Biochemistry and Cell Biology, 2011, 43 (5): 701-704; L I Xiaojie et al., Oridonin regulates mitochondrial apoptosis by controlling signal conversion pathway [J]. Cancer Research and Clinic, 2010, 22 (4): 286-288).

The poor water solubility and low bioavailability of oridonin has limited its clinic applications. Researches have been done on the structural modification of oridonin with an eye to find a compound with better activities. The Fujita group of Japan has structurally modified the 14-position hydroxyl of oridonin and discovered that only the derivative acylated at 14-position with long-chain fatty acids has a biological activity significantly higher than that of oridonin itself (Fujita, Eiichi. Biologic and physiological activity.II Antitumor activity of acylated oridonin [J], Chemic & Pharmaceutical Bulletin, 1981, 29(11):3208-3213).

This field is in need of novel compounds with antitumor activity, particularly having improved antitumor activity.

SUMMARY OF THE INVENTION

One object of the present invention is to provide novel 1-oxo/acylated-14-acylated oridonin derivatives of formula (I), or a pharmaceutically acceptable salt thereof,

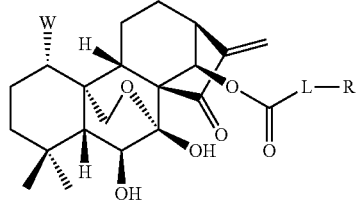

I wherein W is oxo or —O(CO)R';
L is selected from the group consisting of direct bond, —(CH=CH)$_n$—, piperidinocarbonyl, piperidinosulfonyl, cyclohexylaminocarbonyl, and cyclohexylaminosulfonyl;
n is 1 or 2;
R' is $C_1$-$C_6$alkyl;
R is aryl, heteroaryl, $C_3$-$C_7$ cycloalkyl, $C_3$-$C_7$ cycloalkenyl, heterocyclyl, $C_1$-$C_6$ alkyl, amino $C_1$-$C_6$ alkyl, ($C_1$-$C_6$ alkyl) amino $C_1$-$C_6$ alkyl, di($C_1$-$C_6$ alkyl)amino $C_1$-$C_6$ alkyl, hydroxyl $C_1$-$C_6$ alkyl, aryl $C_1$-$C_6$ alkyl, or heteroaryl $C_1$-$C_6$ alkyl;
wherein, the aryl, heteroaryl, $C_3$-$C_7$ cycloalkyl, $C_3$-$C_7$ cycloalkenyl and heterocyclyl are respectively optionally substituted with a substituent selected from the group consisting of halogen, amino, $C_1$-$C_6$ alkylamino, di($C_1$-$C_6$ alkyl) amino, nitro, cyano, hydroxyl, $C_1$-$C_6$ alkoxy, $C_1$-$C_6$ haloalkoxy, thiol, $C_1$-$C_6$ alkylthio, $C_1$-$C_6$ alkyl, hydroxyl $C_1$-$C_6$ alkyl and $C_1$-$C_6$ haloalkyl; the $C_3$-$C_7$ cycloalkenyl is also optionally substituted with carboxyl; with a proviso that when W is —O(CO)CH$_3$, L-R is not methyl.

The second object of the present invention is to provide a process for preparing the 1-oxo/acylated-14-acylated oridonin derivative of formula (I) of the present invention.

The third object of the present invention is to provide a pharmaceutical composition comprising the compound of the present invention. Said pharmaceutical composition comprises at least one compound of the present invention and optionally a pharmaceutically acceptable excipient.

The fourth object of the present invention is to provide the use of the compound of the present invention or a pharmaceutical composition comprising said compound in the manufacture of a medicament, in particular an antitumor medicament. Correspondingly, the present invention provides a method for treating a subject suffering from tumor, comprising administering to the subject in need thereof an effective amount of at least one compound of the present invention. Said tumor is particularly selected from leukemia, multiple myeloma, lymphoma, liver cancer, gastric cancer, breast cancer, cholangiocellular carcinoma, pancreatic cancer, lung cancer, colorectal cancer, osteosarcoma, melanoma, human cervical cancer, glioma, nasopharyngeal carcinoma, laryngeal carcinoma, esophageal cancer, middle ear tumor, prostate cancer and the like.

The present invention also relates to the compounds of the present invention for use in treating a tumor.

DETAILED DESCRIPTION OF THE INVENTION

The present invention provides a 1-oxo/acylated-14-acylated oridonin derivative of formula (I), or a pharmaceutically acceptable salt thereof,

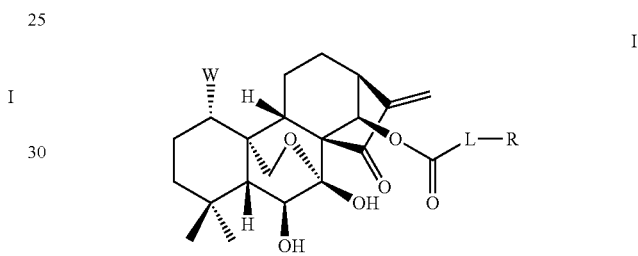

I wherein W is oxo or —O(CO)R';
L is selected from the group consisting of direct bond, —(CH=CH)$_n$—, piperidinocarbonyl, piperidinosulfonyl, cyclohexylaminocarbonyl, and cyclohexylaminosulfonyl;
n is 1 or 2;
R' is $C_1$-$C_6$alkyl;
R is aryl, heteroaryl, $C_3$-$C_7$ cycloalkyl, $C_3$-$C_7$ cycloalkenyl, heterocyclyl, $C_1$-$C_6$ alkyl, amino $C_1$-$C_6$ alkyl, ($C_1$-$C_6$ alkyl) amino $C_1$-$C_6$ alkyl, di($C_1$-$C_6$ alkyl)amino $C_1$-$C_6$ alkyl, hydroxyl $C_1$-$C_6$ alkyl, aryl $C_1$-$C_6$ alkyl, or heteroaryl $C_1$-$C_6$ alkyl;
wherein, the aryl, heteroaryl, $C_3$-$C_7$ cycloalkyl, $C_3$-$C_7$ cycloalkenyl and heterocyclyl are respectively optionally substituted with a substituent selected from the group consisting of halogen, amino, $C_1$-$C_6$ alkylamino, di($C_1$-$C_6$ alkyl) amino, nitro, cyano, hydroxyl, $C_1$-$C_6$ alkoxy, $C_1$-$C_6$ haloalkoxy, thiol, $C_1$-$C_6$ alkylthio, $C_1$-$C_6$ alkyl, hydroxyl $C_1$-$C_6$ alkyl and $C_1$-$C_6$ haloalkyl;
the $C_3$-$C_7$ cycloalkenyl is also optionally substituted with carboxyl;
with a proviso that when W is —O(CO)CH$_3$, L-R is not methyl.

The compound of the present invention has an antitumor activity. All the compounds of the present invention tested in the present application exhibit an antitumor activity superior to that of unmodified oridonin.

When W is oxo and L is direct bond or —(CH=CH)$_n$—, the compound of formula (I) is the compound of formula (I-1), wherein $R_1$ is defined as R in formula (I) and n defined as in formula (I).

When W is oxo and L is piperidinocarbonyl or piperidinosulfonyl, the compound of formula (I) is the compound of formula (I-2), wherein $R_2$ is —C(O)R or —C(O)S(O)$_2$R and the R is defined as in formula (I).

When W is oxo and L is cyclohexylaminocarbonyl or cyclohexylaminosulfonyl, the compound of formula (I) is the compound of formula (I-3), wherein $R_3$ is —C(O)R or —C(O)S(O)$_2$R and the R is defined as in formula (I).

When W is —O(CO)R' and L is direct bond or —(CH═CH)$_n$—, the compound of formula (I) is the compound of formula (I-4), wherein $R_1$ is defined as R in formula (I), $R_4$ is defined as R' in formula (I), and n is defined as in formula (I).

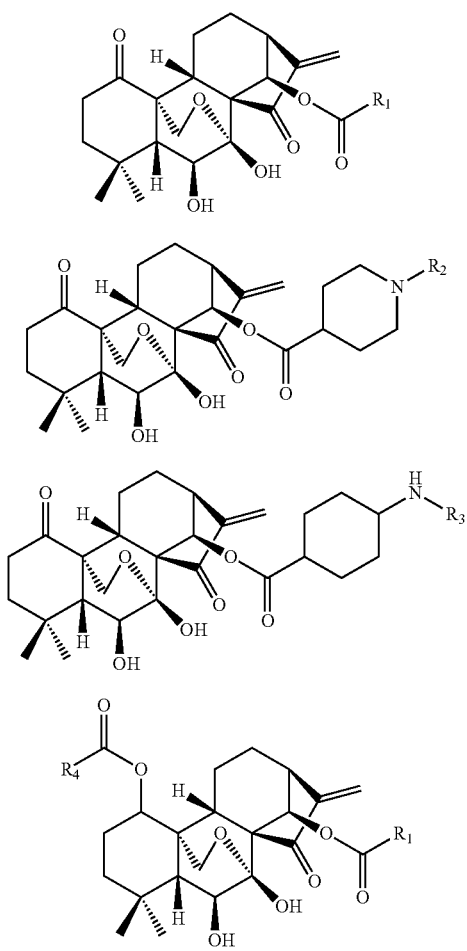

The 1-oxo/acylated-14-acylated oridonin derivative or a pharmaceutically acceptable salt thereof according to formula (I), wherein W is preferably oxo or formyloxy.

The 1-oxo/acylated-14-acylated oridonin derivative or a pharmaceutically acceptable salt thereof according to formula (I), wherein the aryl is preferably phenyl.

The 1-oxo/acylated-14-acylated oridonin derivative or a pharmaceutically acceptable salt thereof according to formula (I), wherein the heteroaryl is preferably a five-membered or six-membered aromatic ring group containing oxygen, nitrogen, or sulfur heteroatom, and more preferably the heteroaryl is furyl, thienyl, pyrrolyl, pyridyl, oxazolyl, etc.

The 1-oxo/acylated-14-acylated oridonin derivative or a pharmaceutically acceptable salt thereof according to formula (I), wherein the aryl, heteroaryl, $C_3$-$C_7$ cycloalkyl, $C_3$-$C_7$ cycloalkenyl and heterocyclyl are preferably respectively substituted optionally with a substituent selected from the group consisting of halogen, amino, nitro, cyano, $C_1$-$C_6$ alkoxy, $C_1$-$C_6$ haloalkoxy, $C_1$-$C_6$ alkylthio, and $C_1$-$C_6$ alkyl. More preferably, the substituent is fluoro, chloro, bromo, nitro, cyano, methoxy, ethoxy, propoxy, methyl, ethyl, propyl, isopropyl, trifluoromethyl, n-butyl, isobutyl, or tert-butyl.

The 1-oxo/acylated-14-acylated oridonin derivative or a pharmaceutically acceptable salt thereof according to formula (I), wherein R is preferably $C_3$-$C_7$ cycloalkyl, $C_3$-$C_7$ cycloalkenyl, $C_1$-$C_6$ alkyl, amino $C_1$-$C_6$ alkyl, aryl $C_1$-$C_6$ alkyl, or heteroaryl $C_1$-$C_6$ alkyl. More preferably, the R is cyclopropyl, cyclopentyl, cyclohexyl, cyclopentenyl, cyclohexenyl, methyl, ethyl, propyl, isopropyl, n-butyl, isobutyl, tert-butyl, aminobutyl, arylmethyl, or aryethyl.

Some 1-oxo/acylated-14-acylated oridonin derivatives of the present invention are shown below. These examples are only intended to further illustrate the present invention but not to make any limitation to the scope of the present invention.

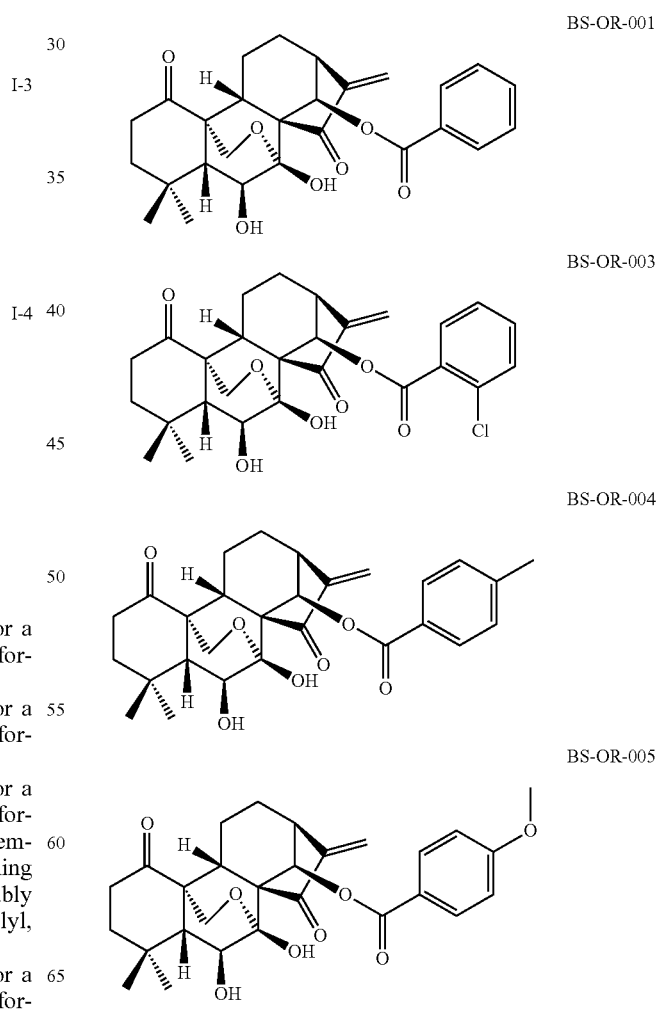

BS-OR-006
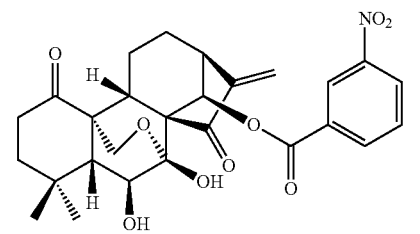
BS-OR-007
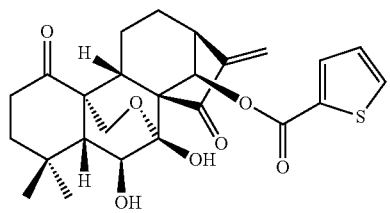
BS-OR-008
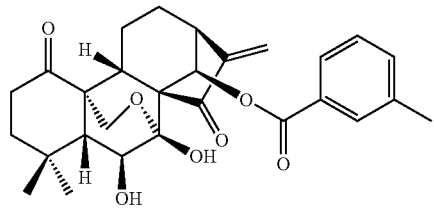
BS-OR-009
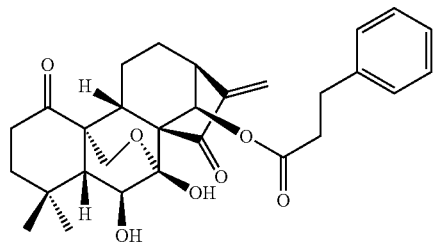
BS-OR-010
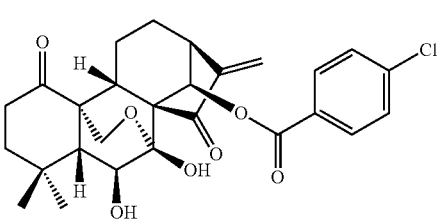
BS-OR-011
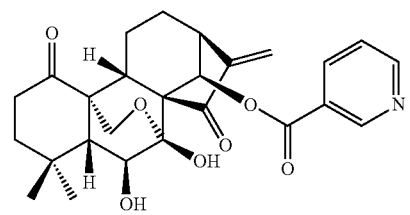
BS-OR-012
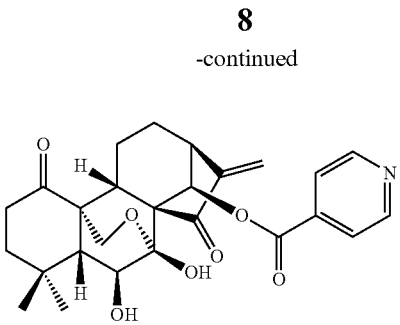
BS-OR-013
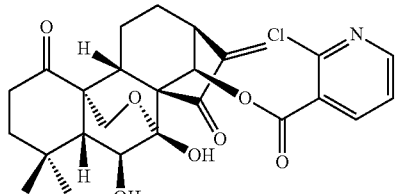
BS-OR-014
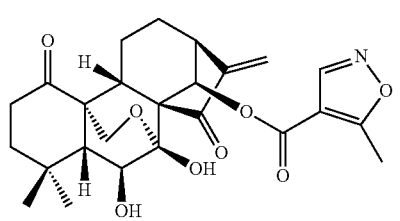
BS-OR-015
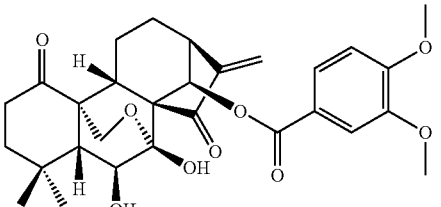
BS-OR-017
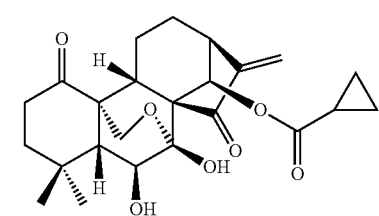
BS-OR-019
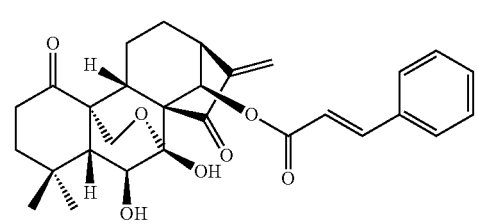
BS-OR-020
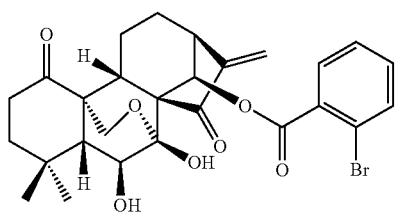

BS-OR-025
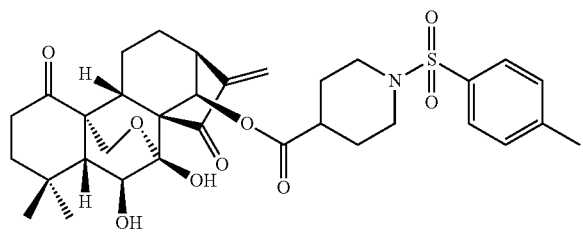
BS-OR-026
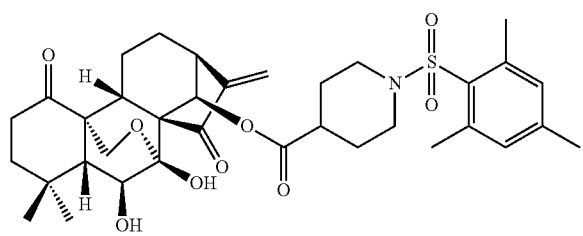
BS-OR-027
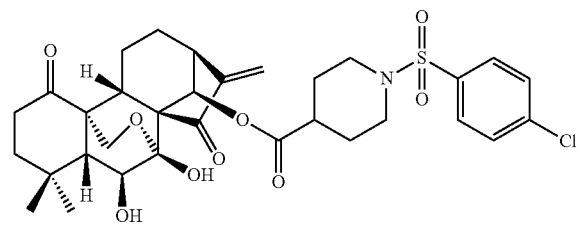
BS-OR-029
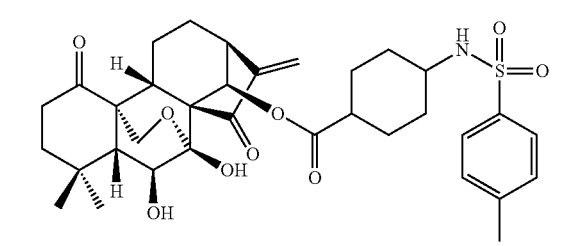
BS-OR-032
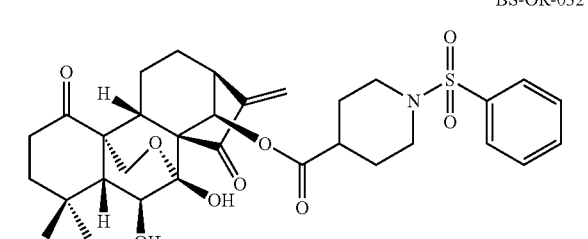
BS-OR-034
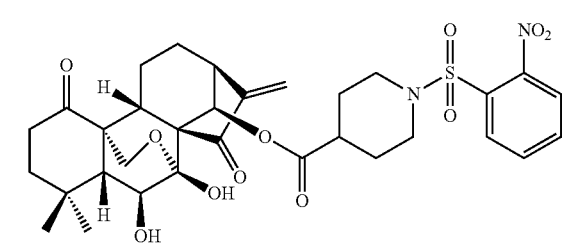
BS-OR-037
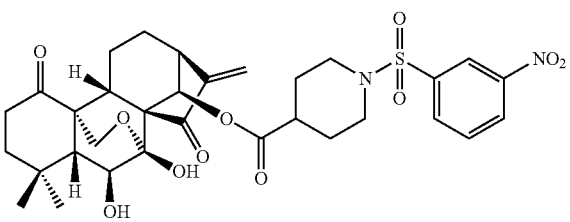
BS-OR-038
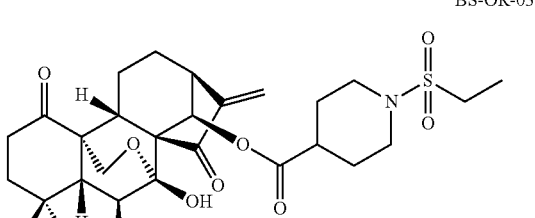
BS-OR-039
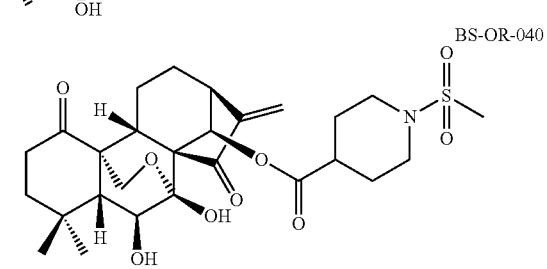
BS-OR-040
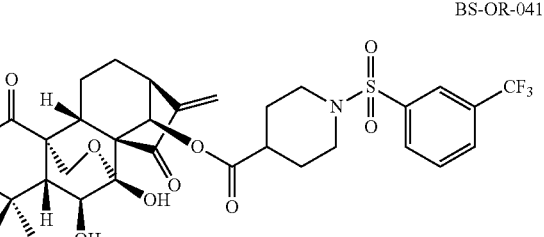
BS-OR-041
BS-OR-042
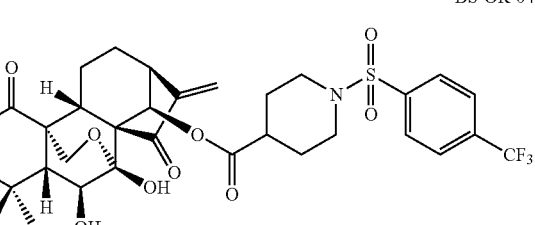

BS-OR-043
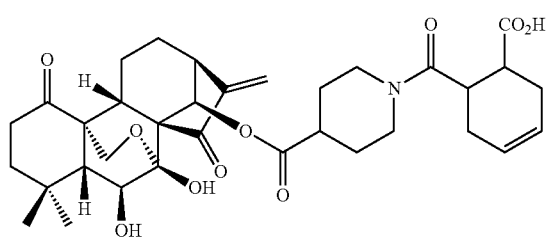
BS-OR-044
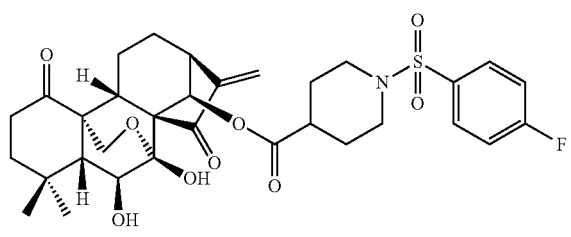
BS-OR-047
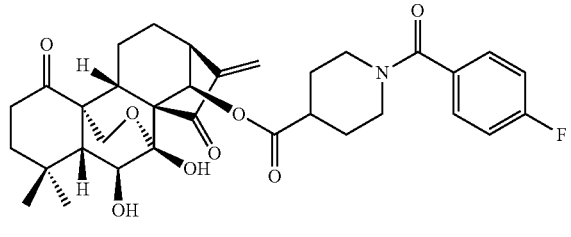
BS-OR-048
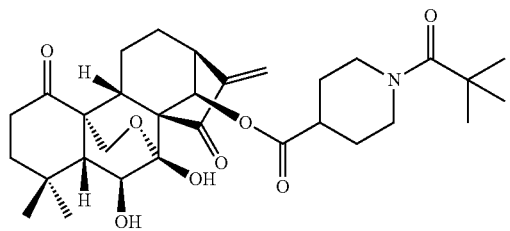
BS-OR-049
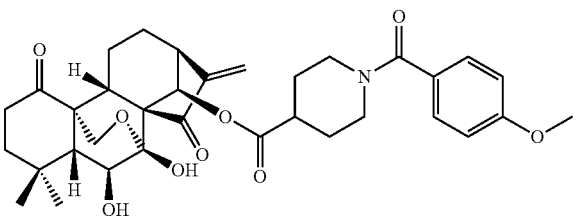
BS-OR-050
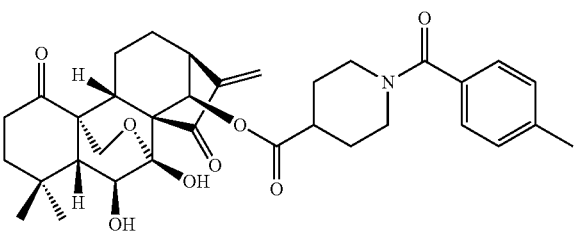
BS-OR-051
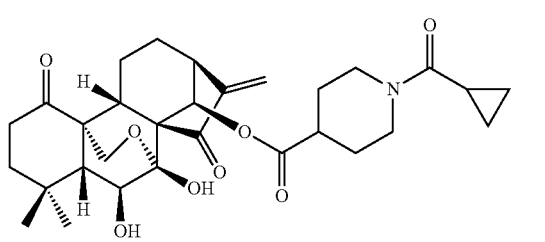
BS-OR-052
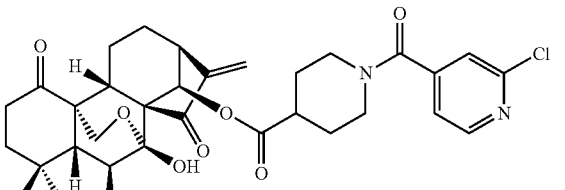
BS-OR-053
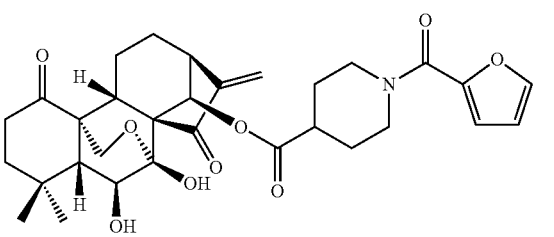
BS-OR-054
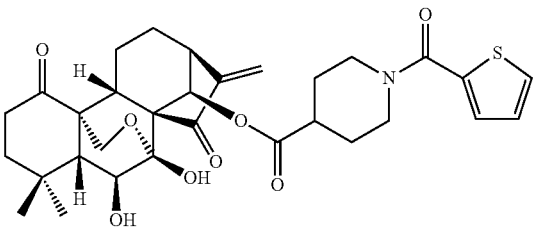
BS-OR-055
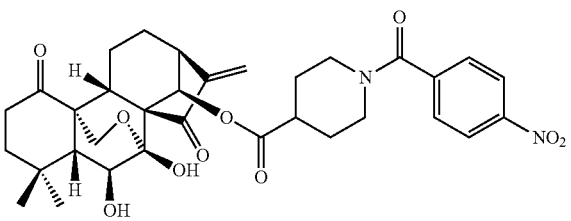
BS-OR-056
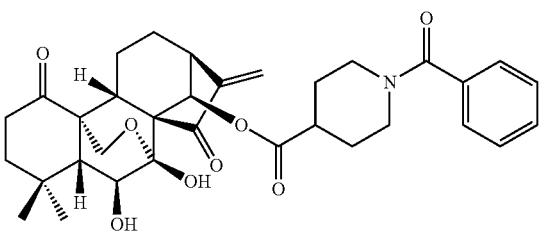

BS-OR-057
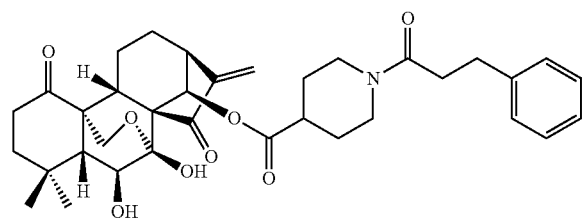
BS-OR-058
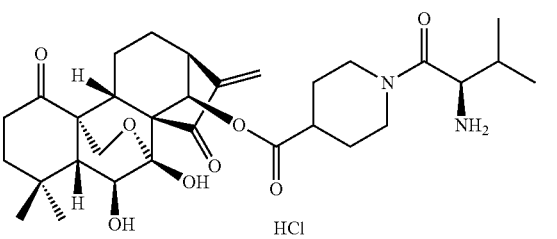
BS-OR-059
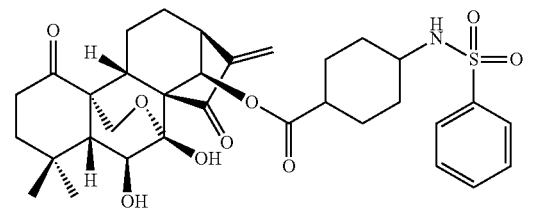
BS-OR-061
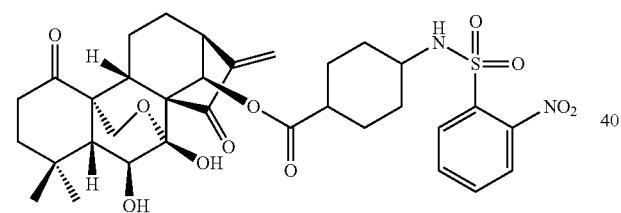
BS-OR-062
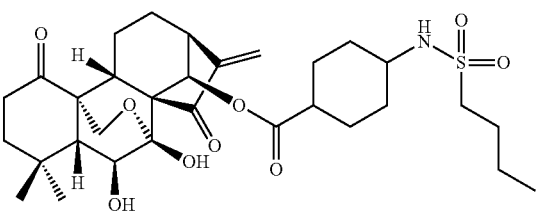
BS-OR-063
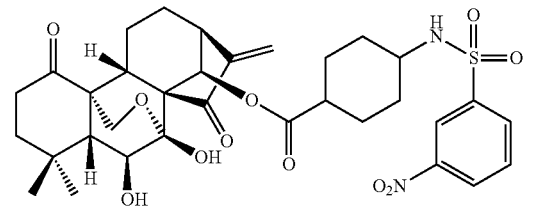
BS-OR-064
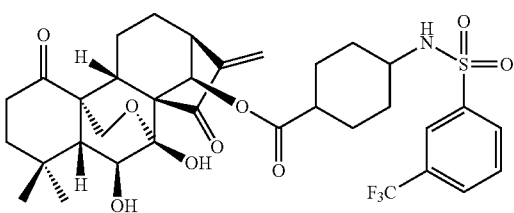
BS-OR-065
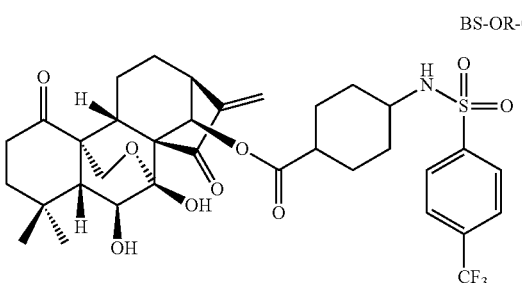
BS-OR-066
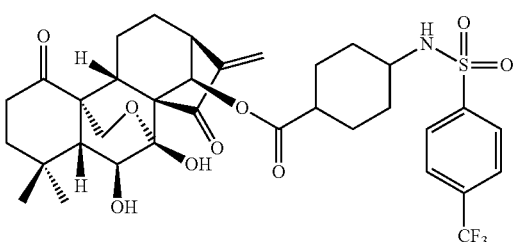
BS-OR-067
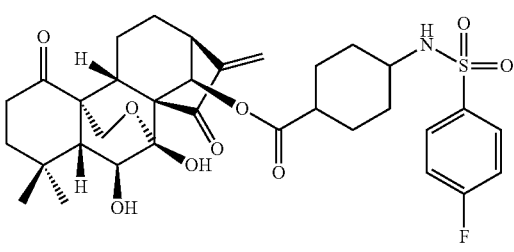
BS-OR-070
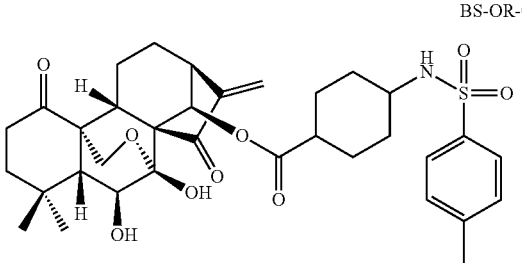
BS-OR-071
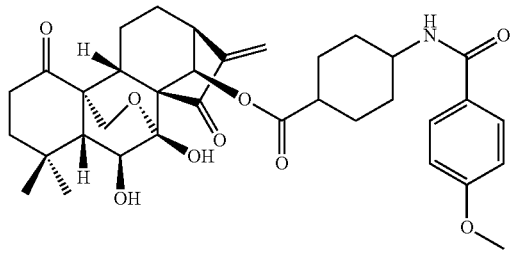

BS-OR-072
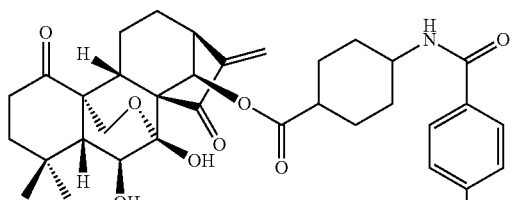
BS-OR-073
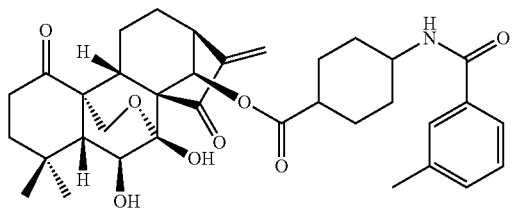
BS-OR-074
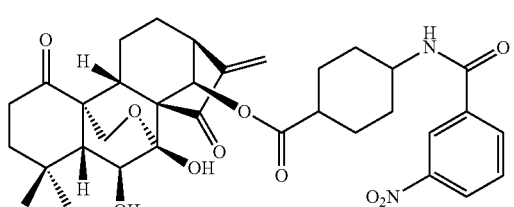
BS-OR-075
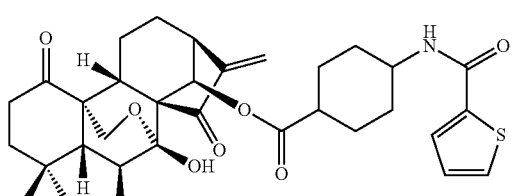
BS-OR-076
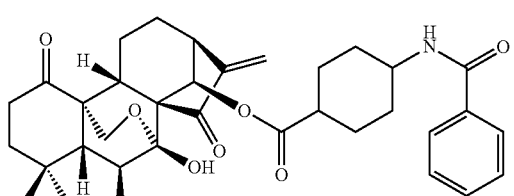
BS-OR-077
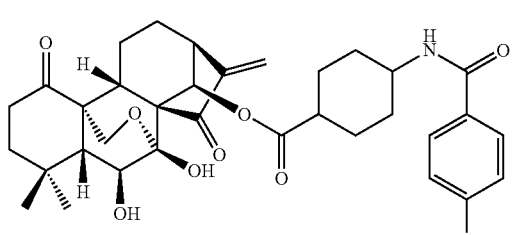
BS-OR-078
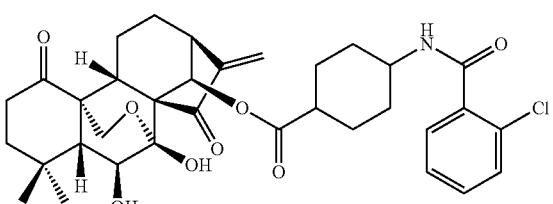
BS-OR-079
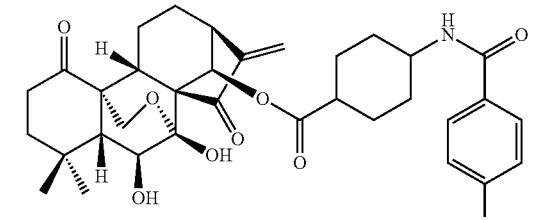
BS-OR-080
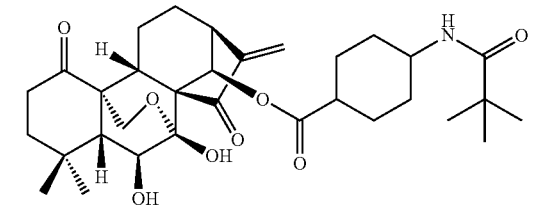
BS-OR-083
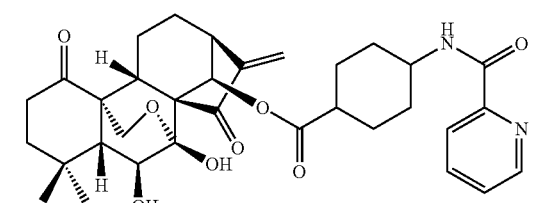
BS-OR-086
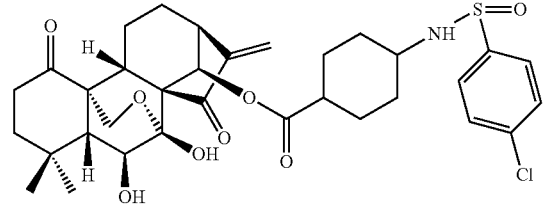
BS-OR-087
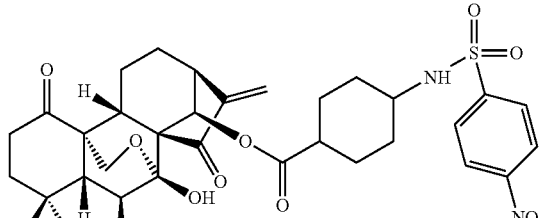

-continued

BS-OR-088

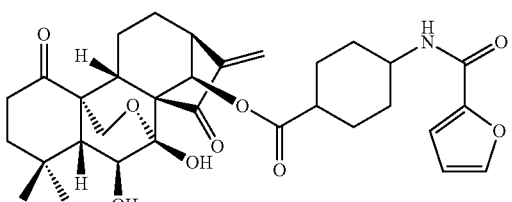

BS-OR-090

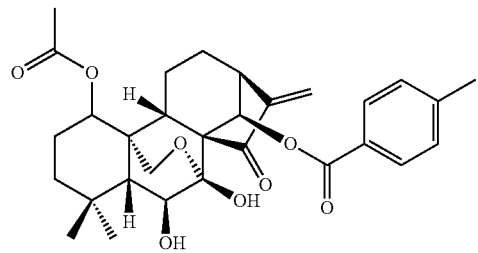

BS-OR-091

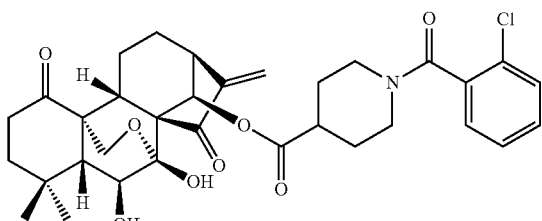

BS-OR-092

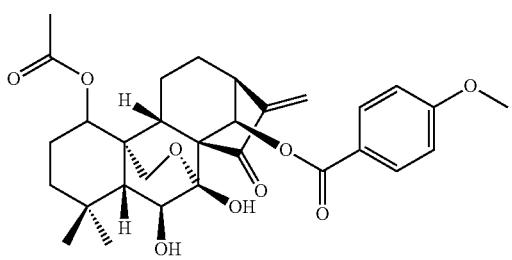

BS-OR-093

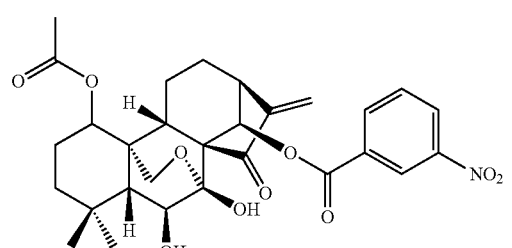

BS-OR-094

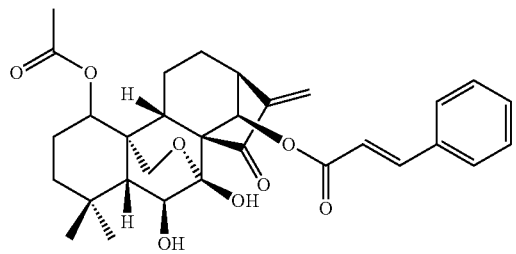

Some data for the compounds listed above are shown in the following table:

| Compound ID | Molecular formula | Molecular weight | Appearance | State | Total yield (%) |
|---|---|---|---|---|---|
| BS-OR-001 | $C_{27}H_{30}O_7$ | 466.5 | White | Powder | 65.32 |
| BS-OR-003 | $C_{27}H_{29}ClO_7$ | 501 | Colorless | Crystal | 62.48 |
| BS-OR-004 | $C_{28}H_{32}O_7$ | 480.6 | Colorless | Crystal | 63.9 |
| BS-OR-005 | $C_{28}H_{32}O_8$ | 496.6 | Colorless | Crystal | 44.73 |
| BS-OR-006 | $C_{27}H_{29}NO_9$ | 511.5 | Colorless | Crystal | 61.06 |
| BS-OR-007 | $C_{25}H_{28}O_7S$ | 472.6 | Colorless | Crystal | 56.8 |
| BS-OR-008 | $C_{25}H_{28}O_7$ | 480.6 | White | Solid | 58.93 |
| BS-OR-009 | $C_{28}H_{34}O_7$ | 494.6 | White | Powder | 51.83 |
| BS-OR-010 | $C_{27}H_{29}ClO_7$ | 501 | White | Powder | 67.45 |
| BS-OR-011 | $C_{26}H_{29}NO_7$ | 467.5 | Colorless | Crystal | 56.09 |
| BS-OR-012 | $C_{26}H_{29}NO_7$ | 467.5 | White | Powder | 53.25 |
| BS-OR-013 | $C_{26}H_{28}ClNO_7$ | 502 | Colorless | Crystal | 49.7 |
| BS-OR-014 | $C_{25}H_{29}NO_8$ | 471.5 | Colorless | Crystal | 42.6 |
| BS-OR-015 | $C_{29}H_{34}O_9$ | 526.6 | Colorless | Crystal | 61.77 |
| BS-OR-017 | $C_{24}H_{30}O_7$ | 430.5 | White | Powder | 53.25 |
| BS-OR-019 | $C_{29}H_{32}O_7$ | 492.6 | White | Crystal | 65.32 |
| BS-OR-020 | $C_{27}H_{29}BrO_7$ | 545.4 | White | Powder | 67.45 |
| BS-OR-025 | $C_{33}H_{41}NO_9S$ | 627.8 | White | Solid | 65.57 |
| BS-OR-026 | $C_{35}H_{45}NO_9S$ | 655.8 | White | Solid | 63.99 |
| BS-OR-027 | $C_{32}H_{38}ClNO_9S$ | 648.2 | White | Solid | 68.73 |
| BS-OR-029 | $C_{34}H_{43}NO_9S$ | 641.7 | White | Solid | 61.62 |
| BS-OR-032 | $C_{32}H_{39}NO_9S$ | 613.7 | White | Solid | 47.4 |
| BS-OR-034 | $C_{32}H_{38}N_2O_{11}S$ | 658.7 | Light yellow | Solid | 50.56 |
| BS-OR-035 | $C_{32}H_{38}N_2O_{11}S$ | 658.7 | Light yellow | Solid | 48.98 |
| BS-OR-037 | $C_{32}H_{38}N_2O_{11}S$ | 658.7 | White | Powder | 55.3 |
| BS-OR-038 | $C_{28}H_{39}NO_9S$ | 565.7 | White | Solid | 35.55 |
| BS-OR-039 | $C_{30}H_{43}NO_9S$ | 593.7 | White | Solid | 23.7 |
| BS-OR-040 | $C_{27}H_{37}NO_9S$ | 551.7 | White | Solid | 39.5 |
| BS-OR-041 | $C_{33}H_{38}F_3NO_9S$ | 681.7 | White | Solid | 52.14 |
| BS-OR-042 | $C_{33}H_{38}F_3NO_9S$ | 681.7 | White | Solid | 53.72 |
| BS-OR-043 | $C_{34}H_{43}NO_{10}$ | 625.7 | Light yellow | Solid | 45.03 |
| BS-OR-044 | $C_{32}H_{38}FNO_9S$ | 631.7 | Light yellow | Crystal | 53.72 |
| BS-OR-047 | $C_{31}H_{43}NO_8$ | 557.7 | White | Solid | 35.55 |
| BS-OR-048 | $C_{34}H_{41}NO_9$ | 607.7 | White | Solid | 49.77 |
| BS-OR-049 | $C_{34}H_{41}NO_8$ | 591.7 | White | Solid | 37.92 |
| BS-OR-050 | $C_{30}H_{39}NO_8$ | 541.6 | White | Solid | 58.46 |
| BS-OR-051 | $C_{32}H_{37}ClN_2O_8$ | 613.1 | White | Solid | 48.98 |
| BS-OR-052 | $C_{31}H_{37}NO_9$ | 567.6 | White | Solid | 44.24 |
| BS-OR-053 | $C_{31}H_{37}NO_8S$ | 583.7 | White | Powder | 55.3 |
| BS-OR-054 | $C_{33}H_{38}N_2O_{10}$ | 622.7 | White | Solid | 41.87 |
| BS-OR-055 | $C_{33}H_{39}NO_8$ | 577.7 | White | Crystal | 19.75 |
| BS-OR-056 | $C_{35}H_{43}NO_8$ | 605.7 | Colorless | Crystal | 47.4 |
| BS-OR-057 | $C_{31}H_{44}N_2O_8$ | 572.7 | Colorless | Crystal | 39.5 |
| BS-OR-058 | $C_{31}H_{44}N_2O_8$ | 572.7 | Yellow | Crystal | 52.14 |
| BS-OR-059 | $C_{33}H_{41}NO_9S$ | 627.7 | Colorless | Crystal | 41.87 |
| BS-OR-061 | $C_{33}H_{40}N_2O_{11}S$ | 672.7 | Colorless | Crystal | 44.24 |
| BS-OR-062 | $C_{31}H_{45}NO_9S$ | 607.8 | Colorless | Crystal | 45.82 |
| BS-OR-063 | $C_{33}H_{40}N_2O_{11}S$ | 672.7 | Colorless | Crystal | 48.98 |
| BS-OR-064 | $C_{34}H_{40}F_3NO_9S$ | 695.7 | Colorless | Crystal | 58.46 |
| BS-OR-065 | $C_{34}H_{40}F_3NO_9S$ | 695.7 | Colorless | Crystal | 53.72 |
| BS-OR-066 | $C_{33}H_{40}FNO_9S$ | 645.7 | Colorless | Crystal | 42.66 |
| BS-OR-067 | $C_{37}H_{49}NO_9S$ | 683.9 | Colorless | Crystal | 44.24 |

-continued

| Compound ID | Molecular formula | Molecular weight | Appearance | State | Total yield (%) |
|---|---|---|---|---|---|
| BS-OR-070 | $C_{34}H_{43}NO_9S$ | 641.8 | Colorless | Crystal | 55.3 |
| BS-OR-071 | $C_{35}H_{43}NO_9$ | 621.7 | Colorless | Crystal | 45.82 |
| BS-OR-072 | $C_{35}H_{43}NO_8$ | 605.7 | Colorless | Crystal | 52.14 |
| BS-OR-073 | $C_{35}H_{43}NO_8$ | 605.7 | Colorless | Crystal | 41.87 |
| BS-OR-074 | $C_{34}H_{40}N_2O_{10}$ | 636.7 | Colorless | Crystal | 48.98 |
| BS-OR-075 | $C_{32}H_{39}NO_8S$ | 597.7 | Colorless | Crystal | 58.46 |
| BS-OR-076 | $C_{34}H_{41}NO_8$ | 591.7 | Colorless | Crystal | 37.92 |
| BS-OR-077 | $C_{34}H_{40}FNO_8$ | 609.7 | Colorless | Crystal | 40.29 |
| BS-OR-078 | $C_{34}H_{40}ClNO_8$ | 626.1 | Colorless | Crystal | 45.82 |
| BS-OR-079 | $C_{34}H_{40}ClNO_8$ | 626.1 | Colorless | Crystal | 48.98 |
| BS-OR-080 | $C_{32}H_{45}NO_8$ | 571.7 | Colorless | Crystal | 58.46 |
| BS-OR-083 | $C_{33}H_{40}N_2O_8$ | 592.7 | Colorless | Crystal | 35.55 |
| BS-OR-086 | $C_{33}H_{40}ClNO_9S$ | 662.2 | Colorless | Crystal | 51.35 |
| BS-OR-087 | $C_{33}H_{40}N_2O_{11}S$ | 672.7 | Colorless | Crystal | 41.87 |
| BS-OR-088 | $C_{32}H_{39}NO_9$ | 581.7 | Colorless | Crystal | 45.82 |
| BS-OR-090 | $C_{30}H_{36}O_8$ | 524.6 | Colorless | Crystal | 16.33 |
| BS-OR-091 | $C_{30}H_{36}O_9$ | 540.6 | Colorless | Crystal | 16.80 |
| BS-OR-092 | $C_{29}H_{33}NO_{10}$ | 555.6 | Colorless | Crystal | 17.74 |
| BS-OR-093 | $C_{29}H_{33}ClO_{10}$ | 545 | Colorless | Crystal | 16.80 |
| BS-OR-094 | $C_{31}H_{36}O_8$ | 536.6 | Colorless | Crystal | 16.80 |
| BS-OR-095 | $C_{33}H_{38}ClNO_8$ | 612.1 | White | Solid | 31.6 |
| BS-OR-099 | $C_{35}H_{42}ClNO_9$ | 656.2 | White | Solid | 24.02 |

In another embodiment, the following compounds of formula (I) are particularly preferred by the present invention:

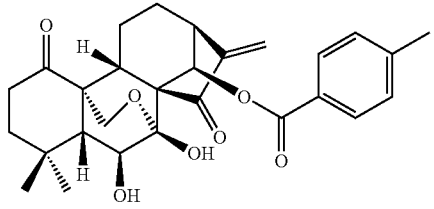

BS-OR-004

1-oxo-14-(4-methyl)benzoyloxy oridonin

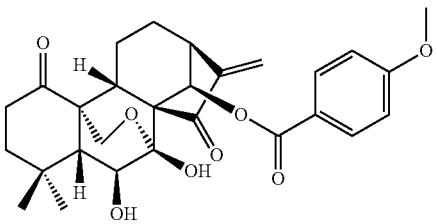

BS-OR-005

1-oxo-14-(4-methoxy)benzoyloxy oridonin

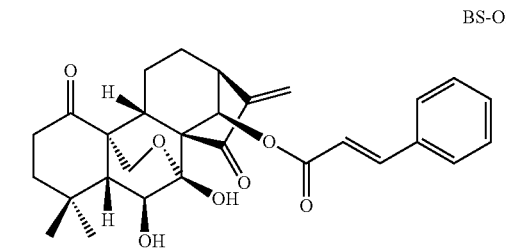

BS-OR-019

1-oxo-14-phenylacryloyloxy oridonin

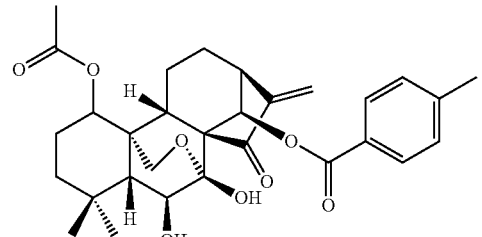

BS-OR-090

1-acetyl-14-(4-methyl)benzoyloxy oridonin

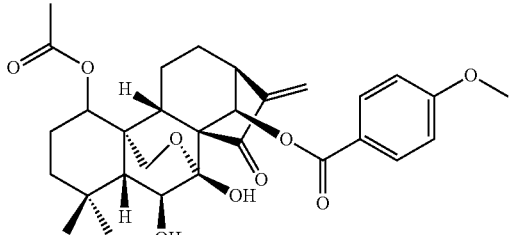

BS-OR-091

1-acetyl-14-(4-methoxy)benzoyloxy oridonin

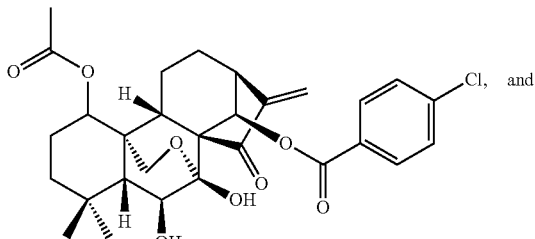

BS-OR-093

1-acetyl-14-parachlorobenzoyloxy oridonin

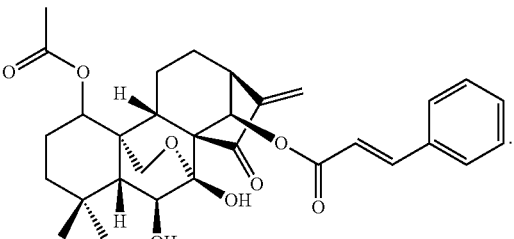

BS-OR-094

1-acetyl-14-phenylacryloyloxy oridonin

The present invention relates to salts, solvates, hydrates, adducts, complexes, polymorphs and prodrugs of the compounds of formula (I) of the present invention.

As used herein, the term "OR" refers to Oridonin.

As used herein, the term "alkyl" refers to a straight or branched alkyl containing designated number of carbon atoms. The alkyl can comprise 1-6, 1-5, 1-4 or 1-3 carbon atoms. Examples of alkyl include, but not limited to, methyl, ethyl, n-propyl, isopropyl, tert-butyl, n-pentyl, and n-hexyl.

The term "alkenyl" refers to a straight or branched alkenyl containing designated number of carbon atoms. The alkenyl can comprise 2-6, 2-5, 2-4 or 2-3 carbon atoms. Examples of alkenyl include, but not limited to, vinyl, allyl, butenyl, and isobutenyl.

The term "alkynyl" refers to a straight or branched alkynyl containing designated number of carbon atoms. The alkynyl can comprise 2-6, 2-5, 2-4 or 2-3 carbon atoms. Examples of alkynyl include, but not limited to, acetenyl and propinyl.

The term "$C_3$-$C_7$ cycloalkyl or cycloalkenyl" refers to a 3-7 membered monocyclic hydrocarbon radical having either a saturated or an unsaturated ring. $C_3$-$C_7$ cycloalkyl or cycloalkenyl can be cyclopropyl, cyclobutyl, cyclopentyl, cyclohexyl, cycloheptyl, cyclopropenyl and cyclohexenyl.

The term "aryl" refers to a monocyclic aryl or polycyclic aryl, fused or unfused, containing 6-14 (such as 6-12, 6-20) carbon atoms. In the case of polycyclic aryl, at least one ring is aromatic. Aryl can also be fused with a heterocyclyl. Examples of aryl include phenyl, biphenyl, naphthyl, 5,6,7,8-tetrahydronaphthyl, 2,3-dihydrobenzofuranyl, etc.

The term "heteroaryl" refers to an aromatic ring group having 1-4 heteroatoms (e.g. 1, 2, 3 or 4 heteroatoms) in the ring as ring atom(s). A heteroatom refers to nitrogen, oxygen or sulfur. A heteroaryl can be a monocyclic heteroaryl having 5-7 ring atoms or a bicyclic heteroaryl having 7-11 ring atoms. Said bicyclic heteroaryl should comprise at least one aromatic heterocycle, and the other ring(s) can be aromatic or non-aromatic, with or without a heteroatom. Examples of heteroaryl include such as pyrrolyl, pyrazolyl, imidazolyl, oxazolyl, pyridinyl, pyrimidinyl, furanyl, thiophenyl, isoxazolyl, indolyl, etc.

The term "heterocyclyl" refers to a non-aromatic cyclic group containing 1-4 heteroatoms (e.g. 1, 2, 3 or 4 heteroatoms) as ring members. A heteroatom refers to nitrogen, oxygen or sulfur. A heterocyclyl can be a monocyclic heterocyclyl having 4-8 ring atoms (such as 4-7 membered ring, 5-7 membered ring and 5-6 membered ring) or a bicyclic heterocyclyl having 7-11 ring atoms. A heterocyclyl can be either aromatic or non-aromatic. Examples of heterocyclyls include azacyclobutyl, pyrrolidinyl, pyrrolinyl, tetrahydrofuryl, dihydrofuryl, piperazinyl, piperidyl, morpholinyl, thiomorpholinyl, tetrahydropyranyl, tetrahydrothienyl, etc.

The term "halogen" refers to fluorine, chlorine, bromine or iodine.

The term "alkylamino" refers to an amino group substituted with one or two alkyls defined as above.

The term "alkoxy" includes alkyl-O-group, wherein the alkyl is defined as above.

The term "alkylthio" includes alkyl-S-group, wherein the alkyl is defined as above.

The term "pharmaceutically acceptable adducts and complexes of the compounds of formula (I)" refers to the product formed by a compound of the present invention with further combined small molecule or biological macromolecule via a non-chemical bond or non-covalent intermolecular force.

As used herein, the term "pharmaceutically acceptable salts of the compounds of formula (I)" can be exemplified as organic acid salts formed by an organic acid bearing a pharmaceutically acceptable anion. These organic acid salts include, but not limited to, tosylate, methanesulfonate, malate, acetate, citrate, malonate, tartrate, succinate, benzoate, ascorbate, lactate, α-ketoglutarate, and α-glycerophosphate. Suitable inorganic salts may also be formed, including but not limited to, hydrochloride, sulfate, nitrate, bicarbonate and carbonate, phosphate, hydrobromate, hydriodate salts and the like.

A pharmaceutically acceptable salt may be obtained using standard procedures well known in the art, for example by reacting a sufficient amount of alkaline compound with a suitable acid that provides a pharmaceutically acceptable anion.

As used herein, the term "polymorph" means a solid crystalline form of the compound of the present invention or a complex thereof. Various polymorphs of one same compound may exhibit different physical, chemical and/or spectroscopic properties. The different physical properties include, but not limited to, stability (e.g., thermal or light stability), compressibility and density (which are important for formulation and manufacture of the product), and dissolution rate (which may affect its bioavailability and absorbability). Differences in stability may result in a change in chemical reactivity (e.g., differential oxidation, such that a dosage form comprised of one polymorph discolors more rapidly than one comprised of another polymorph) or mechanical properties (e.g., in storage, crushed parts of the tablet of a kinetically favored polymorph is converted to a thermodynamically more stable polymorph) or both (e.g., tablets composed of one polymorph are more susceptible to breakdown at high humidity). Different physical properties of various polymorphs may affect their processing. For example, one polymorph may be more likely to form a solvate or may be more difficult to be filtered out or purified by washing than another one due to, for example, their different particle shapes or size distributions.

As used herein, the term "hydrate" means such a compound of the present invention or a salt thereof as further comprising a stoichiometric or non-stoichiometric amount of water bound via non-covalent intermolecular forces.

Unless otherwise indicated, the term "prodrug" used herein means a derivative of an inventive compound that, via hydrolyzation, oxidization, or other reactions under a biological condition (in vitro or in vivo), can provide a compound of this invention. A prodrug may only become active upon such a reaction under a biological condition, or may have activities in its unreacted form. Typically, a prodrug can be prepared using known methods, such as those described in *Burger's Medicinal Chemistry and Drug Discovery* (1995) 172-178, 949-982 (Manfred E. Wolff, 5$^{th}$ edition), *Prodrugs and Targeted Delivery* by J. Rautio (2011) 31-60 (Wiley-VCH, *Methods and Principles in Medicinal Chemistry*, Vol. 47), and *Fundamentals of Medicinal Chemistry* (2003) by G. Thomas, 195-200 (Wiley).

The "antitumor activity" as used herein refers to direct inhibition or killing of tumor cells or tissue. The examples of the present application partially determine the antitumor activity of the compounds of the present invention.

The terms "treatment," "treating," "treat," and the like used herein refer generally to obtaining a desired pharmacological and/or physiological effect. The effect may be prophylactic in terms of completely or partially preventing a disease or symptoms thereof and/or may be therapeutic in terms of partial or complete stabilization or cure of a disease and/or adverse effects caused by the disease. "Treatment" as used herein covers any treatment of a disease in a subject, including: (a) preventing the disease or symptoms from occurring in a subject who is predisposed to the disease or symptoms but has not yet been diagnosed as having it; (b) inhibiting the symptoms of a disease, i.e., arresting its development; or (c) relieving the symptoms of a disease, i.e., causing regression of the disease or symptoms.

The present invention also provides the method for preparing the compounds of the present invention, wherein 1) for the compound of formula (I) wherein W is oxo and L is direct bond or —(CH═CH)$_n$—, i.e., a compound of formula (I-1), wherein $R_1$ is defined as R in formula (I) and n is defined as for formula (I), said method comprises

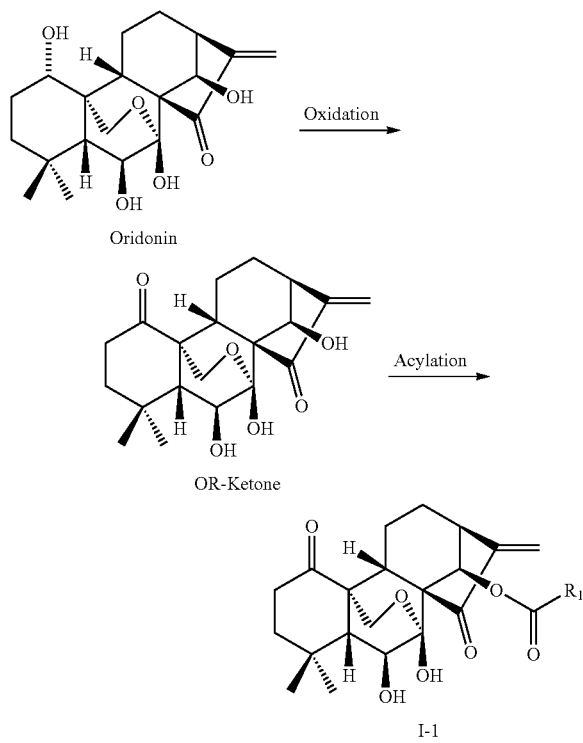

First, selectively oxidizing the 1-position hydroxyl of oridonin to produce a 1-oxo oridonin intermediate (OR-Ketone); then subjecting the intermediate to acylation with a corresponding organic acid, organic anhydride or organic acyl chloride in the presence of an alkali to produce a 1-oxo-14-acylated oridonin derivative of the formula (I-1);

2) for the compound of formula (I) wherein W is oxo and L is piperidinocarbonyl or piperidinosulfonyl, i.e., a compound of formula (I-2), wherein $R_2$ is —C(O)R or —C(O)S(O)$_2$R and the R is defined as in formula (I), said method comprises

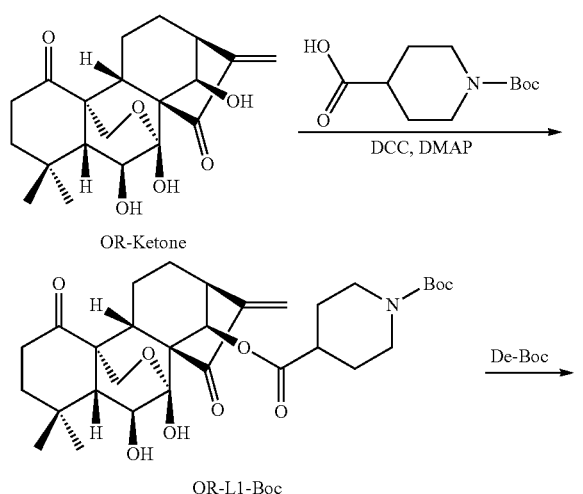

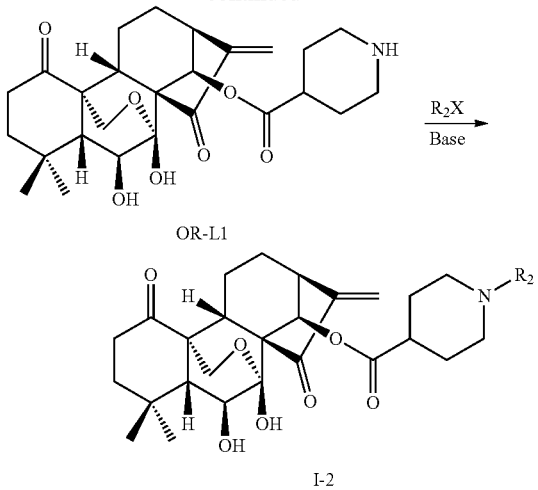

reacting the 1-oxo oridonin intermediate (OR-Ketone) with N-Boc-piperidyl-4-carboxylic acid in the presence of an alkali and a condensating agent to produce 1-oxo-14-(N-Boc 4-piperidylacyloxy)oridonin intermediate (OR-L1-Boc), which is treated with an acid to remove the Boc protecting group and produce an amine (ammonium salt) intermediate (OR-L1); reacting the amine (ammonium salt) intermediate with a corresponding organic acid, organic anhydride, organic acyl chloride, sulfonyl chloride in the presence of an alkali to produce a 1-oxo-14-(piperidylacyloxy)oridonin derivative of formula (I-2);

3) for the compound of formula (I) wherein W is oxo and L is cyclohexylaminocarbonyl or cyclohexylaminosulfonyl, i.e., a compound of formula (I-3), wherein $R_3$ is —C(O)R or —C(O)S(O)$_2$R and the R is defined as in formula (I), said method comprises

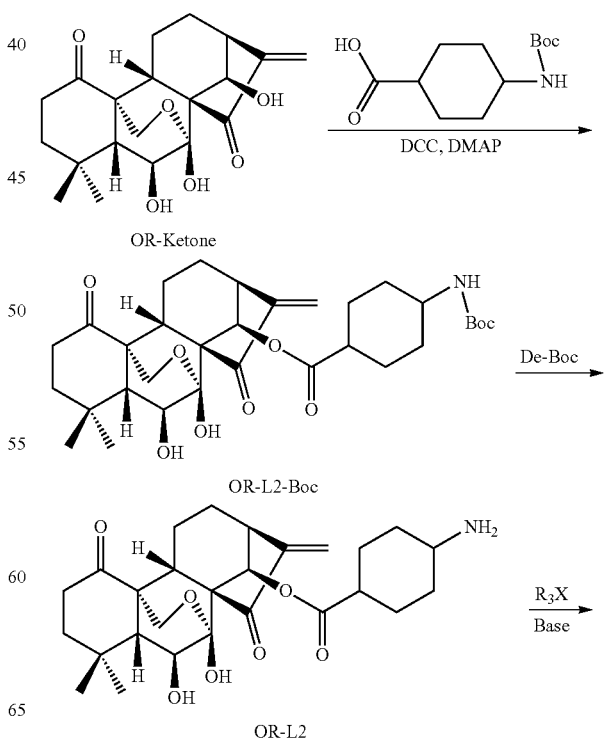

-continued

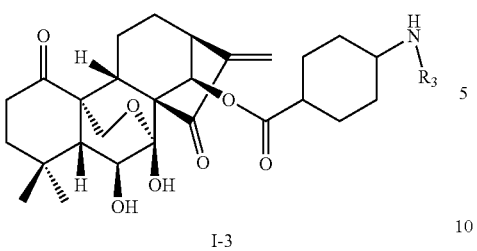
I-3 reacting the 1-oxo oridonin intermediate (OR-Ketone) with 1-(N-Boc)amino-4-cyclohexyl carboxylic acid in the presence of an alkali and a coupling agent to produce 1-oxo-14-(1-(N-Boc amino)-4-cyclohexylacyloxy)oridonin intermediate (OR-L2-Boc), which is treated with an acid to remove the Boc protecting group thus producing an amine (ammonium salt) intermediate (OR-L2); reacting the amine (ammonium salt) intermediate with a corresponding organic acid, organic anhydride, organic acyl chloride or sulfonyl chloride in the presence of an alkali to produce a 1-oxo-14-(1-(amino)cyclohexyl-4-acyloxy)oridonin derivative of formula (I-3);

4) for the compound of formula (I) wherein W is —O(CO)R' and L is direct bond or —(CH═CH)$_n$—, i.e., a compound of formula (I-4), wherein $R_1$ is defined as R in formula (I), $R_4$ is defined as R' in formula (I), and n is defined as in formula (I), said method comprises

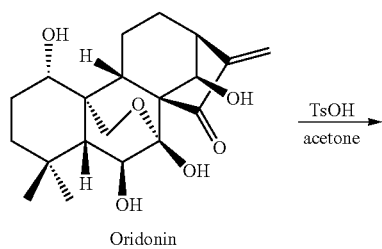
Oridonin

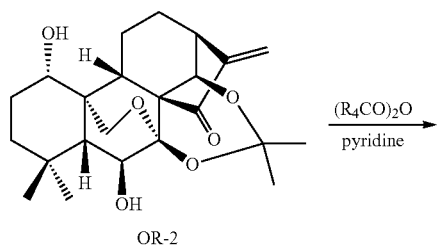
OR-2

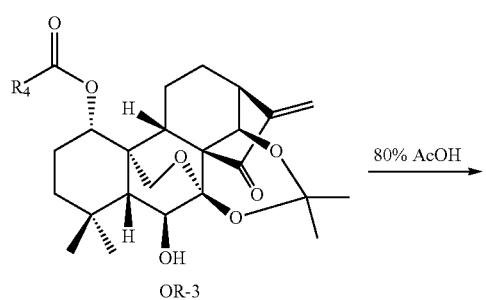
OR-3

-continued

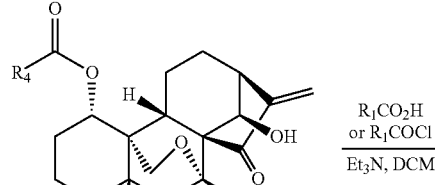
OR-4

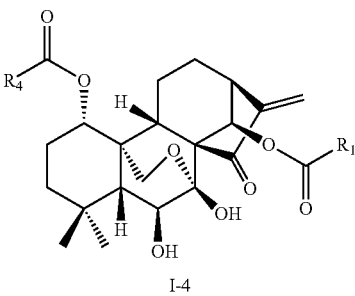
I-4 first subjecting the 7-,14-position hydroxyls to acetal protection to produce OR-2; then subjecting the 1-position hydroxyl to acylation to produce an intermediate OR-3; treating OR-3 with an acid for deprotection to produce an intermediate OR-4; subjecting OR-4 to acylation to produce 1,14-diacylated oridonin derivative (I-4);

5) for the compound of formula (I) wherein W is —O(CO)R' and L is piperidinocarbonyl or piperidinosulfonyl, wherein R' is defined as in formula (I), said method comprises carrying out the method according to 2) above, except that OR-Ketone is replaced with OR-4 in 4) above; or 6) for the compound of formula (I) wherein W is —O(CO)R' and L is cyclohexylaminocarbonyl or cyclohexylaminosulfonyl, wherein R' is defined as in formula (I), said method comprises
carrying out the method according to 3) above, except that OR-Ketone is replaced with OR-4 in 4) above.

For example, the compound of formula (I) of the present invention can be prepared according to the following process:

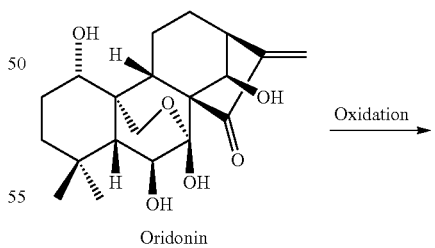
Oridonin

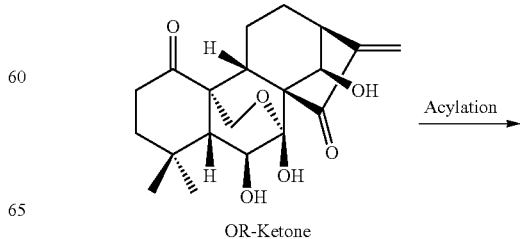
OR-Ketone

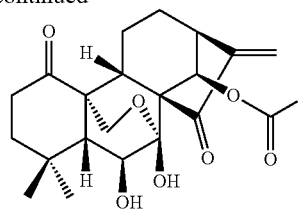

I-1

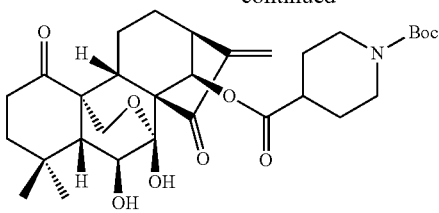

OR-L1-Boc

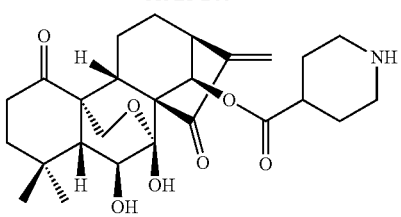

OR-L1

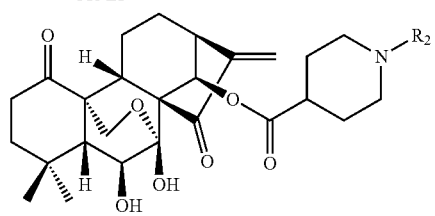

I-2

The 1-oxo-14-acylated oridonin derivative (I-1) of the present invention can be prepared in a two-step reaction as shown above. The oridonin extracted from natural medicine is selectively oxidized on the hydroxyl group at 1-position, producing 1-oxo oridonin intermediate (OR-Ketone). The oxidation may be carried out with potassium permanganate or Jone's oxidizing agent. The temperature can be at room temperature. During the oxidation of 1-position hydroxyl, other hydroxyls need no particular protection. The reaction is typically carried out in a solvent. The solvent used includes, but not limited to, organic polar solvents, such as acetone, dichloromethane (DCM), tetrahydrofuran (THF), N,N-dimethylformamide (DMF), dimethyl sulfoxide (DMSO), etc.

The 1-oxo oridonin intermediate (OR-Ketone) reacts at its 14-position hydroxyl with an organic acid, an organic acyl halide, or an organic anhydrideto produce a 1-oxo-14-acylated oridonin derivative (I-1). This reaction is typically carried out in the presence of an alkali and a condensating agent. The alkali here can be an organic alkali or an inorganic alkali, such as 4-dimethylaminopyridine, triethylamine and potassium carbonate.

The condensating agent used for acylation can be 1,3-dicyclohexylcarbodiimide, 2-(7-azabenzotriazol-1-yl)-N,N,N',N'-tetramethyluronium hexafluorophosphate (HATU), o-(benzotriazol-1-yl)-N,N,N',N'-tetramethyluronium hexafluoroborate (HBTU), o-(benzotriazol-1-yloxy)tris(dimethylamino)phosphonium hexafluorophosphate (BOP), o-(benzotriazol-1-yl)-N,N,N',N'-tetramethyluronium hexafluoroborate (TBTU).

The acylation reagent used for the acylation can be a corresponding organic acid, organic acyl halide or organic anhydride. The sulfonylation reagent used for the sulfonylation can be a corresponding organic sulfonyl halide.

The acylation typically takes place in a solvent. The choice of the solvent depends on the polarity and solubility of the starting materials. The solvent used includes, but not limited to, organic polar solvents, such as dichloromethane (DCM), tetrahydrofuran (THF), N,N-dimethylformamide (DMF), dimethylsulfoxide (DMSO), etc.

The temperature of the acylation depends on the reactivity of the substrate. The reaction typically takes place at a low or room temperature.

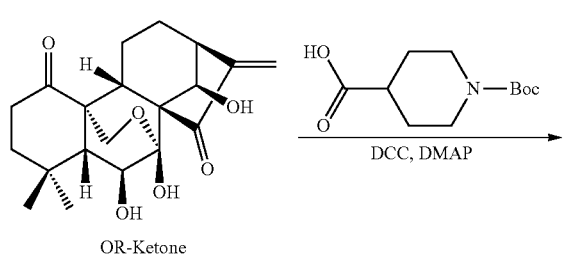

OR-Ketone

The 1-oxo-oridonin intermediate (OR-Ketone) is reacted with N-Boc-piperidyl-4-carboxylic acid in the presence of an alkali and a condensating agent to produce 1-oxo-14-(N-Boc 4-piperidylacyloxy)oridonin intermediate (OR-L1-Boc). The acylation conditions above (reaction temperature and duration, the condensating agent and the alkali) also apply to this reaction.

The 1-oxo-14-(N-Boc 4-piperidylacyloxy) oridonin intermediate (OR-L1-Boc) is treated with an acid to remove the Boc protecting group and produce an amine (ammonium salt) intermediate (OR-L1). The acid used can be an organic or an inorganic acid, such as trifluoroacetic acid or hydrochloric acid. The reaction product is typically a corresponding ammonium salt, and the reaction yield is typically quantitative.

The 1-oxo-14-(4-piperidylacyloxy)oridonin intermediate (OR-L1) amine (ammonium salt) is reacted with a corresponding halohydrocarbon, organic acid, organic anhydride, organic acyl chloride or organic sulfonyl chloride, in the presence of an alkali, to produce a 1-oxo-14-(piperidylacyloxy)oridonin derivative of formula (I-2), wherein $R_2$ is defined the same as in the formula (I-2) above.

The acylation of the (OR-L1) amine (ammonium salt) intermediate typically takes place in the presence of a condensating agent. The condensating agent here can be, but not limited to, organic condensating agents, such as 2-(7-azabenzotriazol-1-yl)-N,N,N',N'-tetramethyluronium hexafluorophosphate (HATU), o-(benzotriazol-1-yl)-N,N,N',N'-tetramethyluronium hexafluoroborate (HBTU), o-(benzotriazol-1-yloxy)tris(dimethylamino)phosphonium hexafluorophosphate (BOP), and o-(benzotriazol-1-yl)-N,N,N',N'-tetramethyluronium hexafluoroborate (TBTU).

The acylation of the (OR-L1) amine (ammonium salt) intermediate must take place in the presence of an alkali, which is for neutralizing the acid in the ammonium salt to give free amine and participate in the condensation-acylation of this amine intermediate with an organic acid, anhydride or acyl chloride. The alkali here can be, but not limited to, organic alkali, such as N,N-diisopropylethylamine (DIPEA), triethylamine (TEA), pyridine, and 4-dimethylaminopyridine (DMAP).

The acylation of the amine can take place either in the presence or in the absence of a solvent. The solvent used includes, but not limited to, organic polar solvents, such as dichloromethane (DCM), tetrahydrofuran (THF), N,N-dimethylformamide (DMF), dimethylsulfoxide (DMSO), etc.

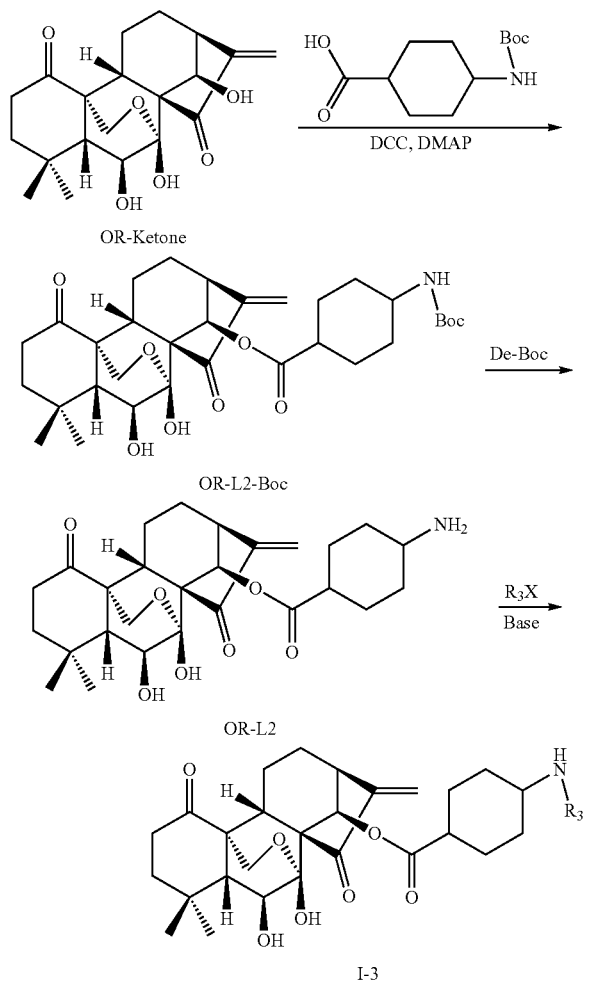

The 1-oxo oridonin intermediate (OR-Ketone) is reacted with 1-(N-Boc)amino-4-cyclohexyl carboxylic acid in the presence of an alkali and a coupling agent to produce 1-oxo-14-(1-(N-Boc amino)-4-cyclohexylacyloxy)oridonin intermediate (OR-L2-Boc). This intermediate is treated with an acid to remove the Boc protecting group and produce an amine (ammonium salt) intermediate (OR-L2). This amine (ammonium salt) intermediate is reacted with a corresponding organic acid, organic anhydride, organic acyl chloride or sulfonyl chloride in the presence of an alkali to produce a 1-oxo-14-(1-(amino)cyclohexyl-4-acyloxy)oridonin derivative of formula (I-3), wherein $R_3$ is defined the same as in the formula (I-3) above.

The preparation of the 1-oxo-14-(1-(amino)cyclohexyl-4-acyloxy)oridonin derivative of formula (I-3) and corresponding intermediates thereof is essentially analogous to the preparation of the 1-oxo-14-(piperidylacyloxy)oridonin derivative of formula (I-2) with respect to reaction temperature, solvents, reagents, operation, and the like.

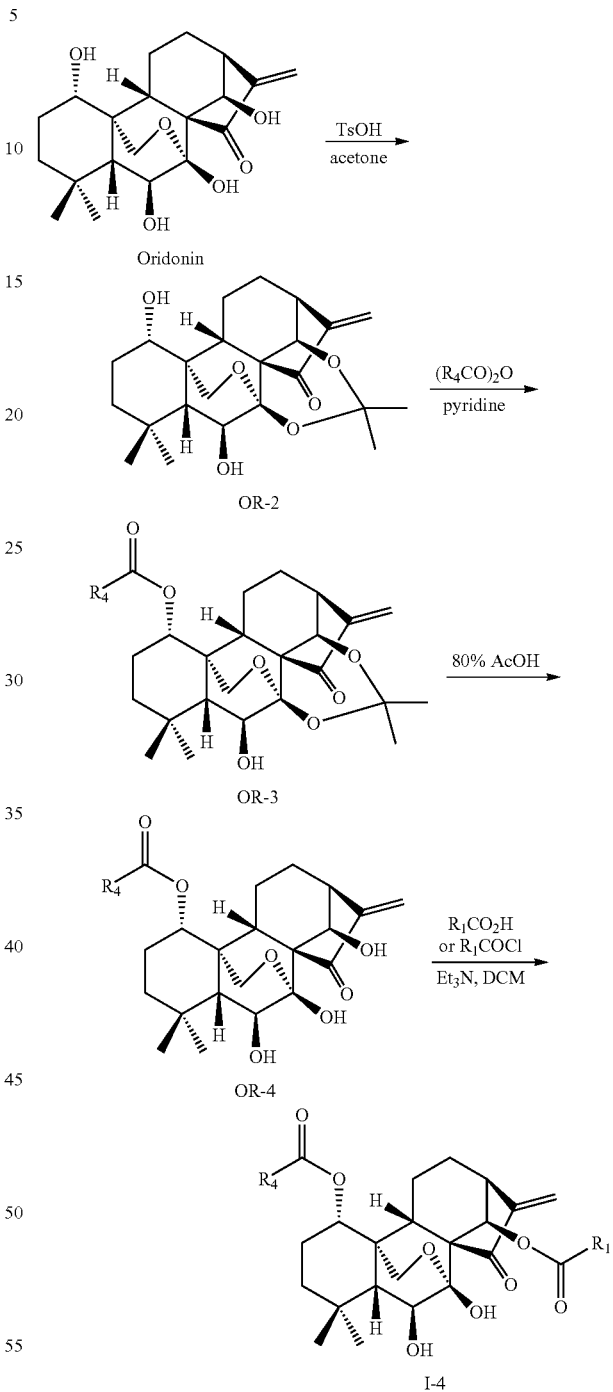

The 1,14-diacylated oridonin derivative (I-4) can be prepared in a four-step reaction as shown above. First, the hydroxyl groups at 7-,14-position are subjected to acetal protection by conventional methods to produce OR-2. The protection reagent can be a corresponding ketone or aldehyde, and the protection reaction needs to take place in the presence of an acid in a catalytic amount.

The 1-position hydroxyl of the intermediate OR-2 can be acylated by conventional methods to produce an intermediate OR-3. The acylation reagent can be an organic acid, organic anhydride, or organic acyl chloride. The acylation needs to take place in the presence of a solvent and an alkali.

The intermediate OR-3 is treated with an acid for deprotection to produce an intermediate OR-4. The deprotection reagent can be an organic acid, such as 80% acetic acid. The reaction temperature depends on the reactivity of the substrate.

The intermediate OR-4 is subjected to acylation to produce 1,14-diacylated oridonin derivative (I-4). The acylation of OR-4 is essentially analogous to the preparation of the 1-oxo-14-acylated oridonin derivative of formula (I-1) with respect to reaction temperature, solvents, reagents, operation, and the like, wherein $R_1$ and $R_4$ are defined the same as in the formula (I-4) above.

Conventional chemical conversion processes may be used to practice this invention. One skilled person in the art can determine suitable chemical agents, solvents, protecting groups, and reaction conditions for these chemical conversions. Relevant information are described, for example, in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Protecting groups refer to the groups that, upon being attached to an active moiety (e.g., a hydroxyl or amino group), prevent the moiety from interference in a subsequent reaction and, after the reaction, can be removed through a conventional method. Examples of protecting grouped for hydroxyl include, but not limited to, alkyl, benzyl, allyl, trityl (also known as triphenylmethyl), acyl (e.g., benzoyl, acetyl, or HOOC—X"—CO—, wherein X" is alkylidene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of protecting groups for amino include, but not limited to, alkoxycarbonyl, alkanoyl, aryloxycarbonyl, arylsubstituted alkyl and the like. Protecting groups for hydroxyl and amino have been discussed in T. W. Greene and P. G. M. Wuts, Protective Groups in Organic Synthesis, 2nd. Ed., John Wiley and Sons (1991). All hydroxyl and amino protecting groups can be removed by a conventional method after the reaction.

The present invention also provides a pharmaceutical composition comprising the compound of formula (I) of the present invention.

The present invention provides a pharmaceutical composition which comprises at least one compound of formula (I) of the present invention as defined above and optionally a pharmaceutically acceptable excipient.

The methods for preparing various pharmaceutical compositions having a given amount of active components are known or will be apparent to those skilled in the art in light of this disclosure. As described in REMINGTON'S PHARMACEUTICAL SCIENCES, Martin, E. W., ed., Mack Publishing Company, 19th ed. (1995), the methods for preparing such pharmaceutical compositions include incorporation of other suitable pharmaceutical excipients, carriers, diluents, etc.

The pharmaceutical preparations of the present invention are produced by known methods, including mixing, dissolving, or freeze drying processes.

The compounds of the present invention may be formulated into a pharmaceutical composition and administered to a subject in a route suitable for the selected administration manner, e.g., orally, gastrointestinal infusion, intravenous injection, or intramuscular and subcutaneous injection.

Thus, the present compounds may be systemically administered, e.g., orally administered, in conjugation with a pharmaceutically acceptable carrier such as an inert diluent or an edible carrier. They may be enclosed in hard or soft gelatin capsules, or may be compressed into tablets. For therapeutic oral administration, the active compound may be combined with one or more excipients and may be taken in a form of ingestible tablet, buccal tablet, troche, capsule, elixir, suspension, syrup, wafer, and the like. Such a composition or preparation should contain at least 0.1% of the active compound. Of course, the proportion of active compound in the compositions and preparations may vary and may be from about 1% to about 99% by weight of a given unit dosage form. In a therapeutically useful composition, the active compound is present in an amount such that an effective dosage level is achieved.

A tablet, troche, pill, capsule and the like may also comprise a binder, such as gum tragacanth, arabic gum, corn starch or gelatin; an excipient such as calcium dihydrogenphosphate; a disintegrating agent such as corn starch, potato starch, alginic acid and the like; a lubricant such as magnesium stearate; and a sweetening agent such as sucrose, fructose, lactose or aspartame; or a flavoring agent such as peppermint, wintergreen oil, or cherry flavor. In case the unit dosage form is a capsule, it may comprise, in addition to the above materials, a liquid vehicle such as a vegetable oil or polyethylene glycol. Various other materials may be present as coatings or otherwise modify the physical form of the solid unit dosage form. For instance, a tablet, pill, or capsule may be coated with gelatin, wax, shellac or sugar, etc. A syrup or elixir may contain an active compound, a sweetening agent such as sucrose or fructose, a preservative such as methylparaben or propylparaben, a dye and a flavoring agent (such as cherry or orange flavor). Of course, any materials used in preparing unit dosage forms should be pharmaceutically acceptable and substantially non-toxic in the amounts employed. In addition, the active compound may be incorporated into a sustained-release preparation or in a device.

The active compound may also be administered intravenously or intraperitoneally by infusion or injection. An aqueous solution of the active compound or its salt may be prepared, optionally mixed with a nontoxic surfactant. Also can be prepared is dispersion in glycerol, liquid polyethylene glycol, triacetin, or a mixture thereof, or in an oil. Under ordinary storage and use conditions, these preparations contain a preservative to prevent the growth of microorganisms.

The pharmaceutical dosage forms suitable for injection or infusion may include a sterile aqueous solution, a dispersion or a sterile powder comprising active ingredient (optionally encapsulated in liposomes), which are adapted for an extemporaneous preparation of a sterile injectable or infusible solution or dispersion. In all cases, the final dosage form must be sterile and stable liquids under the manufacture and storage conditions. The liquid carrier or vehicle may be a solvent or a liquid dispersion medium comprising, for example, water, ethanol, a polyol (for example, glycerol, propylene glycol, liquid polyethylene glycol, and the like), a vegetable oil, a nontoxic glyceryl ester, and a suitable mixture thereof. A proper fluidity can be maintained, for example, by formation of liposomes, by maintenance of the required particle size in the case of dispersion or by the use of a surfactant. The prevention of microorganism can be achieved by various antibacterial and antifungal agents, such as parabens, chlorobutanol, phenol, sorbic acid, thimerosal, and the like. In many cases, an isotonic agent is preferably comprised, such as sugar, buffer agent or sodium chloride. Prolonged absorption of an injectable composition can be obtained by the use of a composition of the agents for delaying absorption, for example, aluminum monostearate and gelatin.

An injectable sterile solution is prepared by combining a required amount of the active compound in a suitable solvent with various additional desired components as listed above, followed by filtration and sterilization. For sterile powder used to prepare an injectable sterile solution, the preferred preparation process is vacuum drying and freeze drying techniques, which yield a powder of the active ingredient plus any additional desired ingredient present in the previous filtered sterile solution.

Useful solid carriers include finely divided solids such as talc, clay, microcrystalline cellulose, silica, alumina and the like. Useful liquid carriers include water, ethanol or ethylene glycol or a water-ethanol/ethylene glycol mixture, in which the compound of the present invention can be dissolved or dispersed at an effective content, optionally with the aid of a non-toxic surfactant. An adjuvant (such as a flavour) and additional antimicrobial agent can be added to optimize the properties for a given application.

Thickening agent (such as a synthetic polymer, a fatty acid, a fatty acid salt and ester, a fatty alcohol, a modified cellulose or a modified inorganic material) can also be used with a liquid carrier to form a spreadable paste, gel, ointment, soap and the like for applying directly to the skin of a user.

The amount of the compound or an active salt or derivative thereof required for a treatment varies depending not only on the selected particular salt but also on the administration route, the nature of the condition to be treated and the age and condition of the subject, and will be ultimately determined at the discretion of the attendant physician or clinician.

The above formulations can be present in a unit dosage form which is a physically discrete unit containing a unit dosage, which is suitable for administering to a human or other mammalians. The unit dosage form may be a capsule or a tablet, or a plurality of capsules or tablets. Depending upon the intended particular therapy, the amount of the active ingredient in a unit dosage form can be varied or adjusted in the range of about 0.1 mg to about 1,000 mg or more.

The present invention also provides the use of a compound according to the present invention or a pharmaceutical composition comprising the compound of the present invention in manufacture of a medicament, especially an antitumor medicament. Accordingly, the present invention provides a method for treating a subject suffering from tumor, comprising administering to the subject in need thereof a therapeutically effective amount of at least one compound of the present invention. The 1-oxo/acylated-14-acylated oridonin derivatives of the present invention or a pharmaceutically acceptable salt thereof can be used, for example, for the treatment of leukemia, multiple myeloma, lymphoma, liver cancer, gastric cancer, breast cancer, cholangiocellular carcinoma, pancreatic cancer, lung cancer, colorectal cancer, osteosarcoma, melanoma, cervical cancer, glioma, nasopharyngeal carcinoma, laryngeal carcinoma, esophageal cancer, middle ear tumor, prostate cancer, etc.

The present invention will be explained in more detailed by the following examples. However, it should be understood that the following examples are intended for illustration only but not to limit the scope of the present invention in any way.

The raw chemicals used in the following examples are commercially available or may be obtained by a synthesis method known in the art.

Example 1: The Synthesis of Compound BS-OR-003

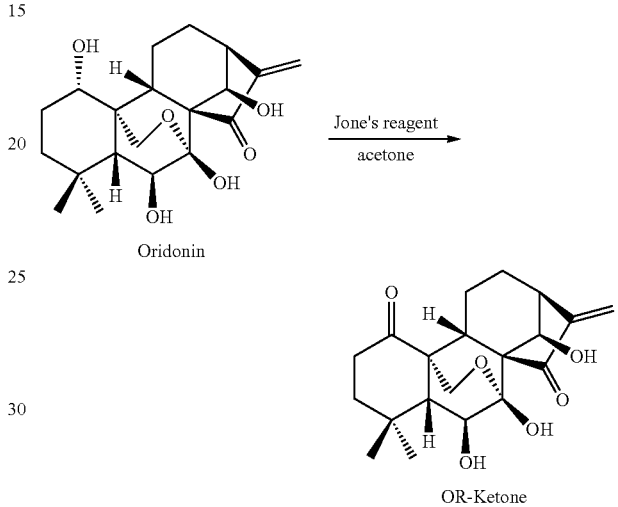

Chromium trioxide (240 mg, 2.4 mmol) was dissolved in 2 mL water. 0.22 mL concentrated sulfuric acid was added at 0° C., followed by 3 mL of water. The mixture was stirred to form Jone's reagent for later use.

To oridonin (730 mg, 2 mmol) was added 20 mL acetone to form a suspension. The Jone's reagent (2.4 mmol of chromium trioxide) was slowly added dropwise under ice-bath conditions. After being stirred for 3 hours, the reaction solution was returned to room temperature. The reaction was quenched with isopropanol and the acetone solvent was removed. The crude product was extracted three times with dichloromethane (30 mL*3). The organic phase was washed with saturated sodium bicarbonate followed by saturated saline solution, dried and rotavapped. The resulted crude product was separated via silica gel column (petroleum ether:ethyl acetate=1:1) to give 1-oxo oridonin (520 mg, 71% yield) as a white powder. Meanwhile, 100 mg of oridonin was recovered with the recovery rate being 14%.

MS (m/z): 363 [M+H]$^+$, 385 [M+Na]$^+$.

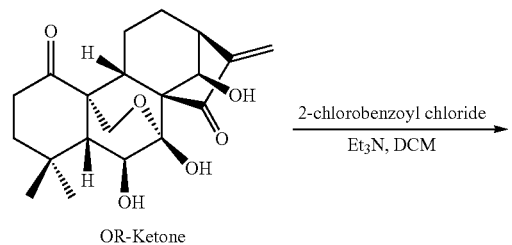

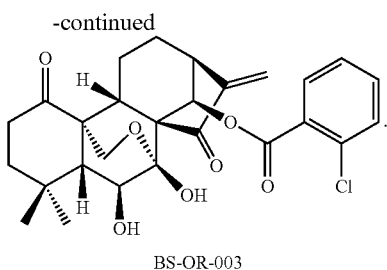

BS-OR-003

The 1-oxo oridonin (36.5 mg, 0.1 mmol) and 2-chlorobenzoyl chloride (87 mg, 0.5 mmol) were dissolved in dry dichloromethane (2 mL), followed by dropwise addition of triethylamine (50.5 mg, 0.5 mmol) at 0° C. The reaction was warmed up to room temperature and stirred for 1 hour. When the reaction was completed, the mixture was diluted with 30 mL dichloromethane, washed twice with ice-cold 5% aqueous sodium carbonate solution, and then washed with water and saturated saline solution. The organic phase was dried and rotavapped. The resulted crude product was separated via silica gel column (ethyl acetate:petroleum ether=1:2) to finally give BS-OR-003 (41.8 mg, 88% yield) as a colorless crystal.

MS (m/z): 501 [M+H]$^+$, 523 [M+Na]$^+$.

$^1$H NMR (300 MHz, CDCl$_3$): δ 7.77-7.79 (m, 1H, H-benzene), 7.39-7.41 (m, 2H, H-benzene), 7.26-7.29 (m, 1H, H-benzene), 6.28 (s, 1H, H-17), 6.14 (s, 1H, H-14), 5.65 (s, 1H, H-17), 5.39 (d, 1H, J=15.5 Hz, OH-6), 4.36 (d, 1H, J=14.3 Hz), 4.06 (d, 1H, J=12.3 Hz), 4.0 (s, 1H), 3.75-3.82 (m, 1H), 3.31 (d, 1H, J=12.4 Hz), 2.30-2.61 (m, 5H), 1.78-1.99 (m, 3H), 1.55-1.73 (m, 2H), 1.20 (s, 3H, CH$_3$-18), 1.01 (s, 3H, CH$_3$-19).

Compound BS-OR-001 was prepared by reacting the compound 1-oxo oridonin with benzoyl chloride according to the process for preparing BS-OR-003 using the same reagents:

MS (m/z): 467 [M+H]$^+$, 489 [M+Na]$^+$

Compound BS-OR-004 was prepared by reacting the compound 1-oxo oridonin with p-methylbenzoyl chloride according to the process for preparing BS-OR-003 using the same reagents:

MS (m/z): 481 [M+H]$^+$, 503 [M+Na]$^+$.

$^1$H NMR (300 MHz, CDCl$_3$): δ 7.80 (d, 2H, J=11.0 Hz, H-benzene), 7.20 (d, 2H, J=11.3 Hz, H-benzene), 6.28 (s, 1H, H-17), 6.06 (s, 1H, H-14), 5.61 (s, 1H, H-17), 5.43 (d, 1H, J=15.4 Hz, OH-6), 4.34 (d, 1H, J=14.3 Hz), 4.16 (s, 1H), 4.05 (d, 1H, J=14.3 Hz), 3.77-3.84 (m, 1H), 3.28 (d, 1H, J=12.4 Hz), 2.36 (s, 3H, H—CH$_3$), 2.27-2.46 (m, 5H), 1.77-1.99 (m, 3H), 1.55-1.76 (m, 2H), 1.21 (s, 3H, CH$_3$-18), 1.01 (s, 3H, CH$_3$-19).

Compound BS-OR-005 was prepared by reacting the compound 1-oxo oridonin with p-methoxybenzoyl chloride according to the process for preparing BS-OR-003 using the same reagents:

MS (m/z): 497 [M+H]$^+$, 519 [M+Na]$^+$.

$^1$H NMR (300 MHz, CDCl$_3$): δ 7.84-7.88 (m, 2H, H-benzene), 6.86-6.89 (m, 2H, H-benzene), 6.28 (s, 1H, H-17), 6.03 (s, 1H, H-14), 5.61 (s, 1H, H-17), 5.44 (d, 1H, J=15.4 Hz, OH-6), 4.34 (d, 1H, J=14.2 Hz), 4.19 (s, 1H), 4.03-4.07 (m, 1H), 3.83 (s, 3H, H—CH$_3$), 3.77-3.84 (m, 1H), 3.28-3.29 (m, 1H), 2.26-2.65 (m, 5H), 1.89-2.09 (m, 3H), 1.56-1.79 (m, 2H), 1.21 (s, 3H, CH$_3$-18), 1.01 (s, 3H, CH$_3$-19).

Compound BS-OR-006 was prepared by reacting the compound 1-oxo oridonin with 3-nitrobenzoyl chloride according to the process for preparing BS-OR-003 using the same reagents:

MS (m/z): 512 [M+H]$^+$, 534 [M+Na]$^+$.

Compound BS-OR-007 was prepared by reacting the compound 1-oxo oridonin with 2-thiophene formic acid according to the process for preparing BS-OR-003 using the same reagents:

MS (m/z): 473 [M+H]$^+$, 495 [M+Na]$^+$.

Compound BS-OR-008 was prepared by reacting the compound 1-oxo oridonin with 3-methylbenzoyl chloride according to the process for preparing BS-OR-003 using the same reagents:

MS (m/z): 481 [M+H]$^+$, 503 [M+Na]$^+$.

Compound BS-OR-009 was prepared by reacting the compound 1-oxo oridonin with phenylpropionyl chloride according to the process for preparing BS-OR-003 using the same reagents:

MS (m/z): 495 [M+H]$^+$, 517 [M+Na]$^+$.

Compound BS-OR-010 was prepared by reacting the compound 1-oxo oridonin with p-chlorobenzoyl chloride according to the process for preparing BS-OR-003 using the same reagents:

MS (m/z): 501 [M+H]$^+$, 523 [M+Na]$^+$, 539 [M+H]$^+$; HPLC: retention time 5.507 min (99.85%).

$^1$H NMR (300 MHz, CDCl$_3$): δ 7.87 (d, 2H, J=8.7 Hz, H-benzene), 7.38 (d, 2H, J=8.7 Hz, H-benzene), 6.30 (s, 1H, H-17), 6.12 (s, 1H, H-14), 5.64 (s, 1H, H-17), 5.44 (d, 1H, J=12 Hz, OH-6), 4.37 (d, 1H, J=10.5 Hz), 4.06 (d, 1H, J=10.5 Hz), 3.80 (m, 1H), 3.25 (d, 1H, J=9.6 Hz), 1.20 (s, 3H, CH$_3$-18), 1.00 (s, 3H, CH$_3$-19).

Compound BS-OR-019 was prepared by reacting the compound 1-oxo oridonin with phenylacryloyl chloride according to the process for preparing BS-OR-003 using the same reagents:

MS (m/z): 493 [M+H]$^+$, 515 [M+Na]$^+$, 531 [M+H]$^+$; HPLC: retention time 5.372 min (100.00%).

Compound BS-OR-020 was prepared by reacting the compound 1-oxo oridonin with o-bromobenzoyl chloride using the same reagents as above according to the process for preparing BS-OR-003:

MS (m/z): 545 [M+H]$^+$, 567 [M+Na]$^+$, 583 [M+H]$^+$; HPLC: retention time 6.471 min (98.05%).

$^1$H NMR (300 MHz, CDCl$_3$): δ 7.76 (m, 1H, H-benzene), 7.63 (m, 1H, H-benzene), 7.34 (m, 2H, H-benzene), 6.28 (s, 1H, H-17), 6.14 (s, 1H, H-14), 5.65 (s, 1H, H-17), 5.41 (d, 1H, J=8.7 Hz, OH-6), 4.37 (d, 1H, J=10.5 Hz), 4.08 (dd, 1H, J=10.5 Hz, 1.5 Hz), 3.97 (s, 1H), 3.77 (m, 1H), 3.33 (d, 1H, J=9.9 Hz), 1.20 (s, 3H, CH$_3$-18), 1.01 (s, 3H, CH$_3$-19).

Example 2: The Synthesis of Compound BS-OR-013

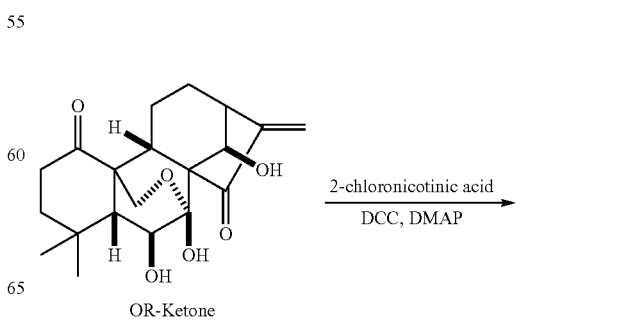

OR-Ketone

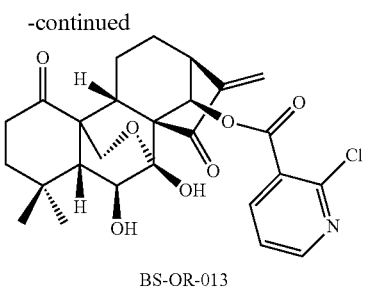

BS-OR-013 wherein DCC is 1,3-dicyclohexylcarbodiimine; and DMAP is 4-dimethylaminopyridine.

1,3-Dicyclohexylcarbodiimine (31 mg, 0.15 mmol) was dissolved in 2 mL dichloromethane, to which 1-oxo oridonin (36.5 mg, 0.1 mmol) was added at 0° C. After the mixture was stirred for 0.5 hr, 2-chloronicotinic acid (23.6 mg, 0.15 mmol) and 4-dimethylaminopyridine (10 mg, catalytic amount) were added. The mixture was stirred overnight at room temperature and the solvent was rotavapped off. The resulted crude product was separated via silica gel column (ethyl acetate:petroleum ether=1:1) to finally give BS-OR-013 (35.5 mg, 70% yield) as a colorless crystal.

MS (m/z): 502 [M+H]$^+$, 524 [M+Na]$^+$, 540 [M+H]$^+$; HPLC: retention time 3.804 min (95.14%).

$^1$H NMR (300 MHz, CDCl$_3$): δ 8.48 (d, 1H, J=4.8 Hz, H-pyridyl), 8.17 (m, 1H, H— pyridyl), 7.30-7.36 (m, 1H, H— pyridyl), 6.29 (s, 1H, H-17), 6.22 (s, 1H, H-14), 5.67 (s, 1H, H-17), 5.38 (d, 1H, J=16.0 Hz, OH-6), 4.36 (d, 1H, J=4.2 Hz), 4.03-4.07 (m, 2H), 3.85 (s, 1H), 3.71-3.78 (m, 1H), 2.05-2.70 (m, 5H), 1.70-1.95 (m, 3H), 1.57-1.67 (m, 2H), 1.19 (s, 3H, CH$_3$-18), 1.00 (s, 3H, CH$_3$-19).

Compound BS-OR-015 was prepared by reacting the compound 1-oxo oridonin with 3,4-dimethoxybenzoic acid according to the process for preparing BS-OR-013 using the same reagents:

MS (m/z): 527 [M+H]$^+$, 549 [M+Na]$^+$, 565 [M+H]$^+$; HPLC: retention time 4.750 min (96.42%).

$^1$H NMR (300 MHz, CDCl$_3$): δ 7.45-7.52 (m, 3H, H-benzene), 6.28 (s, 1H, H-17), 6.03 (s, 1H, H-14), 5.62 (s, 1H, H-17), 5.46 (d, 1H, J=15.4 Hz, OH-6), 4.36 (m, 1H), 4.15 (s, 1H), 4.03-4.07 (m, 1H), 3.91 (s, 3H, H—CH$_3$), 3.88 (s, 3H, H—CH$_3$), 3.30 (m, 1H), 1.91-2.04 (m, 3H), 1.71-1.89 (m, 2H), 1.21 (s, 3H, CH$_3$-18), 1.01 (s, 3H, CH$_3$-19).

Compound BS-OR-011 was prepared by reacting the compound 1-oxo oridonin with 3-picolinc acid according to the process for preparing BS-OR-013 using the same reagents:

MS (m/z): 468 [M+H]$^+$, 490 [M+Na]$^+$, 506 [M+H]$^+$; HPLC: retention time 3.079 min (99.92%).

Compound BS-OR-012 was prepared by reacting the compound 1-oxo oridonin with 4-picolinc acid according to the process for preparing BS-OR-013 using the same reagents:

MS (m/z): 468 [M+H]$^+$, 490 [M+Na]$^+$, 506 [M+H]$^+$; HPLC: retention time 3.160 min (99.99%).

Compound BS-OR-014 was prepared by reacting the compound 1-oxo oridonin with 5-methyl-4-isoxazoleformic acid according to the process for preparing BS-OR-013 using the same reagents:

MS (m/z): 494 [M+Na]$^+$, 510 [M+H]$^+$; HPLC: retention time 3.765 min (98.81%).

Compound BS-OR-017 was prepared by reacting the compound 1-oxo oridonin with cyclopropanecarboxylic acid according to the process for preparing BS-OR-013 using the same reagents:

MS (m/z): 431 [M+H]$^+$, 453 [M+Na]$^+$, 469 [M+H]$^+$; HPLC: retention time 3.535 min (98.26%).

$^1$H NMR (300 MHz, CDCl$_3$): δ 6.26 (s, 1H, H-17), 5.80 (s, 1H, H-14), 5.61 (s, 1H, H-17), 5.42 (d, 1H, J=11.4 Hz, OH-6), 4.30 (d, 1H, J=10.5 Hz), 4.05 (d, 1H, J=10.5 Hz), 3.84 (dd, J=11.4 Hz, 8.7 Hz, 1H), 1.20 (s, 3H, CH$_3$-18), 1.00 (s, 3H, CH$_3$-19).

Example 3: The Synthesis of Compound BS-OR-043

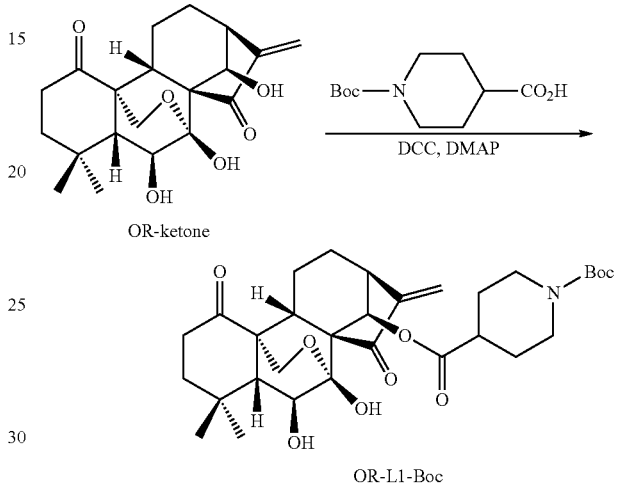

1,3-dicyclohexylcarbodiimide (247 mg, 1.2 mmol) was dissolved in 10 mL dry dichloromethane, to which N-Bocpiperidine-4-carboxylic acid (251 mg, 1.1 mmol) was added at 0° C. After the mixture was stirred for half an hour, 1-oxo oridonin (362 mg, 1 mmol) and 4-dimethylaminopyridine (10 mg, catalytic amount) were added, and the mixture was stirred overnight at room temperature. The resulted crude product was separated via silica gel column to give 1-oxo-14-(4-methyl)benzoyloxy oridonin (435 mg, 79% yield).

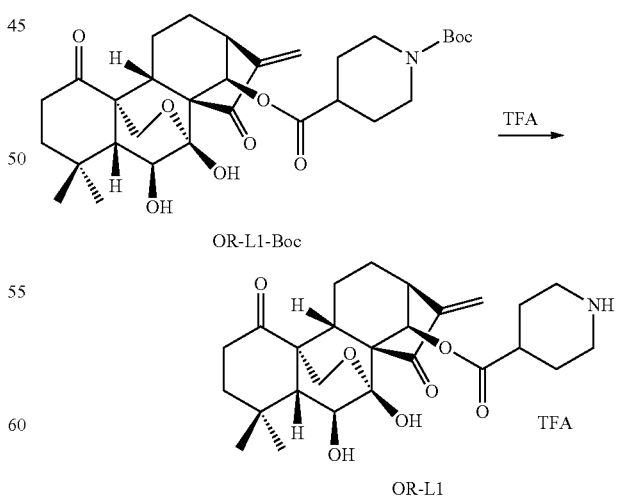

1-oxo-14-(N-Boc-4-acyloxypiperidine)oridonin (114 mg, 0.2 mmol) was dissolved in 5 mL dichloromethane, to which trifluoroacetic acid (0.2 mL) was added. After the mixture was stirred for 1 hour at room temperature, the solvent was rotavapped off to give a crude product (114.2 mg), which was directly used in the subsequent reaction without purification.

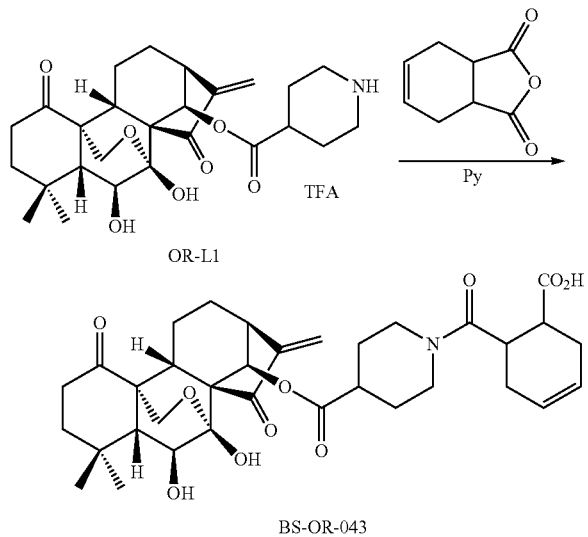

OR-L1

BS-OR-043

1-oxo-14-(4-acyloxypiperidine)oridonin trifluoroacetate (114.2 mg, 0.2 mmol) and pyridine (0.1 mL) were dissolved in 5 mL dichloromethane, to which tetrahydrophthalic anhydride (45.6 mg, 0.3 mmol) was added at 0° C. The mixture was stirred for 4 hours at room temperature, and the starting materials were detected by thin layer chromatography to have disappeared. Dichloromethane (30 mL) was added for dilution. The mixture was washed with 5% hydrochloric acid solution, followed by water and saturated saline solution. The organic phase was dried and concentrated. The resulted crude product was separated via silica gel column to give BS-OR-043 (56.0 mg, 45.03% yield) as a white solid.

MS (m/z): 626 [M+H]$^+$, 648 [M+Na]$^+$, 664 [M+H]$^+$; HPLC: retention time 4.199 min (99.31%).

Example 4: The Synthesis of Compound BS-OR-037

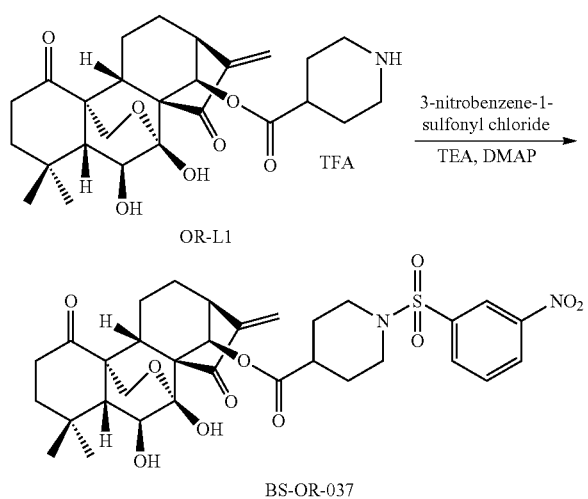

OR-L1

BS-OR-037

1-oxo-14-(4-acyloxypiperidine)oridonin trifluoroacetate (114.2 mg, 0.2 mmol), triethylamine (0.3 mL) and 4-dimethylaminopyridine (10 mg, catalytic amount) were dissolved in 5 mL dichloromethane, to which 3-nitrobenzenesulfonyl chloride (66.3 mg, 0.3 mmol) was added at 0° C. After being stirred for 3 hours at room temperature, the mixture was diluted with dichloromethane (30 mL) and washed with saturated aqueous solution of sodium bicarbonate and saturated saline solution. The organic phase was dried and rotavapped. The resulted crude product was separated via silica gel column to finally give BS-OR-037 (26.2 mg, 83% yield) as a white solid.

MS (m/z): 681 [M+Na]$^+$; HPLC: retention time 3.885 min (100.00%).

$^1$H NMR (300 MHz, CDCl$_3$): δ 8.586 (m, 1H, H-benzene), 8.46 (d, 1H, J=8.1 Hz, H-benzene), 8.07 (d, 1H, J=7.5 Hz, H-benzene), 7.76 (t, 1H, H-benzene), 6.24 (s, 1H, H-17), 5.92 (s, 1H, H-14), 5.62 (s, 1H, H-17), 5.36 (d, 1H, J=11.9 Hz, OH-6), 4.27 (d, 1H, J=10.0 Hz), 3.90-3.95 (m, 2H), 3.71 (dd, 1H, H-6), 3.59-3.70 (m, 2H), 3.00 (d, 1H, J=8.8 Hz, H-13), 1.60-1.80 (m, 3H), 1.25-1.40 (m, 2H), 1.17 (s, 3H, CH$_3$-18), 0.98 (s, 3H, CH$_3$-19).

Compound BS-OR-041 was prepared by reacting the compound 1-oxo-14-(4-acyloxypiperidine)oridonin trifluoroacetate with 3-(trifluoromethyl)benzenesulfonyl chloride according to the process for preparing BS-OR-037 using the same reagents:

MS (m/z): 704 [M+Na]$^+$, 720 [M+H]$^+$; HPLC: retention time 3.173 min (99.30%).

$^1$H NMR (300 MHz, CDCl$_3$): δ 7.98 (s, 1H, H-benzene), 7.93 (d, 1H, J=7.8 Hz, H-benzene), 7.87 (d, 1H, J=7.5 Hz, H-benzene), 7.69 (t, 1H, H-benzene), 6.23 (s, 1H, H-17), 5.92 (s, 1H, H-14), 5.60 (s, 1H, H-17), 5.33 (d, 1H, J=12.0 Hz, OH-6), 4.26 (d, 1H, J=10.6 Hz), 3.90 (d, J=10.2 Hz 1H), 3.89 (s, 1H), 3.71 (dd, 1H, H-6), 3.58-3.70 (m, 2H), 3.00 (d, 1H, J=9.0 Hz, H-13), 1.17 (s, 3H, CH$_3$-18), 0.98 (s, 3H, CH$_3$-19).

Compound BS-OR-042 was prepared by reacting the compound 1-oxo-14-(4-acyloxypiperidine)oridonin trifluoroacetate with 4-(trifluoromethyl)benzenesulfonyl chloride according to the process for preparing BS-OR-037 using the same reagents:

MS (m/z): 704 [M+Na]$^+$, 720 [M+H]$^+$; HPLC: retention time 3.944 min (96.09%).

$^1$H NMR (300 MHz, CDCl$_3$): δ 7.78-7.87 (m, 4H, H-benzene), 6.23 (s, 1H, H-17), 5.92 (s, 1H, H-14), 5.60 (s, 1H, H-17), 5.33 (d, 1H, J=11.9 Hz, OH-6), 4.28 (d, 1H, J=10.5 Hz), 4.00 (d, 1H, J=10.5 Hz), 3.89 (s, 1H) 3.70 (dd, 1H, H-6), 3.58-3.70 (m, 2H), 3.00 (d, 1H, J=9.0 Hz, H-13), 1.60-1.80 (m, 3H), 1.22-1.35 (m, 2H), 1.17 (s, 3H, CH$_3$-18), 0.98 (s, 3H, CH$_3$-19).

Compound BS-OR-025 was prepared by reacting the compound 1-oxo-14-(4-acyloxypiperidine)oridonin trifluoroacetate with p-methylbenzenesulfonyl chloride according to the process for preparing BS-OR-037 using the same reagents:

MS (m/z): 628 [M+H]$^+$, 650 [M+Na]$^+$; HPLC: retention time 6.005 min (92.55%).

Compound BS-OR-026 was prepared by reacting the compound 1-oxo-14-(4-acyloxypiperidine)oridonin trifluoroacetate with 2,4,6-trimethylbenzenesulfonyl chloride according to the process for preparing BS-OR-037 using the same reagents:

MS (m/z): 678 [M+Na]$^+$; HPLC: retention time 12.816 min (99.65%).

Compound BS-OR-027 was prepared by reacting the compound 1-oxo-14-(4-acyloxypiperidine)oridonin trifluoroacetate with p-chlorobenzenesulfonyl chloride according to the process for preparing BS-OR-037 using the same reagents:

MS (m/z): 670 [M+Na]$^+$; HPLC: retention time 10.437 min (98.79%).

Compound BS-OR-032 was prepared by reacting the compound 1-oxo-14-(4-acyloxypiperidine)oridonin trifluoroacetate with benzenesulfonyl chloride according to the process for preparing BS-OR-037 using the same reagents:

MS (m/z): 636 [M+Na]$^+$; HPLC: retention time 4.285 min (99.10%).

Compound BS-OR-034 was prepared by reacting the compound 1-oxo-14-(4-acyloxypiperidine)oridonin trifluoroacetate with o-nitrobenzenesulfonyl chloride according to the process for preparing BS-OR-037 using the same reagents:

MS (m/z): 681 [M+Na]$^+$; HPLC: retention time 6.485 min (98.08%).

Compound BS-OR-035 was prepared by reacting the compound 1-oxo-14-(4-acyloxypiperidine)oridonin trifluoroacetate with p-nitrobenzenesulfonyl chloride according to the process for preparing BS-OR-037 using the same reagents:

MS (m/z): 681 [M+Na]$^+$; HPLC: retention time 7.550 min (100.00%).

Compound BS-OR-038 was prepared by reacting the compound 1-oxo-14-(4-acyloxypiperidine)oridonin trifluoroacetate with ethylsulfonyl chloride using the same reagents as above according to the process for preparing BS-OR-037:

MS (m/z): 588 [M+Na]$^+$, 604 [M+H]$^+$; HPLC: retention time 3.849 min (99.05%).

Compound BS-OR-039 was prepared by reacting the compound 1-oxo-14-(4-acyloxypiperidine)oridonin trifluoroacetate with n-butylsulfonyl chloride according to the process for preparing BS-OR-037 using the same reagents:

MS (m/z): 616 [M+Na]$^+$, 632 [M+H]$^+$; HPLC: retention time 6.844 min (100.00%).

Compound BS-OR-040 was prepared by reacting the compound 1-oxo-14-(4-acyloxypiperidine)oridonin trifluoroacetate with methylsulfonyl chloride according to the process for preparing BS-OR-037 using the same reagents:

MS (m/z): 574 [M+Na]$^+$, 590 [M+H]$^+$; HPLC: retention time 3.618 min (100.00%).

Compound BS-OR-044 was prepared by reacting the compound 1-oxo-14-(4-acyloxypiperidine)oridonin trifluoroacetate with p-fluorobenzenesulfonyl chloride according to the process for preparing BS-OR-037 using the same reagents:

MS (m/z): 654 [M+Na]$^+$; HPLC: retention time 5.203 min (91.89%).

Example 5: The Synthesis of Compound BS-OR-050

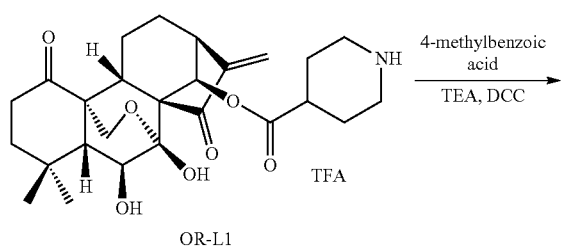

OR-L1

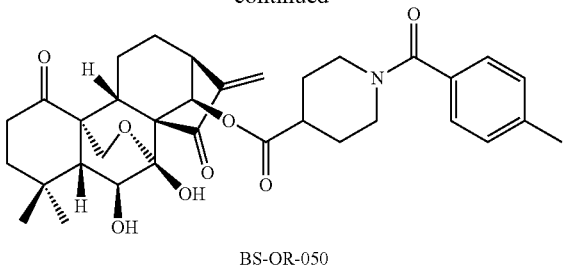

BS-OR-050

4-Methylbenzoic acid (41 mg, 0.3 mmol) was dissolved in 2 mL dichloromethane, to which 1,3-dicyclohexylcarbodiimide (65 mg, 0.25 mmol) was added at 0° C. After the mixture was stirred for 1 hour, 1-oxo-14-(4-acyloxypiperidine)oridonin trifluoroacetate (114.2 mg, 0.2 mmol) was added, followed by triethylamine (0.3 mL) dissolved in dichloromethane (3 mL). After the mixture was stirred for 8 hours at room temperature, the resulted crude product was separated via silica gel column to give BS-OR-050 (34.1 mg, 74% yield) as a white solid.

MS (m/z): 592 [M+H]$^+$, 614 [M+Na]$^+$, 630 [M+H]$^+$; HPLC: retention time 4.901 min (98.49%).

Compound BS-OR-047 was prepared by reacting the compound 1-oxo-14-(4-acyloxypiperidine)oridonin trifluoroacetate with p-fluorobenzoic acid according to the process for preparing BS-OR-050 using the same reagents:

MS (m/z): 596 [M+H]$^+$; HPLC: retention time 8.615 min (92.83%).

Compound BS-OR-048 was prepared by reacting the compound 1-oxo-14-(4-acyloxypiperidine)oridonin trifluoroacetate with pivalic acid according to the process for preparing BS-OR-050 using the same reagents:

MS (m/z): 558 [M+H]$^+$, 580 [M+Na]$^+$; HPLC: retention time 3.453 min (96.79%).

Compound BS-OR-049 was prepared by reacting the compound 1-oxo-14-(4-acyloxypiperidine)oridonin trifluoroacetate with p-methoxybenzoic acid according to the process for preparing BS-OR-050 using the same reagents:

MS (m/z): 608 [M+H]$^+$, 620 [M+Na]$^+$; HPLC: retention time 4.044 min (97.96%).

Compound BS-OR-051 was prepared by reacting the compound 1-oxo-14-(4-acyloxypiperidine)oridonin trifluoroacetate with cyclopropanecarboxylic acid according to the process for preparing BS-OR-050 using the same reagents:

MS (m/z): 542 [M+H]$^+$, 564 [M+Na]$^+$; HPLC: retention time 3.809 min (100.00%).

Compound BS-OR-052 was prepared by reacting the compound 1-oxo-14-(4-acyloxypiperidine)oridonin trifluoroacetate with 2-chloroisonicotinic acid according to the process for preparing BS-OR-050 using the same reagents:

MS (m/z): 635 [M+Na]$^+$, 651 [M+H]$^+$; HPLC: retention time 4.281 min (90.77%).

Compound BS-OR-053 was prepared by reacting the compound 1-oxo-14-(4-acyloxypiperidine)oridonin trifluoroacetate with furoic acid according to the process for preparing BS-OR-050 using the same reagents:

MS (m/z): 568 [M+H]$^+$, 590 [M+Na]$^+$; HPLC: retention time 4.065 min (98.6386%).

Compound BS-OR-054 was prepared by reacting the compound 1-oxo-14-(4-acyloxypiperidine)oridonin trifluoroacetate with 2-thiophene formic acid according to the process for preparing BS-OR-050 using the same reagents:

MS (m/z): 623 [M+H]$^+$, 645 [M+Na]$^+$; HPLC: retention time 4.361 min (97.90%).

Compound BS-OR-055 was prepared by reacting the compound 1-oxo-14-(4-acyloxypiperidine)oridonin trifluoroacetate with p-nitrobenzoic acid according to the process for preparing BS-OR-050 using the same reagents:

MS (m/z): 584 [M+H]⁺, 606 [M+Na]⁺; HPLC: retention time 4.610 min (98.78%).

Compound BS-OR-056 was prepared by reacting the compound 1-oxo-14-(4-acyloxypiperidine)oridonin trifluoroacetate with benzoic acid according to the process for preparing BS-OR-050 using the same reagents:

MS (m/z): 578 [M+H]⁺, 600 [M+Na]⁺, 616 [M+H]⁺; HPLC: retention time 4.986 min (98.68%).

Compound BS-OR-057 was prepared by reacting the compound 1-oxo-14-(4-acyloxypiperidine)oridonin trifluoroacetate with phenylpropionic acid according to the process for preparing BS-OR-050 using the same reagents:

MS (m/z): 606 [M+H]⁺, 628 [M+Na]⁺, 644 [M+H]⁺; HPLC: retention time 8.003 min (98.08%).

Compound BS-OR-058 was prepared by reacting the compound 1-oxo-14-(4-acyloxypiperidine)oridonin trifluoroacetate with D-valine according to the process for preparing BS-OR-050 using the same reagents:

MS (m/z): 556 [M+H]⁺, 578 [M+Na]⁺, 594 [M+H]⁺; HPLC: retention time 6.586 min (98.80%).

Example 6: The Synthesis of Compound BS-OR-059

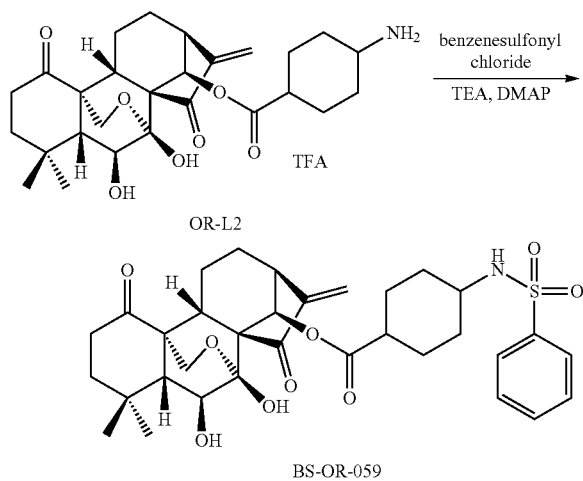

1-Oxo-14-(4-acyloxycyclohexylamine)oridonin trifluoroacetate (116.8 mg, 0.2 mmol), triethylamine (0.3 mL) and 4-dimethylaminopyridine (10 mg, catalytic amount) were dissolved in 5 mL dichloromethane, to which benzenesulfonyl chloride (53 mg, 0.3 mmol) was added at ice-bath conditions. After being stirred for 3 hours at room temperature, the mixture was diluted with dichloromethane (30 mL) and washed with saturated aqueous solution of sodium bicarbonate, followed by saturated saline solution. The mixture was dried and rotavapped. The resulted crude product was separated via silica gel column to give BS-OR-059 (21.0 mg, 53% yield) as a white solid.

MS (m/z): 650 [M+Na]⁺; HPLC: retention time 4.869 min (95.26%).

¹H NMR (300 MHz, CDCl₃): δ 7.85-7.87 (m, 2H, H-benzene), 7.50-7.57 (m, 3H, H-benzene), 6.24 (s, 1H, H-17), 5.87 (s, 1H, H-14), 5.61 (s, 1H, H-17), 5.38 (d, 1H, J=15.8 Hz, OH-6), 4.68-4.72 (m, 1H), 4.29 (d, 1H, J=13.8 Hz), 4.15 (s, 1H), 4.02 (d, 1H, J=13.9 Hz), 3.74-3.81 (m, 1H), 3.07 (d, 1H, J=11.8 Hz, H-13), 2.18-2.54 (m, 5H), 1.74-1.96 (m, 3H), 1.26-1.35 (m, 2H), 1.17 (s, 3H, CH₃-18), 0.99 (s, 3H, CH₃-19).

Compound BS-OR-063 was prepared by reacting the compound 1-oxo-14-(4-acyloxycyclohexylamine)oridonin trifluoroacetate with m-nitrobenzenesulfonyl chloride according to the process for preparing BS-OR-059 using the same reagents:

MS (m/z): 695 [M+Na]⁺, 711 [M+H]⁺; HPLC: retention time 5.356 min (100.00%).

¹H NMR (300 MHz, CDCl₃): δ 8.71-8.72 (m, 1H, H-group), 8.41-8.44 (m, 1H, H-benzene), 8.20-8.23 (m, 1H, H-benzene), 7.71-7.76 (m, 1H, H-benzene), 6.25 (s, 1H, H-17), 5.93 (s, 1H, H-14), 5.62 (s, 1H, H-17), 5.39-5.41 (m, 1H, OH-6), 4.27-4.31 (m, 2H), 4.03 (d, 1H, J=13.9 Hz), 3.80 (t, 1H, J=13.7 Hz), 3.32-3.41 (m, 1H), 3.07 (d, 1H, J=4.2 Hz, H-13), 2.18-2.54 (m, 5H), 1.68-1.96 (m, 3H), 1.26-1.35 (m, 2H), 1.19 (s, 3H, CH₃-18), 1.00 (s, 3H, CH₃-19).

Compound BS-OR-064 was prepared by reacting the compound 1-oxo-14-(4-acyloxycyclohexylamine)oridonin trifluoroacetate with 3-(trifluoromethyl)benzenesulfonyl chloride according to the process for preparing BS-OR-059 using the same reagents:

MS (m/z): 718 [M+Na]⁺, 734 [M+H]⁺; HPLC: retention time 6.755 min (100.00%).

¹H NMR (300 MHz, CDCl₃): δ 8.05-8.14 (m, 2H, H-benzene), 7.82-7.84 (m, 1H, H-benzene), 7.64-7.69 (m, 1H, H-benzene), 6.24 (s, 1H, H-17), 5.93 (s, 1H, H-14), 5.61 (s, 1H, H-17), 5.39-5.41 (m, 1H, OH-6), 4.29 (d, 2H, J=14.4 Hz), 4.03 (d, 1H, J=12.9 Hz), 3.79-3.82 (m, 1H), 3.28-3.37 (m, 1H), 3.06 (d, 1H, J=11.9 Hz, H-13), 2.19-2.52 (m, 5H), 1.78-1.96 (m, 3H), 1.20-1.29 (m, 2H), 1.19 (s, 3H, CH₃-18), 1.00 (s, 3H, CH₃-19).

Compound BS-OR-029 was prepared by reacting the compound 1-oxo-14-(4-acyloxycyclohexylamine)oridonin trifluoroacetate with p-methylbenzenesulfonyl chloride using the same reagents as above according to the process for preparing BS-OR-059:

MS (m/z): 664 [M+Na]⁺; HPLC: retention time 6.893 min (100.00%).

Compound BS-OR-061 was prepared by reacting the compound 1-oxo-14-(4-acyloxycyclohexylamine)oridonin trifluoroacetate with o-nitrobenzenesulfonyl chloride according to the process for preparing BS-OR-059 using the same reagents:

MS (m/z): 695 [M+Na]⁺, 711 [M+H]⁺; HPLC: retention time 4.315 min (100.00%).

¹H NMR (300 MHz, CDCl₃): δ 8.15 (m, 1H, H-benzene), 7.90 (m, 1H, H-benzene), 7.75 (m, 2H, H-benzene), 6.24 (s, 1H, H-17), 5.86 (s, 1H, H-14), 5.63 (s, 1H, H-17), 5.37 (d, 1H, OH-6), 4.31 (d, 1H, J=10.2 Hz), 4.04 (m, 1H), 3.79 (dd, J=12 Hz, 6 Hz, 1H), 3.51 (m, 1H), 3.11 (d, 1H, J=9.9 Hz, H-13), 1.95 (d, J=9.3 Hz, 1H), 1.27-1.34 (m, 2H), 1.19 (s, 3H, CH₃-18), 0.99 (s, 3H, CH₃-19).

Compound BS-OR-062 was prepared by reacting the compound 1-oxo-14-(4-acyloxycyclohexylamine)oridonin trifluoroacetate with butylsulfonyl chloride according to the process for preparing BS-OR-059 using the same reagents:

MS (m/z): 630 [M+Na]⁺; HPLC: retention time 4.994 min (97.54%).

Compound BS-OR-065 was prepared by reacting the compound 1-oxo-14-(4-acyloxycyclohexylamine)oridonin trifluoroacetate with 4-(trifluoromethyl)benzenesulfonyl chloride according to the process for preparing BS-OR-059 using the same reagents:

MS (m/z): 718 [M+Na]⁺, 734 [M+H]⁺; HPLC: retention time 6.942 min (98.94%).

¹H NMR (300 MHz, CDCl₃): δ 8.01 (d, 1H, J=8.4 Hz, H-benzene), 7.79 (d, 1H, J=8.7 Hz, H-benzene), 6.24 (s, 1H, H-17), 5.89 (s, 1H, H-14), 5.61 (s, 1H, H-17), 5.39 (d, 1H, J=11.7 Hz, OH-6), 4.87 (d, 1H, J=6.6 Hz), 4.31 (d, 1H, J=10.5 Hz), 4.12 (s, 1H), 4.04 (d, J=10.2 Hz, 1H), 3.77 (dd, J=11.7 Hz, 8.7 Hz, 1H), 3.36 (m, 1H), 3.07 (d, 1H, J=9.0 Hz, H-13), 1.96 (d, J=9.3 Hz, 1H), 1.19 (s, 3H, CH₃-18), 1.00 (s, 3H, CH₃-19).

Compound BS-OR-066 was prepared by reacting the compound 1-oxo-14-(4-acyloxycyclohexylamine)oridonin trifluoroacetate with 4-fluorobenzenesulfonyl chloride according to the process for preparing BS-OR-059 using the same reagents:

MS (m/z): 668 [M+Na]⁺, 684 [M+H]⁺; HPLC: retention time 4.681 min (93.63%).

Compound BS-OR-067 was prepared by reacting the compound 1-oxo-14-(4-acyloxycyclohexylamine)oridonin trifluoroacetate with 4-tert-butylbenzenesulfonyl chloride according to the process for preparing BS-OR-059 using the same reagents:

MS (m/z): 706 [M+Na]⁺; HPLC: retention time 8.732 min (97.67%).

¹H NMR (300 MHz, CDCl₃): δ 7.78 (d, 1H, J=8.1 Hz, H-benzene), 7.61 (d, 1H, J=8.4 Hz, H-benzene), 6.24 (s, 1H, H-17), 5.86 (s, 1H, H-14), 5.61 (s, 1H, H-17), 5.37 (d, 1H, OH-6), 4.55 (d, 1H), 4.31 (d, 1H, J=10.8 Hz), 4.04 (d, J=10.8 Hz, 1H), 3.77 (m, 1H), 3.30 (m, 1H), 3.09 (d, 1H, J=9.3 Hz, H-13), 1.96 (d, J=7.8 Hz, 1H), 1.19 (s, 3H, CH₃-18), 1.00 (s, 3H, CH₃-19).

Compound BS-OR-070 was prepared by reacting the compound 1-oxo-14-(4-acyloxycyclohexylamine)oridonin trifluoroacetate with benzylsulfonyl chloride according to the process for preparing BS-OR-059 using the same reagents:

MS (m/z): 664 [M+Na]⁺, 680 [M+H]⁺; HPLC: retention time 5.296 min (90.88%).

Compound BS-OR-086 was prepared by reacting the compound 1-oxo-14-(4-acyloxycyclohexylamine)oridonin trifluoroacetate with p-chlorobenzenesulfonyl chloride according to the process for preparing BS-OR-059 using the same reagents:

MS (m/z): 684 [M+Na]⁺; HPLC: retention time 8.923 min (93.73%).

Compound BS-OR-087 was prepared by reacting the compound 1-oxo-14-(4-acyloxycyclohexylamine)oridonin trifluoroacetate with p-nitrobenzenesulfonyl chloride according to the process for preparing BS-OR-059 using the same reagents:

MS (m/z): 673 [M+H]⁺, 695 [M+Na]⁺, 711 [M+H]⁺; HPLC: retention time 4.121 min (90.67%).

Example 7: The Synthesis of Compound BS-OR-072

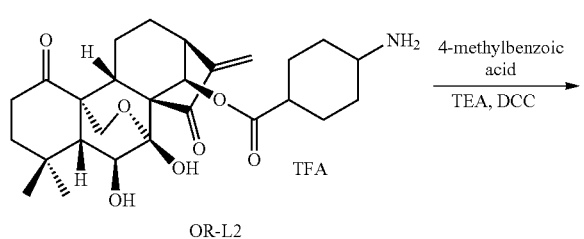

OR-L2

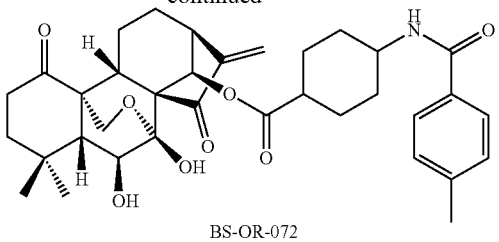

BS-OR-072

4-Methylbenzoic acid (41 mg, 0.3 mmol) was dissolved in 2 mL dichloromethane, to which 1,3-dicyclohexylcarbodiimide (65 mg, 0.25 mmol) was added at ice-bath conditions. After stirring for 1 hour, 1-oxo-14-(4-acyloxycyclohexylamine)oridonin trifluoroacetate (116.8 mg, 0.2 mmol) was added, followed by triethylamine (0.3 mL) dissolved in dichloromethane (3 mL). After stirring for 8 hours at room temperature, the resulted crude product was separated via silica gel column to give BS-OR-072 (40.0 mg, 66% yield) as a white solid.

MS (m/z): 606 [M+H]⁺, 628 [M+Na]⁺, 644 [M+H]⁺; HPLC: retention time 6.475 min (93.18%).

¹H NMR (300 MHz, CDCl₃): δ 7.61-7.64 (m, 2H, H-benzene), 7.26-7.27 (m, 2H, H-benzene), 6.25 (s, 1H, H-17), 6.00-6.02 (m, 1H), 5.84-5.89 (m, 1H, H-14), 5.62 (s, 1H, H-17), 5.35-5.39 (m, 1H, OH-6), 4.27-4.28 (m, 1H), 4.02-4.13 (m, 2H), 3.78-3.79 (m, 1H), 3.07-3.11 (m, 1H, H-13), 2.35 (s, 3H, CH₃-benzene), 2.21-2.47 (m, 5H), 1.40-1.72 (m, 1H), 1.26-1.32 (m, 3H), 1.20 (s, 3H, CH₃-18), 1.07-1.11 (m, 2H), 1.00 (s, 3H, CH₃-19).

Compound BS-OR-079 was prepared by reacting the compound 1-oxo-14-(4-acyloxycyclohexylamine)oridonin trifluoroacetate with p-chlorobenzoic acid according to the process for preparing BS-OR-072 using the same reagents:

MS (m/z): 648 [M+Na]⁺, 664 [M+H]⁺; HPLC: retention time 7.276 min (93.66%).

¹H NMR (300 MHz, CDCl₃): δ 7.66-7.69 (m, 2H, H-benzene), 7.38-7.42 (m, 2H, H-benzene), 6.25 (s, 1H, H-17), 6.00-6.02 (m, 1H), 5.87 (d, 1H, J=19.6 Hz, H-14), 5.62 (s, 1H, H-17), 5.39 (d, 1H, J=16.0 Hz, OH-6), 4.30 (d, 1H, J=14.0 Hz), 4.02-4.10 (m, 2H), 3.73-3.80 (m, 1H), 3.04-3.11 (m, 1H, H-13), 2.21-2.47 (m, 5H), 1.40-1.72 (m, 10H), 1.26-1.32 (m, 3H), 1.19 (s, 3H, CH₃-18), 1.07-1.11 (m, 2H), 1.00 (s, 3H, CH₃-19).

Compound BS-OR-080 was prepared by reacting the compound 1-oxo-14-(4-acyloxycyclohexylamine)oridonin trifluoroacetate with pivalic acid according to the process for preparing BS-OR-072 using the same reagents:

MS (m/z): 572 [M+H]⁺, 594 [M+Na]⁺, 610 [M+H]⁺; HPLC: retention time 5.584 min (94.02%).

¹H NMR (300 MHz, CDCl₃): δ 6.26 (s, 1H, H-17), 5.86 (d, 1H, J=25.4 Hz, H-14), 5.62 (s, 1H, H-17), 5.32-5.38 (m, 1H, OH-6), 4.26-4.31 (m, 1H), 4.02-4.06 (m, 2H), 3.64-3.85 (m, 2H), 3.08-3.12 (m, 1H), 2.22-2.44 (m, 5H), 1.62-1.72 (m, 10H), 1.29-1.32 (m, 3H), 1.17 (s, 12H, H—CH₃), 1.07-1.14 (m, 2H), 1.00 (s, 3H, CH₃-19).

Compound BS-OR-083 was prepared by reacting the compound 1-oxo-14-(4-acyloxycyclohexylamine)oridonin trifluoroacetate with 2-picolinic acid according to the process for preparing BS-OR-072 using the same reagents:

MS (m/z): 593 [M+H]⁺, 615 [M+Na]⁺, 631 [M+H]⁺; HPLC: retention time 5.072 min (98.23%).

¹H NMR (300 MHz, CDCl₃): δ 8.58-8.60 (m, 1H, H-pyridyl), 8.16-8.19 (m, 1H, H-pyridyl), 7.83-7.87 (m, 1H, H-pyridyl), 7.41-7.44 (m, 1H, H-pyridyl), 6.26 (s, 1H, H-17), 5.87 (d, 1H, J=12.44 Hz, H-14), 5.62 (s, 1H, H-17), 5.37-5.43 (m, 1H, OH-6), 4.23-4.33 (m, 2H), 4.07-4.11 (m, 1H), 4.02-4.07 (m, 1H), 3.76-3.82 (m, 1H), 3.14 (d, 1H, J=13.0 Hz, H-13), 2.35-2.47 (m, 5H), 1.62-1.72 (m, 10H), 1.29-1.32 (m, 3H), 1.20 (s, 3H, CH$_3$-18), 1.07-1.14 (m, 2H), 1.00 (s, 3H, CH$_3$-19).

Compound BS-OR-071 was prepared by reacting the compound 1-oxo-14-(4-acyloxycyclohexylamine)oridonin trifluoroacetate with p-methoxybenzoic acid according to the process for preparing BS-OR-072 using the same reagents:

MS (m/z): 622 [M+H]$^+$, 644 [M+Na]$^+$, 660 [M+H]$^+$; HPLC: retention time 5.520 min (90.14%).

$^1$H NMR (300 MHz, CDCl$_3$): δ 7.71 (d, 1H, J=9.0 Hz, H-benzene), 6.94 (d, 1H, J=8.7 Hz, H-benzene), 6.25 (s, 1H, H-17), 5.90 (d, 1H, J=12.44 Hz, H-14), 5.62 (s, 1H, H-17), 5.39 (d, 1H, J=11.1 Hz, OH-6), 4.32 (d, J=10.5 Hz, 1H), 4.05 (d, J=9.6 Hz, 1H), 3.85 (s, 3H), 3.13 (d, 1H, H-13), 1.29-1.32 (m, 2H), 1.20 (s, 3H, CH$_3$-18), 1.00 (s, 3H, CH$_3$-19).

Compound BS-OR-073 was prepared by reacting the compound 1-oxo-14-(4-acyloxycyclohexylamine)oridonin trifluoroacetate with 3-methylbenzoic acid according to the process for preparing BS-OR-072 using the same reagents:

MS (m/z): 606 [M+H]$^+$, 628 [M+Na]$^+$, 644 [M+H]$^+$; HPLC: retention time 6.575 min (94.92%).

$^1$H NMR (300 MHz, CDCl$_3$): δ 7.55 (m, 2H, H-benzene), 7.30 (m, 2H, H-benzene), 6.25 (s, 1H, H-17), 5.90 (s, 1H, H-14), 5.62 (s, 1H, H-17), 5.40 (d, 1H, J=11.7 Hz, OH-6), 4.32 (d, J=10.5 Hz, 1H), 4.05 (d, J=10.2 Hz, 1H), 3.46 (m, 1H), 3.13 (d, 1H, H-13), 2.47 (s, 3H), 1.29-1.32 (m, 2H), 1.20 (s, 3H, CH$_3$-18), 1.00 (s, 3H, CH$_3$-19).

Compound BS-OR-074 was prepared by reacting the compound 1-oxo-14-(4-acyloxycyclohexylamine)oridonin trifluoroacetate with 3-nitrobenzoic acid according to the process for preparing BS-OR-072 using the same reagents:

MS (m/z): 637 [M+H]$^+$, 659 [M+Na]$^+$; HPLC: retention time 5.965 min (100.00%).

$^1$H NMR (300 MHz, CDCl$_3$): δ 8.58 (s, 1H, H-benzene), 8.37 (d, 1H, J=7.2 Hz, H-benzene), 8.12 (d, 1H, H-benzene), 7.68 (t, 1H, J=7.8 Hz, H-benzene), 6.25 (s, 1H, H-17), 5.92 (s, 1H, H-14), 5.63 (s, 1H, H-17), 5.42 (d, 1H, J=11.1 Hz, OH-6), 4.33 (d, J=10.5 Hz, 1H), 4.05 (d, J=10.2 Hz, 1H), 3.09 (d, 1H, H-13), 1.25 (m, 2H), 1.20 (s, 3H, CH$_3$-18), 1.00 (s, 3H, CH$_3$-19).

Compound BS-OR-075 was prepared by reacting the compound 1-oxo-14-(4-acyloxycyclohexylamine)oridonin trifluoroacetate with 2-thiophene formic acid according to the process for preparing BS-OR-072 using the same reagents:

MS (m/z): 598 [M+11]$^+$, 620 [M+Na]$^+$, 636 [M+H]$^+$; HPLC: retention time 4.937 min (95.67%).

$^1$H NMR (300 MHz, CDCl$_3$): δ 7.47 (d, 2H, J=7.8 Hz, H-thiophene), 7.09 (t, 1H, H-thiophene), 6.26 (s, 1H, H-17), 5.90 (s, 1H, H-14), 5.62 (s, 1H, H-17), 5.40 (d, 1H, J=11.7 Hz, OH-6), 4.30 (d, J=10.2 Hz, 1H), 4.06 (d, J=10.5 Hz, 1H), 3.12 (d, 1H, J=9.6 Hz, H-13), 1.26 (m, 2H), 1.20 (s, 3H, CH$_3$-18), 1.00 (s, 3H, CH$_3$-19).

Compound BS-OR-076 was prepared by reacting the compound 1-oxo-14-(4-acyloxycyclohexylamine)oridonin trifluoroacetate with benzoic acid according to the process for preparing BS-OR-072 using the same reagents:

MS (m/z): 592 [M+11]$^+$, 614 [M+Na]$^+$, 630 [M+H]$^+$; HPLC: retention time 4.923 min (97.14%).

$^1$H NMR (300 MHz, CDCl$_3$): δ 7.74 (d, 2H, J=6.6 Hz, H-benzene), 7.46 (m, 3H, H-benzene), 6.25 (s, 1H, H-17), 5.90 (s, 1H, H-14), 5.62 (s, 1H, H-17), 5.40 (d, 1H, J=11.4 Hz, OH-6), 4.29 (d, 1H), 4.06 (d, J=10.2 Hz, 1H), 3.09 (d, 1H, H-13), 1.26 (m, 2H), 1.20 (s, 3H, CH$_3$-18), 1.00 (s, 3H, CH$_3$-19).

Compound BS-OR-077 was prepared by reacting the compound 1-oxo-14-(4-acyloxycyclohexylamine)oridonin trifluoroacetate with p-fluorobenzoic acid according to the process for preparing BS-OR-072 using the same reagents:

MS (m/z): 610 [M+11]$^+$, 632 [M+Na]$^+$, 648 [M+H]$^+$; HPLC: retention time 5.824 min (97.27%).

$^1$H NMR (300 MHz, CDCl$_3$): δ 7.77 (d, 2H, J=8.1 Hz, H-benzene), 7.11 (d, 2H, J=8.1 Hz, H-benzene), 6.25 (s, 1H, H-17), 5.90 (s, 1H, H-14), 5.62 (s, 1H, H-17), 5.36 (d, 1H, OH-6), 4.29 (d, 1H), 4.06 (d, J=10.8 Hz, 1H), 3.08 (d, 1H, H-13), 1.20 (s, 3H, CH$_3$-18), 1.00 (s, 3H, CH$_3$-19).

Compound BS-OR-078 was prepared by reacting the compound 1-oxo-14-(4-acyloxycyclohexylamine)oridonin trifluoroacetate with o-chlorobenzoic acid according to the process for preparing BS-OR-072 using the same reagents:

MS (m/z): 626 [M+H]$^+$, 648 [M+Na]$^+$; HPLC: retention time 5.344 min (95.34%).

$^1$H NMR (300 MHz, CDCl$_3$): δ 7.66 (m, 1H, H-benzene), 7.41 (m, 3H, H-benzene), 6.25 (s, 1H, H-17), 5.88 (s, 1H, H-14), 5.61 (s, 1H, H-17), 5.40 (d, 1H, OH-6), 4.31 (d, J=10.2 Hz, 1H), 4.05 (d, J=10.8 Hz, 1H), 3.08 (d, 1H, H-13), 1.20 (s, 3H, CH$_3$-18), 1.00 (s, 3H, CH$_3$-19).

Compound BS-OR-088 was prepared by reacting the compound 1-oxo-14-(4-acyloxycyclohexylamine)oridonin trifluoroacetate with 2-furoic acid according to the process for preparing BS-OR-072 using the same reagents:

MS (m/z): 582 [M+H]$^+$, 604 [M+Na]$^+$; HPLC: retention time 6.675 min (95.92%).

Example 8: The Synthesis of Compound BS-OR-090

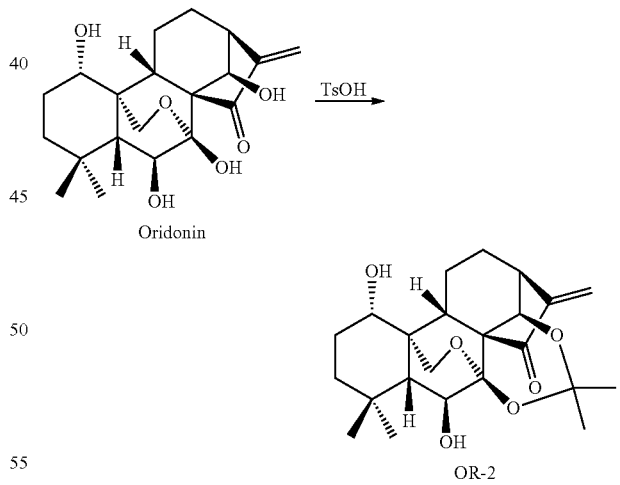

wherein TsOH is benzenesulfonic acid.

Oridonin (3 g, 8.23 mmol) was dissolved in 90 mL acetone, to which benzenesulfonic acid (90 mg, 0.52 mmol) was added in a catalytic amount. The mixture was stirred overnight at 25° C. After the completion of the reaction detected by TLC (ethyl acetate:petroleum ether=1:1), saturated sodium bicarbonate was added to quench the reaction. The mixture was extracted with dichloromethane. The organic phases were combined, washed with saturated saline solution, dried and concentrated. The resulted crude product was separated via silica gel column (petroleum ether:ethyl acetate=1:1) to give the compound OR-2 (1.05 g, 31.5% yield) as a white solid.

MS (m/z): 427 [M+Na]+.

$^1$H NMR (300 MHz, CDCl$_3$): δ 6.15 (s, 1H, H-17), 5.78 (d, 1H, J=15.76 Hz, H-14), 5.55 (s, 1H, H-17), 4.80 (s, 1H, OH-6), 4.25 (d, 1H, J=13.12 Hz), 4.03-4.07 (m, 1H), 3.86-3.93 (m, 1H), 3.45-3.50 (m, 1H), 3.07 (d, 1H, J=12.6 Hz, H-13), 2.50-2.55 (m, 1H), 1.88-2.00 (m, 1H), 1.25-1.77 (m, 9H), 1.33 (s, 6H), 1.17 (s, 3H, CH$_3$-18), 1.15 (s, 3H, CH$_3$-19).

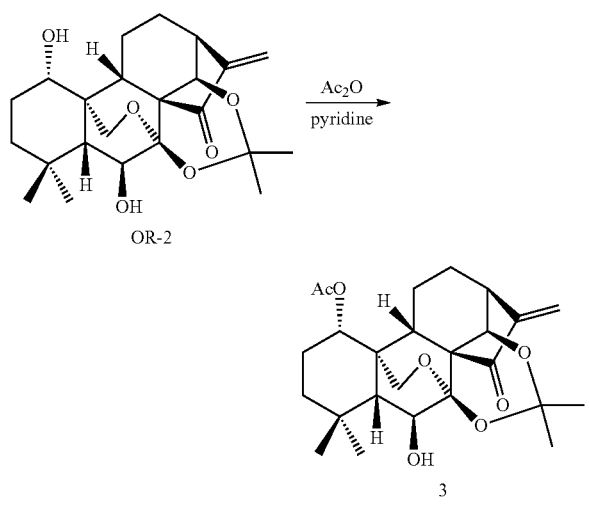

wherein Ac$_2$O is acetic anhydride.

The compound OR-2 (1.05 g, 2.6 mmol) was dissolved in 70 mL anhydrous pyridine, to which acetic anhydride (3.5 g, 3.9 mmol) was added slowly dropwise. The mixture was stirred overnight at room temperature, and the solvent was rotavapped off. The resulted crude product was separated via silica gel column (petroleum ether:ethyl acetate=3:1) to give the compound 3 (1.1 g, 95% yield) as a white solid.

MS (m/z): 447 [M+H]+, 469 [M+Na]+.

$^1$H NMR (300 MHz, CDCl$_3$): δ 6.18 (s, 1H, H-17), 0.81 (d, 1H, J=15.8 Hz, H-14), 5.57 (s, 1H, H-17), 4.77 (s, 1H, OH-6), 4.59-4.65 (m, 1H), 4.15-4.25 (m, 2H), 3.90-3.97 (m, 1H), 3.07 (d, 1H, J=12.3 Hz, H-13), 2.45-2.53 (m, 1H), 1.99 (s, 3H), 1.25-1.83 (m, 9H), 1.33 (s, 6H), 1.17 (s, 3H, CH$_3$-18), 1.15 (s, 3H, CH$_3$-19).

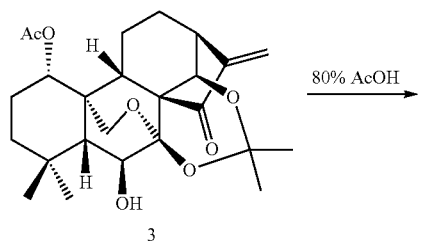

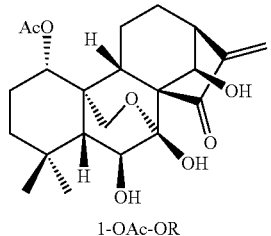

1-OAc-OR wherein 1-OAc—OR is 1-acetyloridonin

Compound 3 (1.1 g, 2.46 mmol) was dissolved in 33 mL of 80% acetic acid solution and the reaction proceeds for 12 hours at 40° C. After the reaction was completed, the reaction solution was concentrated. The resulted crude product was separated via silica gel column (dichloromethane:methanol=20:1) to give 1-acetyloridonin (780 mg, 78% yield) as a white solid.

MS (m/z): 429 [M+Na]+.

$^1$H NMR (300 MHz, CDCl$_3$): δ 6.46 (m, 1H), 6.20 (s, 1H, H-17), 5.58 (s, 1H, H-17), 4.87 (s, 1H, OH-6), 4.58-4.62 (m, 1H), 4.18-4.26 (m, 2H), 3.75-3.82 (m, 2H), 3.50 (s, 1H), 3.08 (d, 1H, J=12.7 Hz, H-13), 2.32-2.45 (m, 1H), 2.00 (s, 3H), 1.25-1.83 (m, 9H), 1.33 (s, 6H), 1.16 (s, 3H, CH$_3$-18), 1.15 (s, 3H, CH$_3$-19).

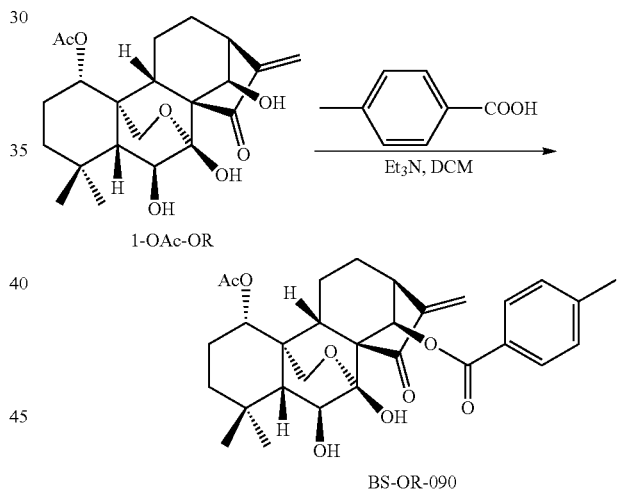

p-Methylbenzoic acid (30.6 mg, 0.225 mmol) was dissolved in dry dichloromethane (5 mL), to which oxalyl chloride (38 mg, 0.30 mmol) was added. After being stirred for 1.5 hours at room temperature, the mixture was rotavapped to give p-methylbenzoyl chloride. 1-Acetyloridonin (61.0 mg, 0.15 mmol) and triethylamine (45.5 mg, 0.45 mmol) were dissolved in dichloromethane (5 mL), to which the p-methylbenzoyl chloride obtained above was added. After the mixture was stirred for 2 hours at room temperature, dichloromethane (30 mL) and saturated sodium bicarbonate (30 mL) were added. The organic phase was washed with 5% hydrochloric acid and saturated saline solution, dried and rotavapped. The resulted crude product was separated via silica gel column (petroleum ether:ethyl acetate=3:1) to give the BS-OR-090 (29 mg, 70% yield) as a white solid.

MS (m/z): 525 [M+H]+. 547 [M+Na]+; HPLC: retention time 7.170 min (97.37%).

$^1$H NMR (300 MHz, CDCl$_3$): δ 7.78-7.81 (m, 2H, H-benzene), 7.22-7.26 (m, 2H, H-benzene), 6.14-6.19 (m, 2H), 6.04 (s, 1H), 5.50 (s, 1H, H-17), 4.63-4.67 (s, 1H, OH-6), 4.33 (d, 1H, J=12 Hz, H-13), 4.20-4.22 (m, 2H), 3.78-3.83 (m, 1H), 3.31 (d, 1H, J=12 Hz, H-13), 2.50-2.70 (m, 1H), 2.35 (s, 3H, H-benzene methyl), 2.02 (s, 3H), 1.26-1.80 (m, 9H), 1.15 (s, 3H, CH$_3$-18), 1.13 (s, 3H, CH$_3$-19).

Compound BS-OR-091 was prepared by reacting 1-acetyloridonin with p-methoxybenzoic acid according to the process for preparing BS-OR-090 using the same reagents:

MS (m/z): 541 [M+H]$^+$, 563 [M+Na]$^+$; HPLC: retention time 4.079 min (93.44%).

$^1$H NMR (300 MHz, CDCl$_3$): δ 7.85-7.88 (m, 2H, H-benzene), 6.87-6.90 (m, 2H, H-benzene), 6.16-6.19 (m, 2H), 6.03 (s, 1H), 5.50 (s, 1H, H-17), 4.63-4.69 (s, 1H, OH-6), 4.32 (d, 1H, J=12 Hz, H-13), 4.20-4.22 (m, 2H), 3.84 (s, 3H, H-methyl), 3.78-3.83 (m, 1H), 3. (d, 1H, J=12 Hz, −13), 2.50-2.70 (m, 1H), 2.35 (s, 3H, H-benzene methyl), 2.02 (s, 3H), 1.25-1.80 (m, 9H), 1.15 (s, 3H, CH$_3$-18), 1.13 (s, 3H, CH$_3$-19).

Compound BS-OR-092 was prepared by reacting 1-acetyloridonin with 3-nitrobenzoic acid according to the process for preparing BS-OR-090 using the same reagents:

MS (m/z): 556 [M+H]$^+$, 578 [M+Na]$^+$; HPLC: retention time 3.973 min (94.52%).

$^1$H NMR (300 MHz, CDCl$_3$): δ 8.82-8.83 (m, 1H, H-benzene), 8.37-8.42 (m, 1H, H-benzene), 8.25-8.28 (m, 1H, H-benzene), 7.57-7.62 (m, 1H, H-benzene), 6.24 (s, 1H, H-17), 6.17 (s, 1H), 6.07 (d, 1H, J=16 Hz), 5.58 (s, 1H, H-17), 4.63-4.69 (m, 1H, OH-6), 4.37 (d, 1H, J=16 Hz, H-13), 4.22 (d, 1H, J=16 Hz), 3.70-3.76 (m, 1H), 3.62 (s, 1H), 3.27 (d, 1H, J=12 Hz, H-13), 2.50-2.70 (m, 1H), 2.02 (s, 3H), 1.25-1.80 (m, 9H), 1.14 (s, 3H, CH$_3$-18), 1.12 (s, 3H, CH$_3$-19).

Compound BS-OR-093 was prepared by reacting 1-acetyloridonin with p-chlorobenzoic acid according to the process for preparing BS-OR-090 using the same reagents:

MS (m/z):567 [M+Na]$^+$; HPLC: retention time 6.305 min (93.27%).

$^1$H NMR (300 MHz, CDCl$_3$): δ 7.85-7.88 (m, 2H, H-benzene), 7.36-7.39 (m, 2H, H-benzene), 6.21 (s, 1H, H-17), 6.15 (s, 1H), 6.09 (d, 1H, J=12 Hz), 5.53 (s, 1H, H-17), 4.63-4.68 (m, 1H, OH-6), 4.33 (d, 1H, J=12 Hz, H-13), 4.20 (d, 1H, J=16 Hz), 3.87 (s, 1H), 3.74-3.80 (m, 1H), 3.27 (d, 1H, J=16 Hz, H-13), 2.50-2.70 (m, 1H), 2.02 (s, 3H), 1.26-1.80 (m, 9H), 1.14 (s, 3H, CH$_3$-18), 1.13 (s, 3H, CH$_3$-19).

Compound BS-OR-094 was prepared by reacting 1-acetyloridonin with cinnamic acid according to the process for preparing BS-OR-090 using the same reagents:

MS (m/z): 559 [M+Na]$^+$; HPLC: retention time 4.785 min (99.80%).

$^1$H NMR (300 MHz, CDCl$_3$): δ 7.66 (d, 1H, J=20 Hz, olefinic hydrogen), 7.37-7.51 (m, 5H, H-benzene), 6.35 (d, 1H, J=20 Hz, olefinic hydrogen), 6.15-6.19 (m, 2H), 5.93 (s, 1H), 5.52 (s, 1H, H-17), 4.63-4.67 (m, 1H, OH-6), 4.19-4.33 (m, 3H), 3.79-3.85 (m, 1H), 3.27 (d, 1H, J=12 Hz, H-13), 2.50-2.70 (m, 1H), 2.02 (s, 3H), 1.26-1.80 (m, 9H), 1.14 (s, 3H, CH$_3$-18), 1.13 (s, 3H, CH$_3$-19).

Example 9: The Synthesis of Compound BS-OR-095

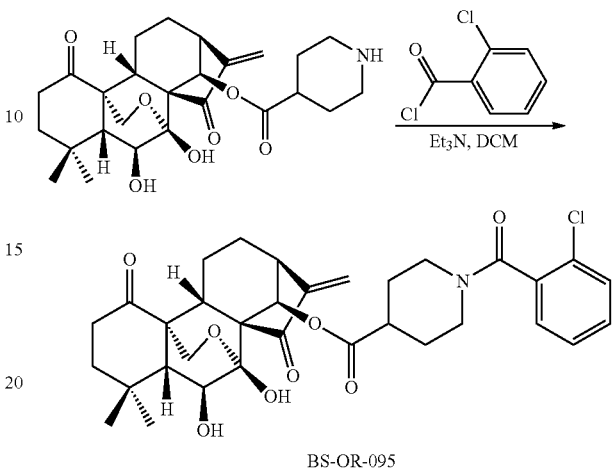

BS-OR-095

To 1-oxo-14-(4-acyloxypiperidine)oridonin trifluoroacetate (0.1 mmol) were added o-chlorobenzoyl chloride (26.3 mg, 0.15 mmol) and triethylamine (30.3 mg, 0.3 mmol). The reaction solution was stirred for 2 hours at room temperature. After the reaction was completed, dichloromethane (30 mL) and saturated sodium bicarbonate (30 mL) were added to the reaction solution, which was then separated into different layers to give the organic phase. The organic phase was washed with saturated saline solution, dried with anhydrous sodium sulfate, and rotavapped. The resulted crude product was separated via silica gel column (petroleum ether:ethyl acetate=2:1~1:1) to give compound BS-OR-095 (30 mg, 49% yield) as a white solid.

MS (m/z): 612.3 [M+H]$^+$, 634.3 [M+Na]$^+$; HPLC: retention time 5.132 min (93.37%).

1H NMR (300 MHz, CDCl$_3$) δ 7.38-7.19 (m, 4H), 6.26-6.24 (m, 1H), 5.93 (s, 1H, H-14), 5.6-5.61 (d, 1H), 5.36-5.32 (d, 1H, J=12.0 Hz, OH-6), 4.59-4.47 (m, 1H), 4.31-4.28 (d, 1H, J=10.5 Hz, H-20), 4.03-4.00 (d, 1H, J=10.5 Hz, H-20), 3.93-3.91 (m, 1H), 3.78-3.70 (m, 1H), 3.44-3.33 (m, 1H), 3.09-2.87 (m, 3H), 1.18 (s, 3H), 0.98 (s, 3H).

Example 10: The Synthesis of Compound BS-OR-099

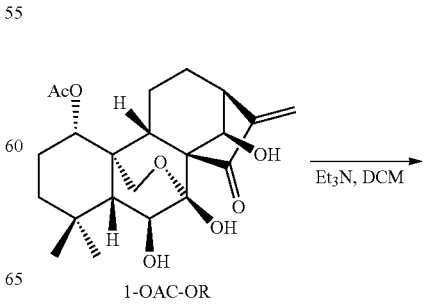

1-OAC-OR

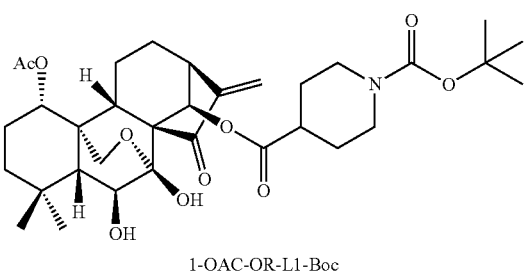

1-OAC-OR-L1-Boc

To dry dichloromethane (10 mL) was added N-Boc-4-piperidinecarboxylic acid (183.3 mg, 0.74 mmol), followed by oxalyl chloride (140 mg, 1.1 mmol). The reaction solution was stirred for 1.5 hours at room temperature followed by the removal of the solvent. Then 1-acetyloridonin (200 mg, 0.49 mmol) and triethylamine (222 mg, 2.2 mmol) in dichloromethane (5 mL) were added, and the reaction solution was stirred for 2 hours at room temperature. After the reaction was completed, dichloromethane (30 mL) and saturated sodium bicarbonate (30 mL) were added to the reaction solution, which was then separated into different layers to give the organic phase. The organic phase was washed with saturated saline solution, dried with anhydrous sodium sulfate, and rotavapped. The resulted crude product was separated via silica gel column (petroleum ether:ethyl acetate=3:1) to give compound 1-acetyl-14-(N-Boc-4-piperidineacyloxy)oridonin (230 mg, 76% yield) as a white solid.

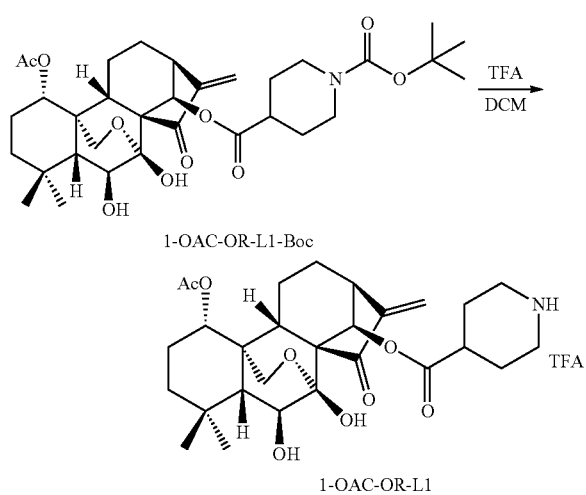

1-OAC-OR-L1-Boc

1-OAC-OR-L1

To dichloromethane (3 mL) was added 1-acetyl-14-(N-Boc-4-piperidineacyloxy)oridonin (92 mg, 0.15 mmol), followed by dropwise addition of trifluoroacetic acid (0.3 mL). The reaction solution was stirred for 1 hour at room temperature, and the solvent was rotavapped off after the reaction was completed. The resulted crude product was directly used in the subsequent reaction without purification.

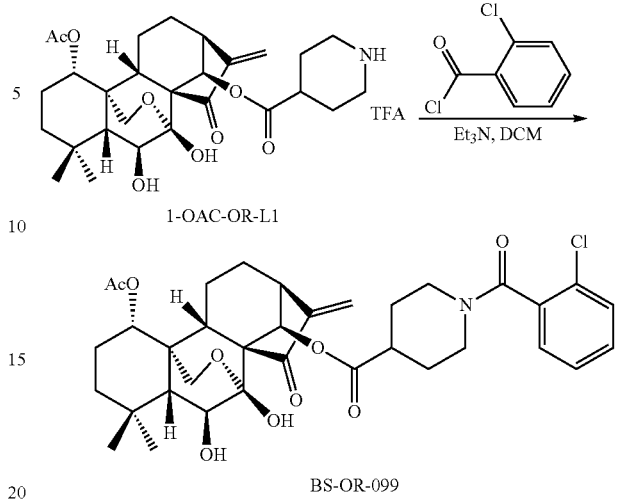

1-OAC-OR-L1

BS-OR-099

To dichloromethane (5 mL) was added the crude product (0.15 mmol) obtained from the last step, followed by triethylamine (222 mg, 2.2 mmol) and 2-chlorobenzoyl chloride (40 mg, 0.225 mmol). The reaction solution was stirred for 2 hours at room temperature and, after the reaction was completed, dichloromethane (30 mL) and saturated sodium bicarbonate (30 mL) were added thereto. The reaction solution was separated into different layers to give the organic phase, which was washed with saturated saline solution, dried with anhydrous sodium sulfate, and rotavapped. The resulted crude product was separated via silica gel column (petroleum ether:ethyl acetate=3:1) to give compound BS-OR-099 (28 mg, 28.5% yield) as a white solid.

MS (m/z): 656.3 [M+H]$^+$, 678.3 [M+Na]$^+$; HPLC: retention time 6.253 min (90.49%).

$^1$H NMR (300 MHz, CDCl$_3$) δ 7.38-7.23 (m, 1H), 6.16-6.11 (m, 2H), 5.86 (s, 1H, H-14), 5.53-5.49 (d, 1H, J=10.2 Hz), 4.64-4.56 (m, 2H), 4.30-4.26 (d, 1H, J=11.1 Hz, H-20), 4.20-4.16 (m, 1H), 4.03-4.07-3.99 (m, 1H), 3.80-3.73 (m, 1H), 3.45-3.33 (m, 1H), 2.60-2.45 (m, 2H), 1.99 (s, 3H), 1.12 (m, 6H).

Example 11: Evaluation of the 1-oxo/acylated-14-acylated oridonin Derivatives of the Present Invention for their Anti-Leukemia Activities (1) Experimental Materials Leukemia cell lines: leukemia cell lines: K562/adr (drug-resistant, chronic myeloid leukemia, CML), NB4 (acute promyelocytic leukemia, AML), Kasumi-1 (acute myeloid leukemia M2 type, AML-M2), Jurkat (acute lymphoblastic leukemia, ALL), all of which were donated by Cancer Research Institute of Zhejiang University, China; and H9 (acute lymphoblastic leukemia, ALL), which was purchased from China Center for Type Culture Collection.

Reagents: The standard sample of oridonin (OR) was purchased from Xi'an Hao-Xuan Biology Co., Ltd., Shaanxi, China; and the 1-oxo/acylated-14-acylated oridonin derivatives of the present invention.

Main apparatuses: an incubator (Model: Thermo Scientific 3111) and a microplate reader (Model: Bio-Rad iMark).

(2) Experimental Method 6000 well-growing leukemia cells were obtained and inoculated into wells of a 96-well cell culture plate. The culture medium was a RPMI-1640 cell culture medium containing 10% fetal bovine serum. On the next day, the 1-oxo/acylated-14-acylated oridonin derivatives of different concentrations were added and mixed uniformly. The plate was placed in a carbon dioxide cell incubator (5% $CO_2$) at 37° C. and was incubated for 72 hours. Then the viable cell concentration was determined by MTT method. In this experiment, the cell viability in control group (not treated with any compound) was set as 100%, and the cell viability (%) after treatment and the half maximal inhibitory concentration of the compound for the leukemia cell growth at 72 hours ($IC_{50}$ value 72 hours, μg/mL) were calculated.

(3) the Experimental Results

The experimental results are shown in Table 1.

Table 1 shows that the 1-oxo/acylated-14-acylated oridonin derivatives of the present invention can effectively induce the cell death of human chronic myeloid leukemia cells, acute myeloid leukemia cells and acute lymphocytic leukemia cells and inhibit the growth of these leukemia cells. As compared with oridonin itself, the 1-oxo/acylated-14-acylated oridonin derivatives of the present invention exhibit significant activities against these cell lines, wherein the compounds BS-OR-090 and BS-OR-093 are particularly prominent with their anti-K562/adr, anti-Kasumi-1 and anti-Jurkat cell line activities all increased by 3- to 4-fold and their anti-NB4 and anti-H9 cell line activities even increased by 15- and 22-fold. In addition, the anti-Kasumi-1 cell line activities of derivatives BS-OR-004 and BS-OR-005 are increased by more than 3-fold, and the anti-Jurkat cell line activities of BS-OR-005 and BS-OR-010 both are increased by almost 4-fold.

Example 12: Evaluation of the 1-oxo/acylated-14-acylated oridonin Derivatives of the Present Invention for their Anti-Human Multiple Myeloma Cell Activities (1) Experimental Materials Multiple myeloma cell lines: RPMI8226 (multiple myeloma), purchased from Fuxiang Bio-tech Co. Ltd., Shanghai, China.

Reagents: the same as in Example 11.

Main apparatuses: a Thermo Scientific 3111 incubator and a Bio-Rad iMark microplate reader.

(2) Experimental Method 6000 well-growing cells were obtained and inoculated into wells of a 96-well cell culture plate. The culture medium was a RPMI-1640 cell culture medium containing 10% fetal bovine serum. On the next day, the 1-oxo/acylated-14-acylated oridonin derivatives of different concentrations were added and mixed uniformly. The plate was placed in a carbon dioxide cell incubator (5% $CO_2$) at 37° C. and incubated for 72 hours. Then the viable cell concentration was determined by MTT method. In this experiment, the cell viability in control group (not treated with any compound) was set as 100% and the cell viability (%) after treatment and the half maximal inhibitiory concentration of the compound for the cell growth at 72 hours ($IC_{50}$ value 72 hours, μg/mL) were calculated.

(3) the Experimental Results

The experimental results are shown in table 2.

Table 2 shows that the 1-oxo/acylated-14-acylated oridonin derivatives of the present invention can induce the death of human myeloma cells and inhibit the growth of these tumor cells. As compared with oridonin per se, the anti-RPMI8226 cell activities of the 1-oxo/acylated-14-acy-

TABLE 1

Determination of the inhibiting concentrations of the 1-oxo/acylated-14-acylated oridonin derivatives on leukemia cell growth (72 h, $IC_{50}$ (μg/mL) value and $IC_{90}$ (μg/mL) value).

| Compound | K562/ADR | | Kasumi-1 | | NB4 | | Jurkat | | H9 | |
|---|---|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ | $IC_{50}$ | $IC_{90}$ |
| OR | 1.32 | 3.46 | 1.32 | 3.72 | 0.78 | 2.4 | 1.89 | 3.95 | 1.36 | 3.57 |
| BS-OR-001 | 0.6 | 1.73 | 0.72 | 1.86 | 0.14 | 0.47 | 0.68 | 2.63 | 0.45 | 0.95 |
| BS-OR-003 | 0.71 | 2.07 | 0.72 | 2.25 | 0.22 | 0.81 | 0.81 | 2.72 | 0.83 | 1.82 |
| BS-OR-004 | 0.41 | 1.72 | 0.41 | 1.68 | 0.13 | 0.76 | 0.62 | 2.7 | 0.34 | 0.83 |
| BS-OR-005 | 0.4 | 1.44 | 0.43 | 1.05 | 0.07 | 0.49 | 0.44 | 2.88 | 0.38 | 0.92 |
| BS-OR-007 | 0.47 | 1.86 | 0.71 | 1.76 | 0.08 | 0.47 | 0.71 | 4.45 | 0.41 | 0.92 |
| BS-OR-008 | 0.52 | 2.33 | 0.73 | 1.84 | 0.29 | 0.92 | 0.73 | 2.6 | 0.76 | 1.79 |
| BS-OR-010 | 0.44 | 1.98 | 0.57 | 1.76 | 0.15 | 0.95 | 0.48 | 6.06 | 0.38 | 0.96 |
| BS-OR-011 | 0.75 | 2.35 | 1.03 | 1.94 | 0.27 | 0.9 | 0.87 | 5.24 | 0.56 | 1.23 |
| BS-OR-012 | 0.75 | 3.2 | 1.15 | 2.39 | 0.32 | 1.3 | 0.99 | 5.77 | 0.75 | 1.99 |
| BS-OR-015 | 0.51 | 1.97 | 0.51 | 1.15 | 0.11 | 0.43 | 0.69 | 2.31 | 0.45 | 1.82 |
| BS-OR-017 | 0.52 | 1.9 | 0.69 | 1.7 | 0.14 | 0.82 | 0.92 | 5.63 | 0.53 | 0.98 |
| BS-OR-019 | 0.43 | 1.74 | 0.58 | 1.55 | 1.02 | 3.66 | 0.58 | 2.48 | 2.69 | 5.41 |
| BS-OR-020 | 0.73 | 2.31 | 0.76 | 2.85 | 0.27 | 1.34 | 0.88 | 4.31 | 0.89 | 1.84 |
| BS-OR-032 | 1.09 | 2.97 | 1.5 | 2.92 | 4.09 | 9.77 | 0.93 | 6.15 | 6.71 | 12.73 |
| BS-OR-034 | 1.52 | 4.77 | 1.58 | 3.46 | 0.5 | 1.94 | 1.32 | 5.36 | 0.78 | 1.73 |
| BS-OR-037 | 1.32 | 3.6 | 1.41 | 3.19 | 0.35 | 1.66 | 1.16 | 4.4 | 1.64 | 3.46 |
| BS-OR-038 | 1.43 | 3.92 | 1.1 | 3.95 | 0.44 | 2.63 | 1.36 | 5.91 | 1.42 | 3.01 |
| BS-OR-083 | 0.58 | 1.94 | 1.09 | 2.59 | 0.31 | 0.99 | 0.89 | 4.13 | 0.56 | 1.54 |
| BS-OR-090 | 0.36 | 1.48 | 0.37 | 1.3 | 0.05 | 0.94 | 0.4 | 2.62 | 0.06 | 0.37 |
| BS-OR-091 | 0.45 | 1.72 | 0.52 | 1.22 | 0.13 | 0.73 | 0.55 | 2.31 | 0.14 | 0.46 |
| BS-OR-093 | 0.37 | 1.57 | 0.41 | 1.31 | 0.05 | 0.47 | 0.44 | 3.03 | 0.06 | 0.33 |
| BS-OR-094 | 0.7 | 2.17 | 0.72 | 1.72 | 0.1 | 0.49 | 0.65 | 2.68 | 0.19 | 0.49 | lated oridonin derivatives BS-OR-005, BS-OR-010, BS-OR-090 and BS-OR-093 of the present invention increased by more than 9-fold.

Example 13: Evaluation of the 1-oxo/acylated-14-acylated oridonin Derivatives of the Present Invention for their Anti-Human Solid Tumor Effect (1) Experimental Materials
Human Solid Tumor Cell Lines:

Hep-2 (laryngeal carcinoma), A549 (human lung cancer), CaES-17 (esophageal cancer cell), PC-3 (prostate cancer), CNE (nasopharyngeal carcinoma cell) and SK-OV-3 (ovarian cancer cell), all of which were purchased from China Center For Type Culture Collection; RKO (human colon adenocarcinoma cell), MGC-803 (human gastric cancer cell), MG-63 (osteosarcoma), and U87-MG (malignant glioma cell), all of which were purchased from Fuxiang Bio-tech Co. Ltd., Shanghai, China; PANC-1 (pancreatic cancer), Becap37 (human breast cancer cell), Hela (human cervical cancer cell) and Hep G2 (human liver cancer cell), all of which were donated by Cancer Research Institute of Zhejiang University, China.

Reagents: the same as in Example 11.
Main apparatuses: a Thermo Scientific 3111 incubator and a Bio-Rad iMark microplate reader.
(2) Experimental Method 6000 well-growing human solid tumor cells were obtained and inoculated into wells of a 96-well cell culture plate. The culture medium was DMEM High Glucose cell culture medium containing 10% fetal bovine serum. The plate was placed in a carbon dioxide cell incubator (5% $CO_2$) at 37° C. and incubated for 24 hours. After added with 1-oxo/acylated-14-acylated oridonin derivatives of different concentration and mixed uniformly, the plate was placed in a carbon dioxide cell incubator (5% $CO_2$) at 37° C. and incubated for 72 hours. Then the viable cell concentration was determined by MTT method. In this experiment, the cell viability of control group (not treated with any compound) was set as 100% and the cell viability (%) after treatment and the half maximal inhibitiory concentration of the compound for the leukemia cell growth at 72 hours ($IC_{50}$ value 72 hours) were calculated.

(3) the Experimental Results

The experimental results are shown in Table 2.

Table 2 shows that the 1-oxo/acylated-14-acylated oridonin derivatives of the present invention have significant anti-human solid tumor activity and can induce the death of human solid tumor cells and inhibit the growth of these tumor cells. In comparison with oridonin per se, the anti-MGC-803 and anti-Hep-2 activities of the 1-oxo/acylated-14-acylated oridonin derivatives of the present invention BS-OR-090 and BS-OR-091 increased by almost 10-fold and 5-fold, respectively. The anti-CaEs-17 activities of BS-OR-004, BS-OR-005, BS-OR-019 and BS-OR-093 increased by more than 3-fold. The anti-CNE activities of BS-OR-004 and BS-OR-090 increased by almost 6-fold. In addition, the anti-SK-OV-3 activities of BS-OR-090 and BS-OR-093 increased by more than 7-fold. The anti-PANC-1 and anti-Hep G2 cell line activities of BS-OR-004, BS-OR-005 and BS-OR-090 all increased by almost 7- to 8-fold. The anti-Becap-37 and anti-RKO activities of BS-OR-004 and BS-OR-005 also both increased by more than 7-fold. The anti-MG-63 activities of BS-OR-004, BS-OR-005, BS-OR-019 and BS-OR-090 increased by more than 5-fold. The anti-Hela activity of BS-OR-090 increased by more than 5-fold. The anti-PC-3 activities of BS-OR-005 and BS-OR-090 also both increased by more than 5-fold.

TABLE 2

Determination of the inhibitory concentrations of the 1-oxo/acylated-14-acylated oridonin derivatives on human solid tumor cell growth (72 h, $IC_{50}$ (μg/mL) value and $IC_{90}$ (μg/mL) value).

| Compound | RPMI 8226 | | A549 | | PANC-1 | |
|---|---|---|---|---|---|---|
| | $IC_{50}$ | $IC_{90}$ | $IC_{50}$ | $IC_{90}$ | $IC_{50}$ | $IC_{90}$ |
| OR | 2.73 | 5.68 | 13.7 | >16 | 9.1 | 16 |
| BS-OR-001 | 0.41 | 1.89 | 2.6 | 6.08 | 1.79 | 6.42 |
| BS-OR-003 | 0.46 | 1.79 | 2.82 | 5.64 | 2.34 | 8.51 |
| BS-OR-004 | 0.31 | 1.77 | 1.71 | 4.9 | 1.31 | 8.24 |
| BS-OR-005 | 0.26 | 0.96 | 1.71 | 4.31 | 1.26 | 4.91 |
| BS-OR-007 | 0.37 | 2.59 | 2.13 | 5.34 | 1.63 | 8.55 |
| BS-OR-008 | 0.37 | 1.72 | 2.75 | 6.86 | 1.73 | 11.36 |
| BS-OR-010 | 0.28 | 1.78 | 2.83 | 7.29 | 1.86 | 10.69 |
| BS-OR-011 | 0.9 | 1.93 | 5.58 | 9.47 | 2.99 | 7.92 |
| BS-OR-012 | 0.92 | 3.48 | 5.55 | 10.69 | 4.11 | 10.18 |
| BS-OR-015 | 0.3 | 1.85 | 2.38 | 5.33 | 1.88 | 9.81 |
| BS-OR-017 | 0.5 | 1.88 | 2.93 | 6.29 | 1.96 | 5.76 |
| BS-OR-019 | 0.34 | 1.7 | 1.66 | 4.43 | 1.53 | 9.62 |
| BS-OR-020 | 0.59 | 3.84 | 2.76 | 5.78 | 2.32 | 6.09 |
| BS-OR-032 | 1.34 | 2.95 | 5.68 | 9.98 | 3.61 | 7.88 |
| BS-OR-034 | 1.48 | 3.83 | 6.43 | 11.94 | 4.99 | 11.9 |
| BS-OR-037 | 1.7 | 3.73 | 5.72 | 10.14 | 4.98 | 11.07 |
| BS-OR-038 | 0.97 | 3.58 | 6.1 | 10.21 | 4.7 | 11.38 |
| BS-OR-083 | 0.85 | 2.92 | 5.07 | 11.32 | 3.14 | 9.16 |
| BS-OR-090 | 0.2 | 1.61 | 1.82 | 6.27 | 1.31 | 4.41 |
| BS-OR-091 | 0.37 | 1.8 | 2.38 | 7.54 | 1.69 | 5.65 |
| BS-OR-093 | 0.2 | 1.55 | 1.78 | 6.68 | 1.69 | 9.36 |
| BS-OR-094 | 0.49 | 1.75 | 2.87 | 9.95 | 1.82 | 9.91 |

TABLE 2-continued

Determination of the inhibitory concentrations of the 1-oxo/acylated-14-acylated oridonin derivatives on human solid tumor cell growth (72 h, $IC_{50}$ (μg/mL) value and $IC_{90}$ (μg/mL) value).

| Compound | Becap-37 | | MG-63 | | Hep G2 | | RKO | |
|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ |
| OR | 5.06 | 12.95 | 1.86 | 5.6 | 6.77 | 13.12 | 2.24 | 3.96 |
| BS-OR-001 | 1.12 | 3.79 | 0.47 | 0.99 | 0.98 | 10.61 | 0.46 | 0.94 |
| BS-OR-003 | 1.12 | 3.09 | 0.48 | 2.74 | 1.69 | 7.48 | 0.66 | 1.49 |
| BS-OR-004 | 0.66 | 3.3 | 0.33 | 0.87 | 0.85 | 7.84 | 0.31 | 0.87 |
| BS-OR-005 | 0.7 | 2.78 | 0.28 | 0.75 | 0.84 | 5.27 | 0.31 | 0.84 |
| BS-OR-007 | 1.02 | 3.8 | 0.42 | 0.96 | 1.54 | 10.84 | 0.43 | 0.95 |
| BS-OR-008 | 1.08 | 3.35 | 0.42 | 0.98 | 1.74 | 12.57 | 0.47 | 0.94 |
| BS-OR-010 | 1.03 | 3.72 | 0.46 | 0.95 | 0.99 | 11.71 | 0.46 | 0.95 |
| BS-OR-011 | 1.96 | 6.11 | 0.74 | 3.01 | 2.53 | 12.6 | 0.59 | 1.44 |
| BS-OR-012 | 2.39 | 6.29 | 0.99 | 3.84 | 3.01 | 16 | 1.01 | 1.98 |
| BS-OR-015 | 0.99 | 3.17 | 0.4 | 0.96 | 0.94 | 5.47 | 0.42 | 0.94 |
| BS-OR-017 | 1.13 | 4.58 | 0.47 | 1.8 | 1.61 | 8.04 | 0.6 | 1.91 |
| BS-OR-019 | 0.89 | 8.43 | 0.35 | 0.79 | 0.94 | 14.61 | 0.38 | 0.89 |
| BS-OR-020 | 1.31 | 3.95 | 0.76 | 4.52 | 1.68 | 7.35 | 0.84 | 1.94 |
| BS-OR-032 | 2.93 | 10.47 | 0.98 | 1.97 | 3.17 | 17.17 | 0.89 | 1.99 |
| BS-OR-034 | 3.24 | 10.13 | 1.28 | 3.22 | 3.81 | >16 | 1.21 | 1.97 |
| BS-OR-037 | 2.75 | 7.47 | 1.2 | 3.1 | 3.33 | >16 | 0.91 | 1.84 |
| BS-OR-038 | 3.04 | 7.59 | 0.95 | 4.89 | 3.37 | 13.2 | 1.01 | 1.93 |
| BS-OR-083 | 2.21 | 6.5 | 0.76 | 1.7 | 2.83 | 11.94 | 0.68 | 1.68 |
| BS-OR-090 | 0.99 | 3.01 | 0.36 | 0.92 | 0.74 | 7.09 | 0.35 | 0.88 |
| BS-OR-091 | 1.26 | 2.48 | 0.49 | 1.46 | 1.4 | 6.28 | 0.41 | 0.93 |
| BS-OR-093 | 1.1 | 1.99 | 0.45 | 2.31 | 0.96 | 7.13 | 0.41 | 0.92 |
| BS-OR-094 | 1.15 | 3.31 | 0.47 | 1 | 1.42 | 7.47 | 0.38 | 0.75 |

| Compound | U87-MG | | Hela | | CaEs-17 | | CNE | |
|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ |
| OR | 2.58 | 6.67 | 5.22 | 10.71 | 3.31 | 6.86 | 5.45 | 10.53 |
| BS-OR-001 | 0.8 | 2.36 | 1.65 | 4.67 | 1.21 | 5.47 | 1.41 | 5.45 |
| BS-OR-003 | 0.99 | 2.82 | 1.84 | 5.31 | 1.49 | 5.23 | 1.93 | 6.62 |
| BS-OR-004 | 0.8 | 3.24 | 1.28 | 3.87 | 0.88 | 4.58 | 0.95 | 4.67 |
| BS-OR-005 | 0.7 | 2.16 | 1.16 | 3.4 | 0.81 | 3.03 | 1.09 | 4.45 |
| BS-OR-007 | 0.78 | 3.21 | 1.64 | 4.92 | 0.93 | 5.32 | 1.33 | 5.16 |
| BS-OR-008 | 0.86 | 2.4 | 1.45 | 3.9 | 1.22 | 4.75 | 2.16 | 10.47 |
| BS-OR-010 | 0.94 | 2.78 | 1.49 | 5.31 | 1.1 | 5.51 | 1.39 | 5.94 |
| BS-OR-011 | 1.17 | 3.29 | 2.53 | 6.79 | 1.41 | 5.24 | 2.26 | 8.1 |
| BS-OR-012 | 1.88 | 6.17 | 2.42 | 6.3 | 2.01 | 10.03 | 2.47 | 9.36 |
| BS-OR-015 | 0.87 | 2.41 | 1.53 | 3.75 | 0.95 | 3.05 | 1.05 | 4.05 |
| BS-OR-017 | 1.24 | 3.64 | 1.35 | 3.86 | 1.32 | 5.89 | 1.13 | 4.96 |
| BS-OR-019 | 0.77 | 2.43 | 1.43 | 3.74 | 0.89 | 5.62 | 7.19 | >16 |
| BS-OR-020 | 1.19 | 3.69 | 1.79 | 7.19 | 1.78 | 7.28 | 1.8 | 7.21 |
| BS-OR-032 | 1.26 | 4.56 | 2.63 | 5.67 | 1.62 | 11.72 | >16 | >16 |
| BS-OR-034 | 2.16 | 6.75 | 2.98 | 7.76 | 3.48 | 11.02 | 3.73 | 10.25 |
| BS-OR-037 | 1.86 | 4.68 | 3.41 | 10.06 | 3.07 | 11.16 | 2.95 | 8.76 |
| BS-OR-038 | 1.98 | 6.78 | 3.01 | 6.16 | 2.18 | 7.64 | 3.29 | 10.86 |
| BS-OR-083 | 1.29 | 4.61 | 1.92 | 4.95 | 1.71 | 10.22 | 1.52 | 4.42 |
| BS-OR-090 | 0.51 | 1.67 | 0.96 | 3.67 | 0.9 | 3.65 | 0.98 | 4.59 |
| BS-OR-091 | 0.67 | 1.98 | 1.28 | 3.51 | 0.99 | 4.83 | 1.18 | 4.52 |
| BS-OR-093 | 0.56 | 1.89 | 1.02 | 3.45 | 0.86 | 5.21 | 1.31 | 5.02 |
| BS-OR-094 | 0.6 | 1.86 | 1.54 | 4.45 | 0.94 | 6.26 | 1.32 | 5.04 |

| Compound | Hep-2 | | MGC-803 | | PC-3 | | SK-OV-3 | |
|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ |
| OR | 4.66 | 7.99 | 5.88 | 7.95 | 7.94 | 12.96 | 7.94 | 12.96 |
| BS-OR-001 | 1.64 | 7.7 | 0.88 | 10.96 | 1.67 | 3.8 | 1.67 | 3.8 |
| BS-OR-003 | 1.85 | 7.56 | 1.43 | 10.73 | 1.82 | 3.82 | 1.82 | 3.82 |
| BS-OR-004 | 1.38 | 6.79 | 0.65 | 4.88 | 1.45 | 3.94 | 1.45 | 3.94 |
| BS-OR-005 | 1.3 | 5.6 | 0.7 | 5.4 | 1.22 | 3.16 | 1.22 | 3.16 |
| BS-OR-007 | 1.76 | 9.2 | 0.95 | 9.79 | 1.69 | 4.6 | 1.69 | 4.6 |
| BS-OR-008 | 3.11 | 13.18 | 1.39 | 3.89 | 1.59 | 3.67 | 1.59 | 3.67 |
| BS-OR-010 | 1.8 | 9.11 | 0.68 | 9.04 | 1.66 | 4.77 | 1.66 | 4.77 |
| BS-OR-011 | 3.8 | 14.06 | 1.6 | 11.94 | 2.53 | 4.87 | 2.53 | 4.87 |
| BS-OR-012 | 3.61 | 14.74 | 1.79 | 3.99 | 3.48 | 7.54 | 3.48 | 7.54 |
| BS-OR-015 | 1.12 | 5.05 | 0.84 | 4.68 | 1.66 | 3.04 | 1.66 | 3.04 |
| BS-OR-017 | 1.62 | 6.93 | 0.91 | 4.16 | 1.99 | 3.92 | 1.99 | 3.92 |
| BS-OR-019 | 10.71 | >16 | 4.98 | 12.04 | 1.41 | 3.86 | 1.41 | 3.86 |
| BS-OR-020 | 1.92 | 7.4 | 1.65 | 8.86 | 2.56 | 7.07 | 2.56 | 7.07 |
| BS-OR-032 | >16 | >16 | 12.7 | >16 | 3.07 | 5.41 | 3.07 | 5.41 |
| BS-OR-034 | 3.97 | 13.35 | 2.89 | 8.83 | 3.88 | 9.45 | 3.88 | 9.45 |

TABLE 2-continued

Determination of the inhibitory concentrations of the 1-oxo/acylated-
14-acylated oridonin derivatives on human solid tumor cell growth (72 h,
IC$_{50}$ (µg/mL) value and IC$_{90}$ (µg/mL) value).

| | | | | | | | |
|---|---|---|---|---|---|---|---|
| BS-OR-037 | 3.58 | 15.26 | 3.18 | 6.35 | 3.48 | 7.08 | 3.48 | 7.08 |
| BS-OR-038 | 4.34 | 13.93 | 3.36 | 9.55 | 5.3 | 11.57 | 5.3 | 11.57 |
| BS-OR-083 | 3.13 | 15.5 | 1.26 | 5.57 | 3.16 | 6.8 | 3.16 | 6.8 |
| BS-OR-090 | 0.96 | 5.71 | 0.52 | 6.3 | 1.35 | 5.37 | 1.35 | 5.37 |
| BS-OR-091 | 0.96 | 6.65 | 0.59 | 5.7 | 1.75 | 4.71 | 1.75 | 4.71 |
| BS-OR-093 | 1.42 | 6.91 | 0.79 | 6.73 | 1.6 | 5.12 | 1.6 | 5.12 |
| BS-OR-094 | 1.68 | 7.46 | 1.39 | 12.08 | 1.66 | 4.52 | 1.66 | 4.52 |

The invention claimed is:

1. A 1-oxo/acylated-14-acylated oridonin derivative of formula (I), or a pharmaceutically acceptable salt thereof,

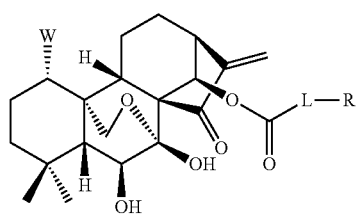

I wherein
 W is oxo or —O(CO)R';
 L is a direct bond;
 R' is $C_1$-$C_6$ alkyl;
 R is phenyl or heteroaryl; wherein, the phenyl and heteroaryl are respectively optionally substituted with a substituent selected from the group consisting of chloro, bromo, nitro, cyano, methoxy, ethoxy, propoxy, methyl, ethyl, propyl, isopropyl, n-butyl, isobutyl, or tert-butyl.

2. The 1-oxo/acylated-14-acylated oridonin derivative or a pharmaceutically acceptable salt thereof according to claim 1, wherein W is oxo or formyloxy.

3. The 1-oxo/acylated-14-acylated oridonin derivative or a pharmaceutically acceptable salt thereof according to claim 1, wherein the heteroaryl is a five-membered or six-membered aromatic ring group containing oxygen, nitrogen, or sulfur heteroatom.

4. The 1-oxo/acylated-14-acylated oridonin derivative or a pharmaceutically acceptable salt thereof according to claim 3, wherein the heteroaryl is furyl, thienyl, pyrrolyl, or pyridyl.

5. The 1-oxo/acylated-14-acylated oridonin derivative or a pharmaceutically acceptable salt thereof according to claim 1, selected from the group consisting of the following compounds:

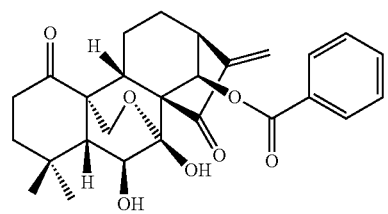

BS-OR-001

-continued

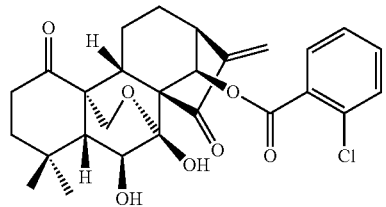

BS-OR-003

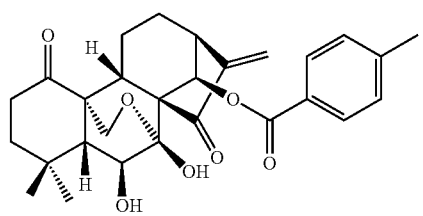

BS-OR-004

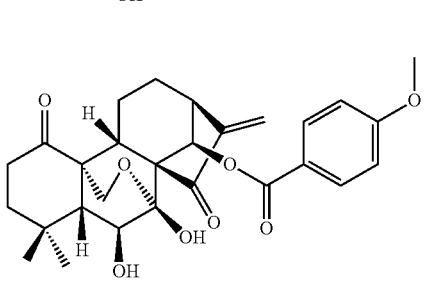

BS-OR-005

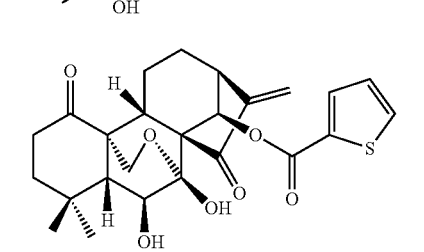

BS-OR-007

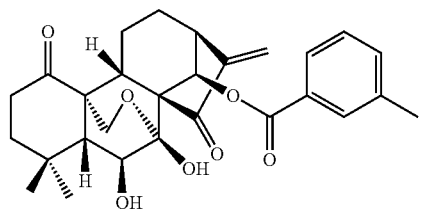

BS-OR-008

BS-OR-010
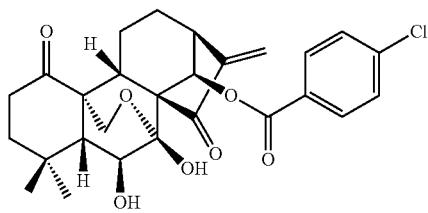
BS-OR-011
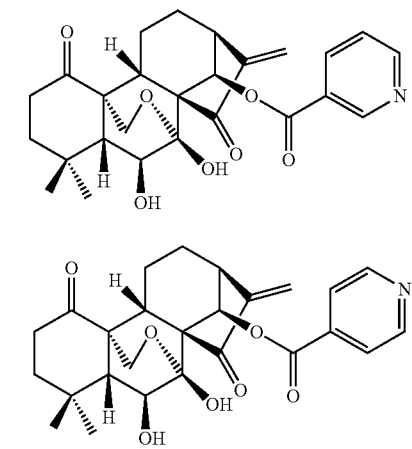
BS-OR-12
BS-OR-015
BS-OR-020
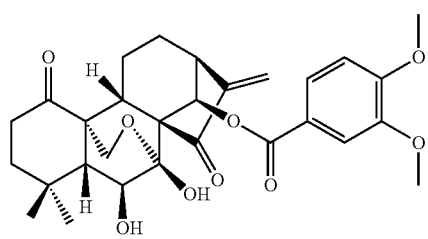
BS-OR-090
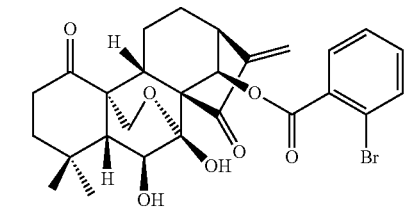
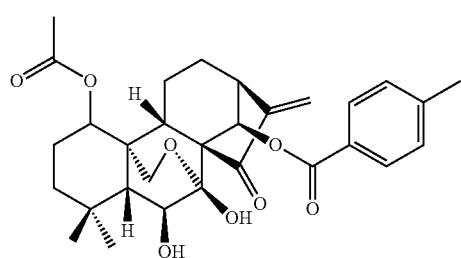
BS-OR-091
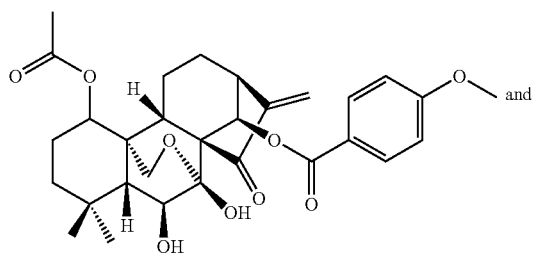 and
BS-OR-093
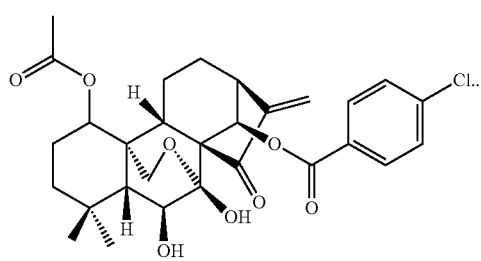
6. The 1-oxo/acylated-14-acylated oridonin derivative or a pharmaceutically acceptable salt thereof according to claim 1, selected from the group consisting of the following compounds:
BS-OR-004
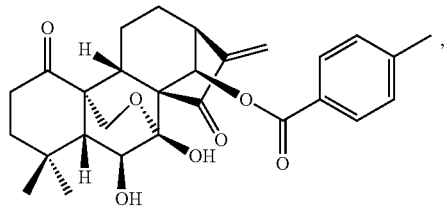
1-oxo-14-(4-methyl)benzoyloxy oridonin
BS-OR-005
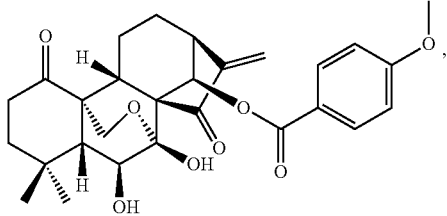
1-oxo-14-(4-methoxy)benzoyloxy oridonin
BS-OR-090
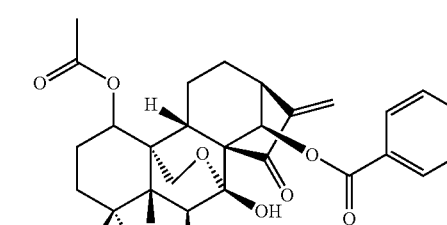
1-acetyl-14-(4-methyl)benzoyloxy oridonin -continued

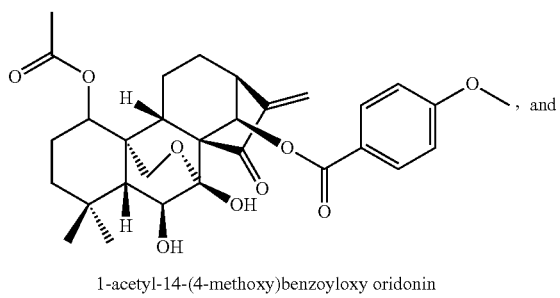

1-acetyl-14-(4-methoxy)benzoyloxy oridonin

BS-OR-091

BS-OR-093

1-acetyl-14-parachlorobenzoyloxy oridonin

7. A process for preparing the compound of formula (I-1):

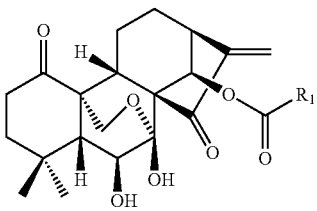

(I-1)

wherein R₁ is R as defined in claim 1,
said process comprises first selectively oxidizing the 1-position hydroxyl of oridonin

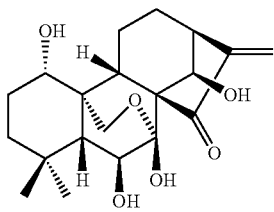

to produce a 1-oxo oridonin intermediate (OR-Ketone):

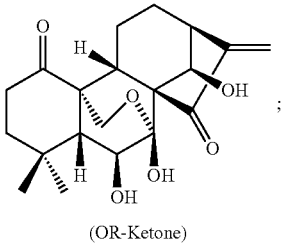

(OR-Ketone)

then subjecting the intermediate to acylation with a corresponding organic acid, organic anhydride or organic acyl chloride in the presence of an alkali to produce a 1-oxo-14-acylated oridonin derivative of formula (I-1),

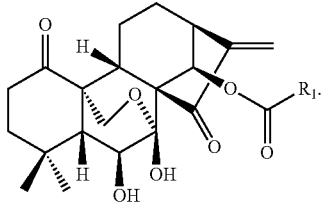

(I-1)

8. A pharmaceutical composition, comprising the 1-oxo/acylated-14-acylated oridonin derivative or a pharmaceutically acceptable salt thereof according to claim 1 and optionally a pharmaceutically acceptable excipient.

9. A method for relieving or inhibiting a tumor in a subject, comprising administrating to the subject in need thereof an effective amount of the 1-oxo/acylated-14-acylated oridonin derivative or a pharmaceutically acceptable salt thereof according to claim 1.

10. The method according to claim 9, wherein the tumor is selected from the group consisting of leukemia, multiple myeloma, lymphoma, liver cancer, gastric cancer, breast cancer, cholangiocellular carcinoma, pancreatic cancer, lung cancer, colorectal cancer, osteosarcoma, human cervical cancer, glioma, nasopharyngeal carcinoma, laryngeal carcinoma, esophageal cancer, middle ear tumor, melanoma and prostate cancer.

11. The 1-oxo/acylated-14-acylated oridonin derivative:

BS-OR-004

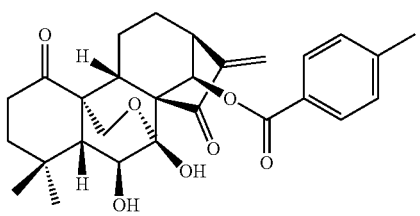

1-oxo-14-(4-methyl)benzoyloxy oridonin, or a pharmaceutically acceptable salt thereof.

12. A pharmaceutical composition, comprising:

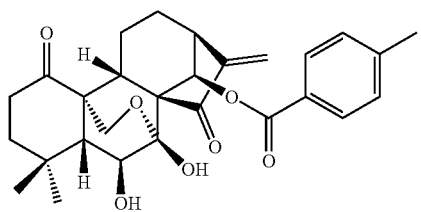

BS-OR-004

1-oxo-14-(4-methyl)benzoyloxy oridonin, or a pharmaceutically acceptable salt thereof, and optionally a pharmaceutically acceptable excipient.

13. The method according to claim 9, wherein the oridonin derivative is

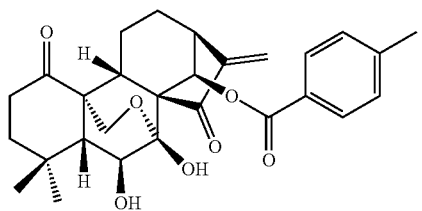

BS-OR-004

1-oxo-14-(4-methyl)benzoyloxy oridonin, or a pharmaceutically acceptable salt thereof.

14. The 1-oxo/acylated-14-acylated oridonin derivative:

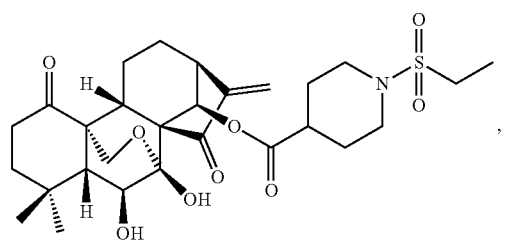

BS-OR-038 or a pharmaceutically acceptable salt thereof.

15. The 1-oxo/acylated-14-acylated oridonin derivative of claim 1, wherein R is heteroaryl.

16. The 1-oxo/acylated-14-acylated oridonin derivative of claim 1, wherein

R is phenyl or heteroaryl;

wherein the phenyl is substituted with a substituent selected from the group consisting of nitro, cyano, methoxy, ethoxy, propoxy, methyl, ethyl, propyl, isopropyl, n-butyl, isobutyl, or tert-butyl; and wherein the heteroaryl is optionally substituted with a substituent selected from the group consisting of chloro, bromo, nitro, cyano, methoxy, ethoxy, propoxy, methyl, ethyl, propyl, isopropyl, n-butyl, isobutyl, or tert-butyl.

17. A process for preparing the compound of formula (I-4):

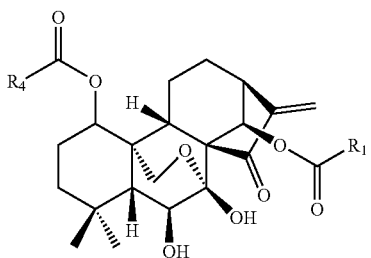

(I-4)

wherein $R_1$ is R as defined in claim 1, $R_4$ is R' as defined in claim 1, said process comprises first subjecting the hydroxyl groups at the 7- and 14-positions of oridonin

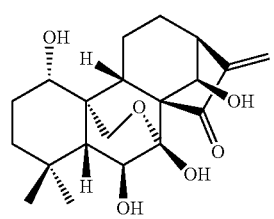

to acetal protection to produce OR-2

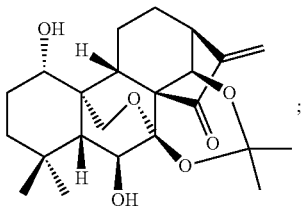

(OR-2)

then subjecting the 1-position hydroxyl of OR-2 to acylation to produce an intermediate OR-3

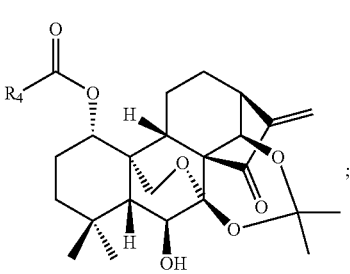

(OR-3)

treating OR-3 with an acid for deprotection to produce an intermediate OR-4

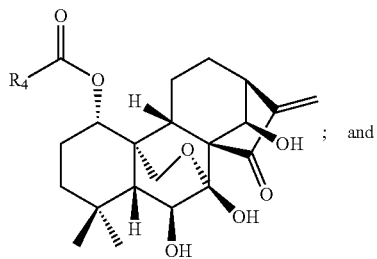
(OR-4)
subjecting OR-4 to acylation to produce 1,14-diacylated oridonin derivative of formula (I-4)
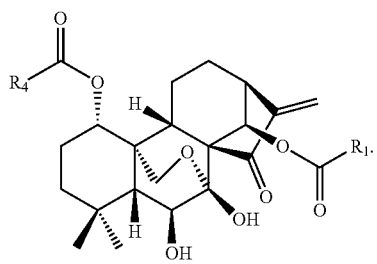
(I-4)
* * * * *